United States Patent [19]

Wetzel et al.

[11] 4,415,566
[45] Nov. 15, 1983

[54] CEPHALOSPORIN DERIVATIVES

[75] Inventors: Bernd Wetzel; Eberhard Woitun, both of Biberach; Wolfgang Reuter, Laupertshausen; Roland Maier, Biberach; Uwe Lechner, Ummendorf; Hanns Goeth, Biberach, all of Fed. Rep. of Germany

[73] Assignee: Boehringer Ingelheim GmbH, Ingelheim am Rhein, Fed. Rep. of Germany

[21] Appl. No.: 191,423

[22] Filed: Sep. 26, 1980

Related U.S. Application Data

[63] Continuation-in-part of Ser. No. 163,194, Jun. 26, 1980, abandoned.

Foreign Application Priority Data

[30] Jul. 13, 1979 [DE] Fed. Rep. of Germany ....... 2938344

[51] Int. Cl.³ ................ C07D 501/36; A61K 31/545
[52] U.S. Cl. ................................. 424/246; 544/27; 544/21; 260/239.1; 424/21; 544/28
[58] Field of Search ................ 260/239.1; 544/16, 21, 544/26, 27; 424/246

[56] References Cited
U.S. PATENT DOCUMENTS 4,208,412 6/1980 Preiss et al. .................. 424/263
4,258,184 3/1981 Kai et al. ...................... 544/27

*Primary Examiner*—Nicholas S. Rizzo
*Attorney, Agent, or Firm*—Hammond & Littell, Weissenberger & Muserlian

[57] ABSTRACT

Penicillins and cephalosporins of the formula

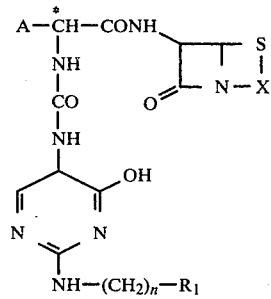

wherein

A is phenyl, 4-hydroxyphenyl, cyclohexyl, cyclohene-1-yl, cyclohexa-1,4-diene-1-yl, 2-thienyl, 3-thienyl, 2-furyl, 3-furyl or 3,4-disubstituted phenyl, where the substituents, which may be identical to or different from each other, are each chlorine, hydroxyl or methoxy;

$R_1$ is an unsubstituted or substituted 5- or 6-membered heterocycle comprising carbon atoms and 1 to 4, preferably 1 to 2, identical or different heteroatoms such as oxygen, sulfur or nitrogen;

n is 0 or 1;

X is

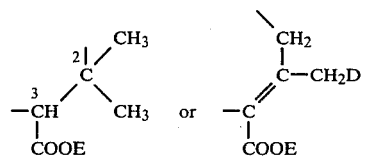

D is hydrogen, hydroxyl, acetoxy, aminocarbonyloxy, pyridinium, aminocarbonyl-pyridinium or S-Het, where Het is 1-methyl-tetrazol-5-yl, tetrazol-5-yl, 3-methyl-1,2,4-thiadiazol-5-yl, 1,2,4-triazol-5-yl, 1,3,4-thiadiazol-5-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,2,4-thiadiazol-5-yl, 2-acetylamino-1,3,4-thiadiazol-5-yl, 2-methyl-1,3,4-oxadiazol-5-yl, 1,2,3-triazol-4-yl or 1,2,4-triazol-3-yl; and E is hydrogen or a protective group which is easily removable in nitro or in vivo, especially an ester-forming group which can be removed under mild conditions by hydrogenation or hydrolysis or other treatments, or an ester-forming group which can easily be split off in the living organism;

and, when E is hydrogen, their non-toxic, pharmacologically acceptable salts thereof, such as their alkali metal or alkaline earth metal salts, especially the sodium, potassium, magnesium or calcium salts; their ammonium salts; or their organic amine salts, especially the triethylamine or dicyclohexylamine salts. The compounds are useful as antibiotics.

6 Claims, No Drawings

CEPHALOSPORIN DERIVATIVES

CROSS REFERENCE TO RELATED APPLICATION

This application is a continuation-in-part of co-pending U.S. patent application Ser. No. 163,194, filed on June 26, 1980, now abandoned, incorporated herein by reference.

This invention relates to novel β-lactams and salts thereof, to methods of preparing these compounds, to pharmaceutical compositions containing them as active ingredients, and to methods of using them as antibiotics.

More particularly, the present invention relates to a novel class of compounds represented by the formula

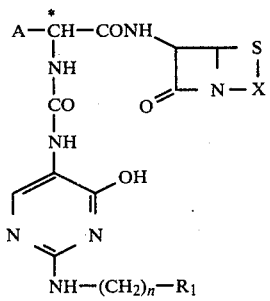

(I)

wherein
A is phenyl, 4-hydroxyphenyl, cyclohexyl, cyclohexene-1-yl, cyclohexa-1,4-diene-1-yl, 2-thienyl, 3-thienyl, 2-furyl, 3-furyl or 3,4-disubstituted phenyl, where the substituents, which may be identical to or different from each other, are each chlorine, hydroxyl or methoxy;

$R_1$ is an unsubstituted or substituted 5- or 6-membered heterocycle comprising carbon atoms and 1 to 4, preferably 1 to 2, identical or different heteroatoms such as oxygen, sulfur or nitrogen;

n is 0 or 1;
X is

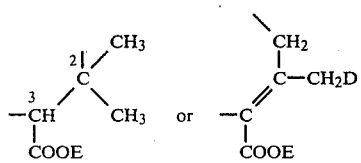

D is hydrogen, hydroxyl, acetoxy, aminocarbonyloxy, pyridinium, aminocarbonyl-pyridinium or the group S-Het, where Het is 1-methyltetrazol-5-yl, tetrazol-5-yl, 3-methyl-1,2,4-thiadiazol-5-yl, 1,2,4-thiadiazol-5-yl, 1,3,4-thiadiazol-5-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 2-methyl-1,3,4-oxadiazol-5-yl, 1,2,3-triazol-4-yl or 1,2,4-triazol-3-yl; and E is hydrogen or a protective group which is easily removable in vitro or in vivo, such as those which have heretofore been used in the field of penicillins and cephalosporins, especially ester-forming groups which can be removed under mild conditions by hydrogenation or hydrolysis or other treatments, or ester-forming groups which can easily be split off in the living organism;

and, when E is hydrogen, their non-toxic, pharmacologically acceptable salts thereof, such as their alkali metal or alkaline earth metal salts, especially the sodium, potassium, magnesium or calcium salts; their ammonium salts; or their organic amine salts, especially the triethylamine or dicyclohexylamine salts.

In vitro easily removable protective groups are, for example, benzyl, diphenylmethyl, trityl, tert. butyl, 2,2,2-trichloroethyl or trimethylsilyl.

In vivo easily removable protective groups are, for example, alkanoyloxyalkyl, such as acetoxymethyl, propionyloxymethyl, 2-acetoxyethyl or pivaloyloxymethyl, phthalidyl or indanyl.

When D is pyridinium or aminocarbonylpyridinium, the compounds of this invention have the formula

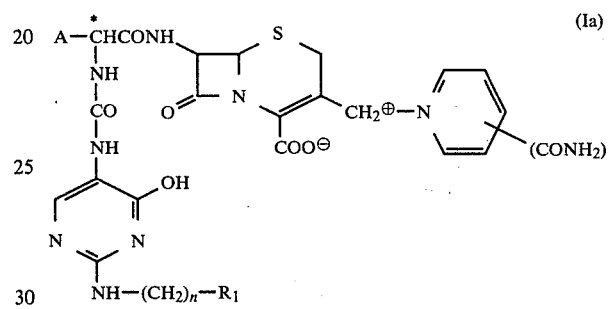

(Ia)

Examples of $R_1$ in formulas I and Ia are unsubstituted or substituted thienyl, furyl, pyrrolyl, oxazolyl, isoxazolyl, thiazolyl, isothiazolyl, imidazolyl, pyrazolyl, oxadiazolyl, thiadiazolyl, triazolyl, tetrazolyl, pyridyl, pyrazinyl, pyridazinyl, pyrimidinyl or tetrahydrofuranyl groups, where these groups may be substituted by alkyl groups, by halogen atoms such as fluorine, chlorine or bromine, by nitro, cyano, amino, alkyl- or dialkylamino groups, by alkylcarbonylamino or alkoxycarbonylamino groups, by hydroxy, alkoxy, alkylthio, alkylsulfinyl or alkylsulfonyl groups, by methylsulfonylamino, aminocarbonyl, alkylcarbonyloxy, or alkoxycarbonyl groups, aminosulfonyl, alkylamino, or dialkylaminosulfonyl groups, where the alkyl moieties in these substituents may each contain 1 to 4 carbon atoms, as well as by a carboxylic acid or sulfonic acid group.

A preferred sub-genus is constituted by those compounds of the formula I
wherein
A is phenyl, p-hydroxyphenyl, 3,4-dihydroxyphenyl, 2-thienyl, 3-thienyl, 2-furyl or 3-furyl;
E is hydrogen, 2-acetoxy-ethyl or pivaloyloxymethyl;
D has the meanings defined in formula I; and
—$(CH_2)_n$—$R_1$ is 2-tetrahydrofuryl-methyl, 3-pyridyl, 6-substituted-3-pyridyl, 2-substituted-3-pyridyl, 2-, 3- or 4-pyridylmethyl, 2-, 4- or 5-pyrimidinylmethyl, 2-substituted-5-pyrimidinylmethyl, 4-hydroxy-5-pyrimidinyl, 2-substituted-4-hydroxy-5-pyrimidinyl 5-pyrimidinyl, 2-substituted-5-pyrimidinyl, 4-substituted-2-pyrimidinyl, 4,6-disubstituted-2-pyrimidinyl, 2-substituted-4-pyrimidinyl, 2,6-disubstituted-4-pyrimidinyl, 5-substituted-2-furyl, 5-substituted-2-thienyl, 2- or 3-furylmethyl, 2- or 3-thienylmethyl, 5-substituted-2-thienylmethyl, a 5-substituted-2-furylmethyl or 4-substituted-2-thiazolyl, where the substituents in these groups can have the meanings specified above in connection with $R_1$ in formula I; 2-imidazolyl, 2-imidazolylmethyl, 2-thiazolylmethyl, 2-oxazolyl, 2-oxazolylmethyl, 1,2,4-triazolyl, 1,2,4-triazolylmethyl, 5-methyl-2-(1,3,4-)-thiadiazolyl or tetrazolylmethyl, all optionally substituted by a methyl radical; and, when E is hydrogen, non-toxic, pharmacologically acceptable salts thereof.

A particularly preferred sub-genus is constituted by those compounds of the formula I,
wherein A is phenyl, p-hydroxyphenyl, 2-thienyl, 2-furyl or 3-furyl;

E is hydrogen or pivaloyloxymethyl;

D is hydrogen, acetoxy, aminocarbonyloxy or S-Het, where Het is tetrazol-5-yl, 1-methyl-tetrazol-5-yl, 1,3,4-thiadiazol-5-yl or 2-methyl-1,3,4-thiadiazol-5-yl; and —(CH$_2$)$_n$—R$_1$ is 3-pyridyl, 6-methylsulfinyl-3-pyridyl, 6-methylsulfonyl-3-pyridyl, 6-hydroxy-3-pyridyl, 5-pyrimidinylmethyl, 2-methyl-5-pyrimidinylmethyl, 2-methyl- or 2-hydroxy-5-pyrimidinyl, 4-hydroxy-2-pyrimidinyl, 4,6-dihydroxy-2-pyrimidinyl, 3-pyridylmethyl, 2-furylmethyl, 2-thienylmethyl, 5-aminosulfonyl-2-thienylmethyl, 5-aminocarbonyl-thienyl or 5-ethoxycarbonyl-thienyl;

and, when E is hydrogen, non-toxic, pharmacologically acceptable salts thereof.

An especially preferred sub-genus is constituted by those compounds of the formula I,
wherein A is p-hydroxyphenyl or 2-thienyl;

E is hydrogen;

D is acetoxy or 1-methyl-tetrazol-5-yl;

—(CH$_2$)$_n$—R$_1$ is 3-pyridylmethyl, 6-methylsulfinyl-3-pyridyl, 6-methyl-sulfonyl-3-pyridyl, 6-hydroxy-3-pyridyl, 2-methyl-5-pyrimidinyl-methyl, 2-hydroxy-5-pyrimidinyl, 4-hydroxy-2-pyrimidinyl, 4,6-dihydroxy-2-pyrimidinyl, 5-aminocarbonylthienyl, 2-thienylmethyl, 5-aminosulfonyl-2-thienylmethyl or 2-furylmethyl;

and non-toxic, pharmacologically acceptable salts thereof.

The β-lactams of the formula I exist in two tautomeric forms, that is, the lactim and the lactam form. Which of the two forms I or I' is predominant, depends particularly on the respective solvent and on the type of substituent —NH(CH$_2$)$_n$R$_1$:

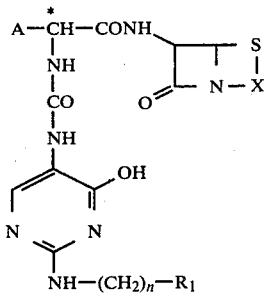
(I)

(I')

With regard to the chiral center C, the compounds of the formula I may be present in two possible R- and S-configurations or as mixtures of these. Particularly preferred are those compounds which have the D=R-configuration. If the end product is obtained in the D,L-form, the pure D- and L-diastereoisomers can be separated by preparative high pressure liquid chromatography (HPLC).

The compounds of the formula I may be prepared by the following methods:

METHOD A

For the preparation of a compound of the formula I wherein D has the meanings previously defined with the exception of pyridinium or aminocarbonylpyridinium, by reacting a compound of the formula

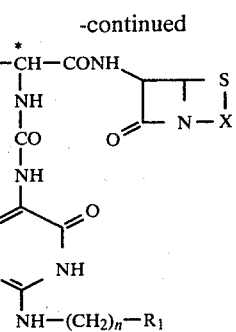
(II)

wherein

A and X have the meanings previously defined, and

D has the meanings previously defined with the exception of pyridinium or aminocarbonylpyridinium, with a pyrimidine derivative of the formula (III)

wherein

R$_1$ and n have the meanings previously defined, and

B is —NCO or a reactive derivative of —NHCOOH, such as —NHCOCl, —NHCOBr or

—NH—COO—⟨aryl⟩—NO$_2$, where —NCO and —NHCOCl are especially preferred.

Also mixtures of such pyrimidine derivatives of the formula III can be used, wherein B has partly the one and partly the other of the above-mentioned meanings, for instance —NCO and —NHCOCl simultaneously.

If E is hydrogen, the starting compounds of the formula II can be used in the form of their inorganic or organic salts, for instance as the triethylammonium salts or the sodium salts. In that case the reaction can be carried out in any desired mixtures of water and those organic solvents which are miscible with water such as ketones, for example acetone; cyclic ethers, for example tetrahydrofuran or dioxane; nitriles, for example acetonitril; formamides, for example dimethylformamide; dimethylsulfoxide; or alcohols, for example isopropanol; or in hexametapol. By addition of a base or by use of a buffer solution, the pH of the reaction mixture is kept in a pH range of about 2.0 to 9.0, preferably between 6.5 and 8.0. However, it is also possible to carry out the reaction in an anhydrous organic solvent, such as halogenated hydrocarbons like chloroform or methylene chloride, in the presence of a base, preferably triethylamine, diethylamine or N-ethylpiperidine.

The reaction can further be carried out in a mixture of water and a water-immiscible solvent, such as an ether, for example diethyl ether; a halogenated hydrocarbon, for example chloroform or methylene chloride; carbon disulfide; a ketone, for example isobutylmethyl ketone; an ester, for example ethyl acetate; or an aromatic solvent, for example benzene, where it is advantageous to stir vigorously and to keep the pH value in a range of about 2.0 to 9.0, preferably between 6.5 and 8.0, by addition of a base or by use of a buffer solution. The reaction can be carried out, however, also in water alone in the presence of an organic or inorganic base or of a buffer substance.

If E is trimethylsilyl, that is, if a silyl derivative of a compound of the formula II, such as a mono- or, more advantageously, a di-trimethylsilyl derivative silylated at the amino and carboxyl group, is used as the starting compound, and it is reacted with a compound of the formula III, the reaction is generally advantageously carried out in an anhydrous solvent or a solvent free from hydroxyl groups, for example in a halogenated hydrocarbon, such as methylene chloride or chloroform, benzene, tetrahydrofuran, acetone or dimethylformamide, etc. The addition of a base is not essential, but may be of advantage in individual cases to improve the yield or the purity of the end product. Examples of such bases are tertiary aliphatic or aromatic amines, such as pyridine or triethylamine, or by steric hindrance difficultly acylatable secondary amines, such as dicyclohexylamine.

If E is one of the above-mentioned in vitro or in vivo easily removable protective groups, such as diphenylmethyl or pivaloyloxymethyl, it is of advantage to perform the reaction in an aprotic solvent, such as absolute methylene chloride, chloroform, tetrahydrofuran or dimethylformamide.

The amount of base to be used is determined, for example, by the desired maintenance of a certain pH valued.

Where no pH measurement or adjustment is made or where no measurement is possible or practical because of a lack of sufficient water in the diluting agent, 1.0 to 2.0 mol-equivalents of base are used when silylated compounds of the formula II are not present. When such silylated compounds are present, preferably up to one mol-equivalent of base is used.

In general, all organic and inorganic bases which are usually used in organic chemistry, can be used as base additives. Such bases may be alkali metal and alkaline earth metal hydroxides, alkaline earth metal oxides, alkali metal and alkaline earth metal carbonates and bicarbonates, ammonia, primary, secondary and tertiary aliphatic and aromatic amines, as well as heterocyclic bases. Preferred bases are sodium, potassium and calcium hydroxide, calcium oxide, sodium and potassium carbonate, sodium and potassium bicarbonate, ethylamine, methylethylamine, triethylamine, hydroxyethylamine, aniline, dimethylaniline, pyridine and piperidine. When using silylated starting compounds, however, the above-mentioned restrictions concerning the kind of base should be considered.

Suitable buffer systems include all the usual buffer mixtures, such as phosphate buffer, citrate buffer and tris-(hydroxymethyl)-amino-methane buffer.

The reaction temperatures can be varied over a wide range. In general, the reaction is carried out between $-20°$ and $+50°$ C., preferably between $0°$ and $+20°$ C.

The reaction partners of the formulas II and III can be reacted with each other in equimolar quantities. However, in some cases it may be advantageous to use one of the reaction partners in excess to facilitate the purification of the end product or to increase the yield.

METHOD B

For the preparation of a compound of the formula I wherein D has the meanings previously defined with the exception of pyridinium or aminocarbonylpyridinium, by reacting a ureidocarboxylic acid of the formula

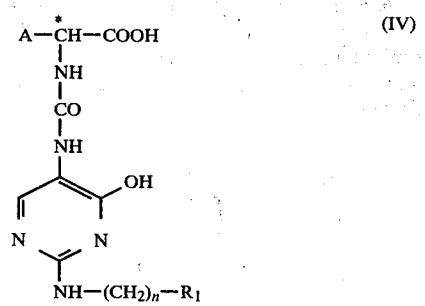

wherein
A, n and $R_1$ have the meanings previously defined, or a salt or reactive derivative thereof, with a compound of the formula

wherein
X has the meanings previously defined.

Suitable reactive derivatives of the ureidocarboxylic acids of the formula IV include, for example, their acid anhydrides such as those derived from chloroformates, for instance ethyl or isobutyl chloroformate, or their reactive esters such as the p-nitrophenyl ester or the N-hydroxysuccinimide ester, or their reactive amides such as the N-carbonyl-imidazole, but also their acid halides such as the corresponding acid chloride or their acid azides.

In general, however, all methods of bonding which are known in $\beta$-lactam chemistry can be used.

The compound of the formula V is advantageously reacted in the form of an in vitro or in vivo easily cleavable derivative. For example, the compounds of the formula V wherein E has the above-mentioned meanings, with the exception of hydrogen, are suitable; especially preferred derivatives are the diphenylmethyl ester, the tert. butyl ester, the trimethylsilyl ester or the N,O-bis-trimethylsilyl derivative.

For example, the ureidocarboxylic acid or a salt or reactive derivative thereof is reacted with the compound of the formula V in a solvent at temperatures between −40° C. and +40° C., optionally in the presence of a base. If, for example, an anhydride of the ureidocarboxylic acid, such as the anhydride with ethylchloroformate, is used, the reaction is carried out while cooling, for instance at −10° C. to +10° C., in the presence of a tertiary amine such as triethylamine or N,N-dimethylaniline, in a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a compound of the formula V, the reaction is preferably carried out at 0° to 20° C. in the presence of a base such as triethylamine, in a solvent such as dimethylformamide, dichloromethane, dioxane, or a mixture of such solvents.

The reaction of a ureidocarboxylic acid of the formula IV or a salt thereof with a compound of the formula V is advantageously carried out in the presence of a condensation agent, for instance in the presence of N,N′-dicyclohexylcarbodiimide.

METHOD C

A compound of the formula I wherein D is —S-Het, where Het has the meanings previously defined, pyridinium or aminocarbonylpyridinium, and E is hydrogen, can be prepared by reacting a compound of the formula

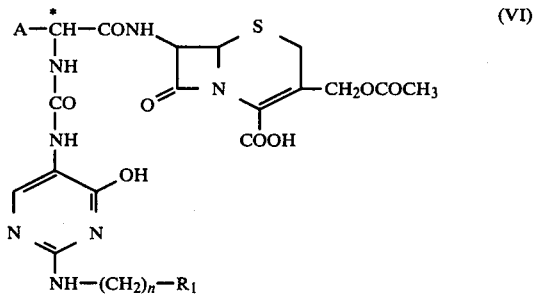

(VI)

wherein
X, n and $R_1$ have the meanings previously defined, either with a compound of the formula

(VII)

wherein
Het has the meanings previously defined, and
M is hydrogen, an alkali metal or an alkaline earth metal,
or with pyridine or 4-amino-carbonyl-pyridine.

For example, a compound of the formula VI is reacted with 5-methyl-2-mercapto-1,3,4-thiadiazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH value can be adjusted by addition of a buffer solution, such as sodium phosphate. The reaction conditions are not subject to special restrictions. Normally, the reaction is carried out at a temperature in a range of 0° to 100° C., over a reaction time of several hours.

The compounds prepared according to methods A, B and C, wherein E is an in vitro easily removable protective group, can be converted according to known methods in cephalosporin and penicillin chemistry into the free carboxylic acids of the formula I wherein E is hydrogen. Thus, the trimethylsilyl group can, for example, be easily removed by aqueous hydrolysis, and the benzhydryl group can be removed, for example, by hydrolytic cleavage with trifluoroacetic acid. This elimination of the protective group is known from the literature.

Moreover, the compounds of the formula I wherein E is hydrogen can be coverted into the acyloxyalkyl esters, wherein E is, for example, a pivaloyloxymethyl radical

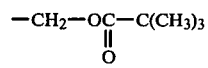

by reacting an alkali metal salt of the free carboxylic acid, for example a sodium or potassium salt, with a pivaloyloxymethyl halide of the formula

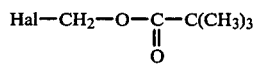

wherein Hal is chlorine, bromine or iodine.

Further suitable acyloxyalkyl halides are, for example, chloromethyl acetate, bromomethyl propionate or 1-bromomethyl acetate.

The preparation of an acyloxyalkyl ester of the formula I is carried out by reacting the respective alkali metal salt of the parent acid in an inert solvent with a slight molar excess of the iodine, bromine or chloroalkyl ester, such as pivaloyloxymethyl iodide, at room temperature or slightly elevated temperature up to about 40° to 45° C. Suitable solvents are, for example, acetone, tetrahydrofuran, dioxane, dimethylformamide or methylene chloride.

After the reaction has gone to completion, the reaction mixture obtained according to methods A-C are further processed by conventional methods for β-lactam antibiotics. The same is the case concerning the isolation and purification of the end products, for instance concerning the liberation of the acid to form other salts with inorganic or organic bases. Especially suitable for the preparation of potassium or sodium salts is the precipitation of these salts from an alcoholic-ethereal solution of a free acid by addition of potassium or sodium 2-ethylhexanoate, or the reaction of a free acid with the corresponding quantity of sodium bicarbonate under pH control and subsequent freeze-drying.

The starting compounds of the formula II, such as ampicillin, amoxycillin, epicillin, cefaloglycine, cefalexin and their esters which are easily clevable in vivo, are known or can be prepared by known methods, for example by acylation of the known amino-lactams of the formula IV and, if desired, subsequent reaction of the cephalosporanic acid derivatives of the formula II (D=-OCOCH₃) thus obtained with thiols of the formula Het-SH.

The starting compounds of the formula III can be obtained, for example, by reacting a corresponding 5-aminopyrimidine of the formula

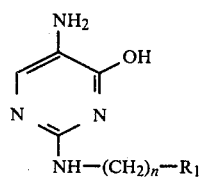

wherein $R_1$ and n have the meanings previously defined, with phosgene. This reaction is preferably carried out in a solvent which does not contain hydroxyl groups, such as tetrahydrofuran, methylene chloride, chloroform, dimethoxyethane or hexametapol, at temperatures between −40° and +60° C., preferably between −10° and +20° C. It is recommended to neutralize the hydrogen chloride released by the reaction with equimolar quantities of an inert organic base, such as triethylamine or pyridine. Also, pyridine in excess can be used as the solvent. If the particular aminopyrimidine of the formula VIII is difficultly soluble in one of the mentioned solvents, the phosgenation can also be carried out in a heterogeneous system. Furthermore, the aminopyrimidine of the formula VIII can be converted by treatment with a silylating agent, such as hexamethyldisilazane, trimethyl chlorosilane/triethylamine, trimethylsilil diethylamine or N,O-bis-trimethylsilyl acetamide, into an aminopyrimidine which, in general, is very easily soluble in the mentioned solvents and which is, depending on the number of exchangeable hydrogen atoms, mono- or polysilylated. After addition of phosgene, the aminopyrimidine reacts therewith to form the corresponding compound of the formula III.

Depending on the kind of solvent, the temperature, the amount and kind of base which is optionally added, either mainly the corresponding isocyanate of the carbamic acid halide or a mixture of these two compounds is obtained. Depending on the reaction conditions, the isocyanate of the formula III can also be present as dihydrooxazolo-pyrimidine of the formula IIIa, this compound being isomeric with the isocyanate

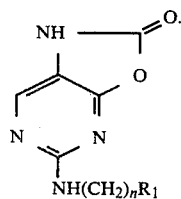

Depending on the type of the substituent -NH(CH₂)ₙR₁, the isocyanate of the formula VI may also be present as a mono- or poly-silylated analog.

The starting compounds of the formula III or IIIa or mixtures thereof or silylated analogs thereof obtained by phosgenation, as described above, are in general readily soluble in the above-mentioned solvents, and after removal of excess phosgene they can be reacted directly, without further purification, with the corresponding β-lactam derivative of the formula II.

However, it is also possible to isolate the intermediate product of the formula IIIa, de-silylate the intermediate, optionally with a protic solvent such as water or methanol, purify it on the basis of its solubility properties, and react it in the manner mentioned above.

The ureidocarboxylic acids of the formula IV can be easily obtained by reacting a pyrimidine derivative of the formula III with a glycine derivative of the formula

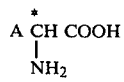

wherein A has the meanings previously defined. The reaction is carried out at temperatures between −20° and +40° C., preferably between 0° and +20° C., in a solvent. Suitable solvents are, for example, mixtures of water and organic solvents which are miscible with water, such as acetone, tetrahydrofuran, dioxane, acetonitrile, dimethylformamide, ethanol or dimethylsulfoxide, optionally in the presence of a hydrogen halide-binding agent. Suitable representatives thereof are, for example, trialkylamines such as triethylamines, or inorganic bases such as dilute sodium hydroxide.

The starting compounds of the formula VI can easily be prepared according to method A.

The 2-substituted-5-amino-4-hydroxy-pyrimidines of the formula VIII can be obtained, for example, by reacting 2-ethylmercapto-4-hydroxy-5-nitro-pyrimidine [Vorbrüggen and Strehlke, Chem. Ber. 106, page 3039 (1973)] with an amine of the formula NH₂(CH₂)ₙ-R₁, where -(CH₂)ₙ-R₁ has the meanings previously defined, and subsequent reduction of the nitro group according to known methods. Instead of the 5-nitro compound, also 2-methylmercapto-4-hydroxy-5-benzoylamino-pyrimidine can be reacted and subsequently debenzoylated; furthermore, the amino pyrimidines of formula VIII can be obtained by reacting 2-chloro-4-hydroxy-5-nitropyrimidine with an amine of the formula R₁(CH₂)ₙNH₂, where R₁(CH₂)ₙ- has the meanings previously defined, in aqueous solution and subsequent reduction of the nitro group.

The following are typical representatives of starting compounds of the formula VIII which can be obtained in the above-described ways:

5-Amino-4-hydroxy-2-(3′-pyridylamino)-pyrimidine,
5-Amino-4-hydroxy-2-(6′-methoxy-3′-pyridylamino)-pyrimidine,
5-Amino-4-hydroxy-2-(2′-pyridylmethylamino)-pyrimidine,
5-Amino-4-hydroxy-2-(3′-pyridylmethylamino)-pyrimidine,
5-Amino-4-hydroxy-2-(4′-pyridylmethylamino)-pyrimidine,
5-Amino-4-hydroxy-2-(5′-pyrimidinylamino)-pyrimidine,
5-Amino-4-hydroxy-2-(2′-amino-5′-pyrimidinylamino)-pyrimidine,
5-Amino-4-hydroxy-2-2′-methyl-5′-pyrimidinylmethylamino)-pyrimidine,
5-Amino-4-hydroxy-2-(2′-methyl-5′-pyrimidinylamino)-pyrimidine,
5-Amino-4-hydroxy-2-(6′-methylsulfinyl-3′-pyridylamino)-pyrimidine,
5-Amino-4-hydroxy-2-(6′-methylsulfonyl-3′-pyridylamino)-pyrimidine, 5-Amino-4-hydroxy-2-(6'-hydroxy-3'-pyridylamino)-pyrimidine,
5-Amino-4-hydroxy-2-(4'-hydroxy-2'-pyrimidinylamino)-pyrimidine,
5-Amino-4-hydroxy-2-(4',6'-dihydroxy-2'-pyrimidinylamino)-pyrimidine,
5-Amino-4-hydroxy-2-(2',6'-dihydroxy-4'-pyrimidinylamino)-pyrimidine,
5-Amino-4-hydroxy-2-(2'-hydroxy-4'-pyrimidinylamino)-pyrimidine,
5-Amino-4-hydroxy-2-(2'-hydroxy-5'-pyrimidinylamino)-pyrimidine,
5-Amino-4-hydroxy-2-(5'-ethoxycarbonyl-2'-thienylamino)-pyrimidine,
5-Amino-4-hydroxy-2-(5'-aminocarbonyl-2'-thienylamino)-pyrimidine,
5-Amino-4-hydroxy-2-(5'-methyl-2'-thienylamino)-pyrimidine,
5-Amino-4-hydroxy-2-(2'-thienylmethylamino)-pyrimidine,
5-Amino-4-hydroxy-2-(3'-thienylmethylamino)-pyrimidine,
5-Amino-4-hydroxy-2-(5'-methyl-2'-thienylmethylamino)-pyrimidine,
5-Amino-4-hydroxy-2-(5'-chloro-2'-thienylmethylamino)-pyrimidine,
5-Amino-4-hydroxy-2-(2'-furylmethylamino)-pyrimidine,
5-Amino-4-hydroxy-2-(3'-furylmethylamino)-pyrimidine,
5-Amino-4-hydroxy-2-(5'-methyl-2'-furylmethylamino)-pyrimidine,
5-Amino-4-hydroxy-2-(2'-tetrahydrofurylmethylamino)-pyrimidine,
5-Amino-2-hydroxy-2-(2'-pyrrolylmethylamino)-pyrimidine,
5-Amino-4-hydroxy-2-(4'-imidazolylmethylamino)-pyrimidine,
5-Amino-4-hydroxy-2-(4'-methyl-2'-thiazolylamino)-pyrimidine,
5-Amino-4-hydroxy-2-(4'-methyl-2'-thiazolylmethylamino)-pyrimidine,
5-Amino-4-hydroxy-2-(5'-methyl-2'-thiadiazolylamino)-pyrimidine,
5-Amino-4-hydroxy-2-(2'-triazolylmethylamino)-pyrimidine,
5-Amino-4-hydroxy-2-(5'-aminosulfonyl-2'-thienylmethylamino)-pyrimidine, and
5-Amino-4-hydroxy-2-(5'-tetrazolylmethylamino)-pyrimidine.

The following examples illustrate the present invention and will enable others skilled in the art to understand it more completely. It should be understood, however, that the invention is not limited solely to the particular examples given below.

I. Preparation of starting compounds

EXAMPLE 1

Aminopyrimidines of the formula VIII.

(a) 5-Amino-4-hydroxy-2-(2'-thienylmethylamino)-pyrimidine

A suspension of 10.5 gm (0.05 mol) of 2-ethylmercapto-4-hydroxy-5-nitro-pyrimidine and 5.65 gm (0.05 mol) of 2-thienylmethylamine in 250 ml of n-propanol was heated for 8 hours at 100° C. After cooling, the precipitated solid product was filtered off with suction and washed first with a little ice-cold propanol and then with ether. A thin-layer chromatogram (silicagel, dichloromethane/methanol 10:1) showed that the starting compound had completely reacted.

Yield: 11.90 gm (94%).

2.72 gm (0.01 mol) of the nitro compound thus obtained were suspended in 40 ml of water, the suspension was admixed with 10 ml of concentrated ammonia, and 7.7 gm (0.05 mol) of sodium dithionite were added in portions while stirring. Subsequently, the mixture was heated for 30 minutes on a steam bath. A thin-layer chromatogram of the resulting aqueous solution (silicagel), dichloromethane/methanol (10:1) showed that no more starting compound was present. The mixture was evaporated to dryness in vacuo, the residual solid product was extracted several times with altogether 300 ml of tetrahydrofuran, and the solvent was removed from the combined extracts in vacuo. 1.65 gm (74%) of the desired compound were thus obtained. M.p.: 66°-68° C.

Calculated: C-48.63%; H-4.53%; N-25.21%. Found: C-48.47%; H-4.51%; N-24.99%.

(b) 5-Amino-4-hydroxy-2-(2'-thiazolylamino)-pyrimidine 4.02 gm (0.02 mol) of 2-ethylmercapto-4-hydroxy-5-nitro-pyrimidine were reacted with 2.0 gm of 2-amino thiazole as in (a). The reaction time was 24 hours. 3.75 gm (79%) of the nitro compound were obtained, which was dissolved without further purification in 150 ml of dimethylformamide and hydrogenated at 50° C. under normal pressure in the presence of 2 gm of palladium/charcoal (5%) until absorption of the calculated amount of hydrogen. The solvent was removed in vacuo, and the residue was extracted with ethanol. After the extraction 2.75 gm (84%) of the desired compound were obtained. M.p.: 300° C.

Calculated: C-40.18%; H-3.37%; N-33.47%. Found: C-40.00%; H-3.37%; N-32.80%.

(c) 5-Amino-4-hydroxy-2-(2'-thienylmethyl-amino)-pyrimidine

The compound obtained in (a) was also synthesized in the following way:

169.5 gm of aminomethylthiophene (1.5 mol) and 93 gm of glacial acetic acid were admixed. The resulting powder was pulverized in a mortar, and 130.5 gm (0.5 mol) of 2-methylmercapto-4-hydroxy-5-benzylamino-pyrimidine were added thereto. The resulting mixture was heated, while stirring, at 180° C. for 6 hours in a 1-liter flask.

The resulting mixture was stirred twice with 0.5 liters of warm ethyl alcohol, and the residual solid product was suction-filtered off and washed with 150 ml of acetoce.

Yield: 120 gm. M.p.: 275° C. (recrystallized from dimethylformamide).

Calculated: C-58.88%; H-4.32%; N-17.17%. Found: C-59.00%; H-4.39%; N-17.21%.

3.26 gm (0.01 mol) of the product thus obtained were refluxed for 3 hours with 4 gm of sodium hydroxide, 0.2 gm of sodium sulfite and 20 ml of water. The mixture was cooled and acidified to pH 0.5 with concentrated hydrochloric acid, and the precipitated benzoic acid was removed by shaking with ether. The aqueous phase was adjusted to pH 6.9 with sodium hydroxide while cooling, and the precipitated product was extracted.

Yield: 1.9 gm (85%).

(d) 2-Chloro-4-hydroxy-5-nitro-pyrimidine sodium monohydrate

A solution of 8.2 gm (0.1 mol) of sodium acetate in 25 ml of water and 10 ml of glacial acetic acid was added dropwise, while stirring, to a solution of 9.7 gm (0.05 mol) of 2,4-dichloro-5-nitropyrimidine at 10° C. After complete addition of the buffer solution, stirring was continued for another hour while cooling on an ice bath. The precipitated thick precipitate was suction-filtered off and dried in vacuo over calcium chloride. 2-Chloro-4-hydroxy-5-nitro-pyrimidine was obtained in the form of its sodium salt with 1 molecule of water of crystallization.

Yield: 10.20 gm (94.4%).

M.p.: None; separation of water beginning at 150° C., decomposition beginning at 195° C.

Calculated: C-22.29%; H-1.40%; Cl-16.45%; N-19.50%. Found: C-22.42%; H-1.50%; Cl-16.46%; N-19.84%.

Water content (according Karl Fischer):
Calculated: 8.36%
Found: 8.4%.

(e) 4-Hydroxy-2-(2'-methyl-5'-pyrimidinylmethylamino)-5-nitro-pyrimidine

A solution of 0.75 gm (0.0061 mol) of 2-methyl-5-methylamino-pyrimidine in 15 ml of dioxane was added to a solution of 1.4 gm (0.0065 mol) of the sodium monohydrate salt of 2-chloro-4-hydroxy-5-nitro-pyrimidine in 20 ml of water, whereby a homogeneous solution was obtained. This solution was refluxed for 2.5 hours. The precipitated reaction product was suction-filtered off, washed with water and dried in vacuo at 50° to 100° C.

Yield: 1.05 gm (65.6%).

M.p.: 244°–246° C. (decomp.)

Calculated: C-45.80%; H-3.84%; N-32.04%. Found: C-45.33%; H-4.02%; N-32.03%.

(f) 5-Amino-4-hydroxy-2-(2'-methyl-5'-pyrimidinylmethylamino)-pyrimidine 1.0 gm of the nitro-pyrimidine obtained in (e) was hydrogenated at normal pressure and room temperature in a hydrogenation vessel in the presence of 0.5 gm of palladium/charcoal (10%), 80 ml of methanol, 10 ml of water and 5 ml of concentrated hydrochloric acid. After the absorption of hydrogen was complete, the catalyst was removed by filtration, the methanol was removed in vacuo, and a little water was added. The pH was adjusted to 4.5 with sodium hydroxide, and the precipitated product was suction-filtered.

Yield: 720 mgm

Decomposition: >250° C.

Using procedures analogous to those described above, the following novel 4-hydroxy-5-amino-pyrimidines of the formula

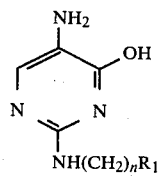

were also prepared:

|  | $(CH_2)_nR_1$ | Yield | M.p. |
|---|---|---|---|
| (g) | 3'-Pyridyl | 62% | >300° C. |
| (h) | 6'-Methoxy-3'-pyridyl | 44% | >300° C. |
| (k) | 2'-Pyridylmethyl | 57% | sinters beginning at 110° C. |
| (l) | 3'-Pyridylmethyl | 84% | 150° C. |
| (m) | 5'-Pyrimidinyl | 34% | 166–170° C. |
| (n) | 2'-Amino-5'-pyrimidinyl | 71% | >200° C. (decomposition) |
| (o) | 2'-Propylamino-5'-pyrimidinyl | 36% | Decomposition >210° C. |
| (p) | 5'-Ethoxycarbonyl-2'-thienyl | 64% | 175° C. |
| (q) | 5'-Methyl-2'-thienyl | 52.5% | 120–123° C. |
| (r) | 3'-Thienylmethyl | 64% | 90–94% |
| (s) | 5'-Chloro-2'-thienylmethyl | 43% | 86° C. |
| (t) | 2'-Furylmethyl | 61% | sinters beginning at ~100° C. |
| (u) | 3'-Furylmethyl | 48% | Decomposition >120° C. |
| (v) | 5'-Methyl-2'-furylmethyl | 52% | Decomposition >130° C. |
| (w) | 2'-Tetrahydrofurylmethyl | 46% | sinters beginning at ~80° C. |
| (x) | 2'-Pyrrolylmethyl | 53% |  |
| (y) | 2'-Imidazolylmethyl | 48% |  |
| (z) | 4'-Methyl-2'-thiazolylmethyl | 66% | sinters beginning at ~90° C. |
| (aa) | 4'-Oxazolylmethyl | 60% | 110–120° C. |
| (ab) | 5'-Methyl-2'-thiadiazolyl | 57.5% | Decomposition >250° C. |
| (ac) | 5'-Methyl-2'-triazolylmethyl | 41% | Decomposition >110° C. |
| (ad) | 5'-Methyl-2'-triazolyl | 49% | Decomposition >250° C. |
| (ae) | 4'-Pyridylmethyl- | 52% | ~175° C. decomposition |
| (af) | 4'-Pyrimidinylmethyl- | 35% | 213° C. |
| (ag) | 5'-Methyl-2'-thienylmethyl | 66% | ~80° C. |
| (ah) | 2'-Pyridyl | 42% | 245–248° C. |
| (ai) | 6'-Hydroxy-3'-pyridyl | 46% | >300° C. |
| (ak) | 6'-Hydroxy-2'-pyridyl | 27% | >300° C. |
| (al) | 2'-Hydroxy-5'-pyrimidinyl | 45% | >300° C. |
| (am) | 2'-Cyclopropyl-4'-hydroxy-5'-pyrimidinyl | 41% | Decomposition >220° C. |
| (an) | 2'-Methyl-5'-pyrimidinyl | 38% | 244° C. |
| (ao) | 5'-Aminocarbonyl-2'-thienyl | 22% | Decomposition >110° C. |
| (ap) | 5'-Tetrazolylmethyl | 41.5% | Decomposition >270° C. |
| (aq) | 2',4'-Dihydroxy-5'-pyrimidinyl | 58% | Decomposition >300° C. |
| (ar) | 4',6'-Dihydroxy-2'-pyrimidinyl | 47% | Decomposition 300° C. |
| (as) | 2',6'-Dihydroxy-4'-pyrimidinyl | 44.5% | Decomposition >300° C. |

(at) 4-Hydroxy-2-(6'-methylsulfinyl-3'-pyridylamino)-5-nitro-pyrimidine 4.68 gm (0.03 mol) of 2-mercapto-5-nitro-pyridine were dissolved, while gently heating, in a sodium hydroxide solution prepared by dissolving 1.32 gm (0.033 mol) of sodium hydroxide in 60 ml of water. 4.17 gm (0.033 mol) of dimethylsulfate were added to this solution, and the mixture was shaken well. The resulting precipitate was filtered off with suction, and the still moist product was recrystallized from ethanol. 2-Methylthio-5-nitro-pyridine was obtained.

Yield: 4.5 gm (88.1%). M.p.: 111°–112° C.

4.5 gm (0.0264 mol) of 2-methylthio-5-nitro-pyridine were hydrogenated at 50° C. and 5 bars pressure in ethanol in the presence of Raney nickel as the catalyst. After the catalyst had been filtered off and after evaporation of the filtrate in vacuo an oil was obtained. A solution of 6.84 gm (0.032 mol) of the sodium monohydrate salt of 2-chloro-4-hydroxy-5-nitro pyrimidine in 150 ml of water was added to the solution of this oil in water. The aqueous solution was heated for 30 minutes on a steam bath, and the resulting precipitate suction-filtered off, washed with water and dried. 4-Hydroxy-2-(6'-methylmercapto-3-pyridyl)amino-5-nitro-pyrimidine was obtained.

Yield: 7 gm (94.8%). M.p.: 295° C. (decomp.).

For analysis, the compound was dissolved in dimethylsulfoxide and reprecipitated with methanol.

Calculated: C-43.00%; H-3.25%; N-25.08%. Found: C-43.09%; H-3.36%; N-24.90%.

5.59 gm (0.02 mol) of 4-hydroxy-2-(6'-methylmercapto-3-pyridylamino)-5-nitro-pyrimidine were dissolved in 20 ml of formic acid, and 1.87 gm (0.022 mol) of 40% perhydrol were added to the solution. After standing for 3 hours at room temperature a precipitate was obtained which was completed by the addition of acetone.

Yield: 5.4 gm (91%). M.p.: >300° C.

Calculated: C-40.67%; H-3.07%; N-23.72% Found: C-40.36%; H-3.06%; N-23.50%.

(au) 5-Amino-4-hydroxy-2-(6'-methylsulfinyl-3'-pyridylamino)-pyrimidine

The reaction was performed with dithionite according to the procedure specified in Example 1(a).

Yield: 56%.

IR-spectrum: 1660, 1020cm$^{-1}$; NMR-spectrum (CDCl$_3$/CD$_3$OD) signal at ppm: 2.9 (s, 3H), 7.3 (s,1H), 7.85 and 8.4 (m,2H), 8.8 (d,1H).

(av) 4-Hydroxy-2-(6-methylsulfonyl-3-pyridylamino)-5-nitropyrimidine

This 4-hydroxy-5-nitro-pyrimidine was prepared analogous to Example 1 (au). An excess of perhydrol was used, and the reaction time was extended to 5 days.

Yield: 72.5%. M.p.: 300° C.

The product still contained small amounts of the methylsulfinyl compound. This impurity was removed by means of solumn chromatography after the reduction of the nitro group.

(aw) 5-Amino-4-hydroxy-2-(6'-methylsulfonyl-3'-pyridylamino)-pyrimidine

The reduction was performed with dithionite according to Example 1(a). Yield: 33%.

IR-spectrum: 1670, 1150, 1355 cm$^{-1}$; NMR-spectrum (DMSO/CD$_3$OD) signals at ppm: 3.1 (s, 3H), 7.15 (s, 1H), 7.9 and 8.4 (m, 2H), 8.8 (d, 1H).

(ax) 5-Amino-4-hydroxy-2-(5'-sulfonamino-2'-thienylmethylamino)-pyrimidine 4 gm (0.0123 mol) of 5-benzoylamino-4-hydroxy-2-(2'-thienylmethylamino)-pyrimidine were added, while cooling, in portions to 14.32 gm (0.12 mol) of chlorosulfonic acid. The resulting solution was stirred for 1.5 hours at room temperature, and the excess chlorosulfonic acid was subsequently decomposed by pouring the solution into ice water. The precipitated 5-benzoylamino-4-hydroxy-2-(5'-chlorosulfonyl-2'-thienylmethylamino)-pyrimidine was suction-filtered off and dried in vacuo over phosphorus pentoxide.

Yield: 4.6 gm (88.5%).

IR-spectrum: 1170, 1370 cm$^{-1}$; NMR-spectrum (DMSO/CD$_3$OD) signals at ppm: 4.8 (s,2H), 7.1 (dd,2H), 7.5 (m,3H), 7.9 (m,2H), 8.4 (s,1H).

4.6 gm (0.0108 mol) of 5-benzoylamino-4-hydroxy-2-(5'-chlorosulfonyl-2'-thienylmethylamino)-pyrimidine were suspended in 100 ml of acetone, and 10 ml of a concentrated aqueous ammonia solution were added to the suspension. The mixture was heated for 10 minutes on a steam bath during which everything went into solution. The solution was evaporated to dryness in vacuo, and the residue was triturated with water and suction-filtered. The residue was suspended in 30 ml of water, 2 gm of sodium hydroxide were added to the suspension, and the mixture was refluxed for 4 hours. The resulting solution was diluted with water, treated with activated charcoal, filtered, adjusted to pH 7 with 2 N hydrochloric acid and left to stand overnight. The precipitate which had formed was suction-filtered off and recrystallized from water.

Yield: 0.85 gm (26.1%).

IR-spectrum: 1150, 1340 cm$^{-1}$; NMR-spectrum (DMSO/CD$_3$OD) signals at ppm: 4.55 (s,2H), 6.95 (d,2H), 7.35 (d,1H).

EXAMPLE II

Preparation of ureidocarboxylic acids of the formula IV (a) D-α-[2-(2'-Furylmethylamino)-4-hydroxy-5-pyrimidinyl]-ureido-phenylacetic acid 2.47 gm of 5-amino-2-(2'-furylmethylamino)-4-hydroxy-pyrimidine (0.012 mol) were dissolved in 80 ml of absolute tetrahydrofuran, and the solution was admixed with 1.65 ml of triethylamine. The resulting solution was added dropwise at 0° C. to a solution of 1.20 gm of phosgene in 25 ml of tetrahydrofuran. The mixture was stirred, while cooling, with ice, for about 10 minutes. Subsequently, nitrogen was blown through the solution to remove unreacted phosgene.

A suspension of 1.8 gm (0.012 mol) of D-α-aminophenylacetic acid in 50 ml of tetrahydrofuran and 20 ml of water was caused to go into solution by the addition of 12 ml of 1N sodium hydroxide while cooling and stirring. The suspension prepared above was added dropwise to this solution while cooling with ice, the pH value being maintained at 8.0 to 8.5 with 1 N sodium hydroxide. The mixture was stirred for one hour at 5° C. and then for two hours at room temperature. The tetrahydrofuran was then removed in vacuo, and the remaining aqueous solution was shaken twice with ethyl acetate at pH 8.0 to 8.5. The aqueous solution was then adjusted to pH 2.9, while cooling and stirring, with dilute hydrochloric acid. The precipitated solid product was suction-filtered off, washed with a little ice-cold water and dried.

Yield: 2.8 gm (70%).

IR-spectrum: 3320 (broad), 1650, 1550 cm$^{-1}$; NMR-spectrum (CDCl$_3$+D$_2$O) signals at ppm: 4.4 (s,2H), 5.15 (s,1H), 6.3 (m,2H), 7.5 (m,6H), 8.1 (s,1H).

(a') D-α-{[2-(2'-Methyl-5'-pyrimidinylmethylamino)-4-hydroxy-5-pyrimidinyl]-ureido}-p-hydroxy phenylacetic acid 2.32 gm of 5-amino-2-(2'-methyl-5'-pyrimidinylmethylamino)-4-hydroxy-pyrimidine (0.01 mol) were suspended in 100 ml of dry tetrahydrofuran, and the suspension was refluxed with 4 ml of trimethylsilyl diethylamine until everything went into solution. The solution was evaporated to dryness in vacuo. The remaining solid product was dissolved in 50 ml of dry tetrahydrofuran, and the solution was added to a solution of 1.05 gm of phosgene in 40 ml of tetrahydrofuran while cooling with ice. After removal of the excess phosgene, the reaction was continued analogous to Example I with 1.65 gm of p-hydroxyphenylacetic acid.

Yield: 2.78 gm (66%). IR-spectrum: 3330 (broad), 1650, 1560 cm$^{-1}$; NMR-spectrum (DMSO+CD$_3$OD) signals at ppm: 4.4 (s,2H), 5.05 (s,1H), 6.7 (d,2H), 7.20 (d,2H), 8.05 (s,1H), 8.6 (s,2H).

The following ureidocarboxylic acids of the formula

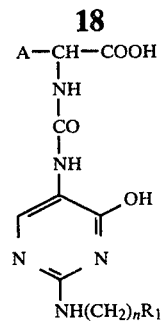

were synthesized in analogous manner:

| | A | $(CH_2)_nR_1$ | Yield % | NMR-Spectrum $(DMSO/CD_3OD)$ |
|---|---|---|---|---|
| (b) | p-HO—Phenyl | 3-Pyridyl | 71 | 5.15 (s,1H), 6.8 (d,2H), 7.25 (d,2H), 7.4 (m,1H), 8.3 (m,3H), 8.8 (broad s,1H) |
| (c) | 2-Furyl | 3-Pyridyl | 66 | 5.5 (s,1H), 6.3 (m,2H), 7.4 (m,1H), 7.6 (s,1H), 8.3 (m,3H), 8.75 (1H) |
| (d) | 2-Thienyl | 3-Pyridyl | 64 | 5.50 (s,1H), 7.0 (m,2H), 7.4 (m,2H), 8.25 (m,3H), 8.8 (broad s,1H) |
| (e) | p-HO—Phenyl | 3-Pyridyl-methyl | 80.5 | 4.5 (broad s,2H), 5.15 (s,1H), 6.8 (d,2H), 7.3 (m,3H), 7.7 (m,1H), 8.1 (s,1H), 8.5 (m,2H) |
| (f) | p-HO—Phenyl | 5-Ethoxycar-bonyl-2-thienyl | 49 | 1.3 (t,3H), 4.3 (q,2H), 5.2 (s,1H), 6.8 (d,2H), 7.3 (d,2H), 7.9 (m,2H) 8.3 (s,1H) |
| (g) | p-HO—Phenyl | 2-Thienylmethyl | 54 | 4.5 (2H), 5.15 (s,1H), 6.6–7.4 (m,7H), 8.1 (s,1H) |
| (h) | p-HO—Phenyl | 5-Methyl-2-thienylmethyl | 70.5 | 2.4 (s,3H), 4.5 (s,2H), 5.15 (s,1H), 6.7 (d,2H), 6.8 (broad s,2H), 7.20 (d,2H), 18 (s,1H) |
| (i) | p-HO—Phenyl | 5-Chloro-2-thienylmethyl | 65 | 4.4 (s,2H), 5.15 (s,1H), 6.7–7.0 (m,4H), 7.25 (d,2H), 8.15 (s,1H) |
| (j) | p-HO—Phenyl | 2-Furylmethyl | 58 | 4.4 (2H), 5.1 (1H), 6.3 (m,2H), 6.7 (d,2H), 7.2 (d,2H), 7.5 (s,1H), 8.05 (s,1H) |
| (k) | m,p-Di-OH—Phenyl | 2-Thienyl-methyl | 62 | 4.5 (s,2H), 5.0 (s,1H), 6.7 (d,1H), 7.0 (m,4H) 7.3 (m,1H) 8.1 (s,1H) |
| (l) | 2-Furyl | 2-Thienyl-methyl | 53 | 4,5 (s,2H), 5.45 (s,1H), 6.4 (m,2H), 7.0 (m,2H) 7.3 (m,1H), 7.6 (s,1H), 8.1 (s,1H) |
| (m) | 2-Thienyl | 2-Thienylmethyl | 57 | 4.5 (s,2H), 5.50 (m,1H), 7.0 (m,4H), 7.25 (m,2H), 8.1 (s,1H) |
| (n) | 2-Furyl | 2-Furylmethyl | 74 | 4.4 (s,2H), 5.5 (s,1H), 6.3 (m,4H), 7.5 (m,2H), 8.1 (s,1H) |
| (o) | 2-Thienyl | 2-Furylmethyl | 56 | 4.4 (s,2H), 5.45 (s,1H), 6.3 (m,2H), 7.0 (m,2H), 7.35 (m,1H), 7.5 (s,1H), 8.1 (s,1H) |
| (p) | p-HO—Phenyl | 5-Methyl-2-furyl-methyl | 77 | 2.5 (s,3H), 4.5 (s,2H), 5.15 (s,1H), 6.3 (m,2H), 6.8 (d,2H), 7.3 (d,2H), 8.1 (s,1H) |
| (q) | p-HO—Phenyl | Tetrahydro-2-furylmethyl | 70 | 1.9 (m,4H), 3.5–4.0 (m,5H), 5.1 (s,1H), 6.7 (d,2H), 7.2 (d,2H), 8.0 (s,1H) |
| (r) | p-HO—Phenyl | 2-Pyrrolylmethyl | 48.5 | 4.3 (broad s,2H), 5.15 (s,1H), 6.1 (s,2H), 6.7 (m,1H + d,2H), 7.3 (d,2H), 8.1 (s,1H), 2.1 (s,3H) |
| (s) | p-HO—Phenyl | 4-Methyl-2-imidazolyl | 51 | 4.4 (s,2H), 5.15 (s,1H), 6.8 (d,2H), 7.2 (m,4H), |

-continued

| | A | $(CH_2)_nR_1$ | Yield % | NMR-Spectrum (DMSO/CD$_3$OD) |
|---|---|---|---|---|
| (t) | p-HO—Phenyl | 4-Methyl-2-thiazolyl | 36.5 | 8.05 (s,1H) 2.1 (s,3H), 5.15 (s,1H), 6.45 (s,1H), 6.85 (d,2H), 7.25 (d,2H), 8.05 (s,1H). |
| (u) | p-HO—Phenyl | 5'-Methyl-2'-thienyl | 44 | 2.5 (s,3H), 5.15 (s,1H), 6.5 (m,2H), 6.8 (d,2H), 7.25 (d,2H), 8.1 (s,1H). |
| (v) | p-HO—Phenyl | 6-Methylsulfinyl-3-pyridyl | 52 | 2.7 (s,3H), 5.15 (s,1H), 6.70 (d,2H), 7.2 (d,2H), 7.7 (d,1H), 8.25 (s,1H), 8.5 (m,1H), 8.9 (s,1H). |
| (w) | 2-Furyl | 6-Methylsulfinyl-3-pyridyl | 60 | 2.73 (s,3H), 5.45 (s,1H), 6.4 (m,2H), 7.4 (m,1H), 7.7 (d,1H), 8.25 (s,1H), 8.5 (m,1H), 8.9 (s,1H). |
| (x) | 2-Thienyl | 6-Methylsulfinyl | 64 | 2.75 (s,3H), 5.50 (s,1H), 7.0 (m,2H), 7.4 (m,1H), 7.7 (d,1H), 8.25 (s,1H), 8.5 (m,1H), 8.85 (s,1H). |
| (y) | p-HO—Phenyl | 6-Methylsulfonyl-3-pyridyl | 62 | 3.1 (s,3H), 5.1 (s,1H), 6.75 (d,2H), 7.2 (d,2H), 7.9 (d,1H), 8.25 (s,1H), 8.6 (d,1H), 8.9 (s,1H). |
| (z) | p-HO—Phenyl | 6-Hydroxy-3-pyridyl | 51 | 5.05 (s,1H), 6.45 (d,1H), 6.75 (d,2H), 7.25 (d,2H), 7.6 (d,1H), 7.9 (s,1H), 8.15 (s,1H). |
| (aa) | 2-Furyl | 3-Pyridylmethyl | 56.5 | 4.5 (broad s,2H), 5.5 (s,1H), 6.3 (m,2H), 7.3 (m,1H), 7.4 (m,1H), 7.7 (m,1H), 8.1 (s,1H), 8.5 (m,2H). |
| (ab) | 2-Thienyl | 3-Pyridylmethyl | 62 | 4.45 (broad s,2H), 5.50 (s,1H), 7.0 (m,2H), 7.3 (m,1H), 7.4 (m,1H), 7.65 (m,1H), 8.05 (s,1H), 8.45 (m,2H). |
| (ac) | p-HO—Phenyl | 2-Methyl-5-pyrimidinyl | 59 | 2.5 (s,3H), 5.15 (s,1H), 6.75 (d,2H), 7.25 (d,2H), 8.3 (s,1H), 9.1 (s,2H). |
| (ad) | p-HO—Phenyl | 5-Amino-sulfonyl-2-thienylmethyl | 53.5 | 4.6 (s,2H), 5.10 (s,1H), 6.7 (d,2H), 6.9 (d,1H), 7.2 (d,2H), 7.4 (d,1H), 8.05 (s,1H). |
| (ae) | 2-Thienyl | 5-Amino-sulfonyl-2-thienylmethyl | 61.5 | 4.55 (s,2H), 5.50 (s,1H), 7.0 (m,3H), 7.4 (m,2H), 8.05 (s,1H). |
| (af) | p-HO—Phenyl | 5-Aminocarbonyl-2-thienyl | 44 | 5.15 (s,1H), 6.6 (d,1H), 6.75 (d,2H), 7.25 (d,2H), 7.45 (d,1H), 8.40 (s,1H). |
| (ag) | 2-Thienyl | 5-Aminocarbonyl-2-thienyl | 49.5 | 5.45 (s,1H), 6.6 (d,1H), 7.0 (m,2H), 7.4 (m,1 + 1H), 8.35 (s,1H). |
| (ah) | p-HO—Phenyl | 2-Hydroxy-5-pyrimidinyl | 64 | 5.15 (s,1H), 6.80 (d,2H), 7.25 (d,2H), 8.35 (1H), 8.75 (s,2H). |
| (ai) | p-HO—Phenyl | 2,4-Dihydroxy-5-pyrimidinyl | 46.5 | 5.15 (s,1H), 6.75 (d,2H), 7.25 (d,2H), 8.35 (s,1H), 8.55 (s,1H). |
| (ak) | p-HO—Phenyl | 2,6-Dihydroxy-4-pyrimidinyl | 58 | 5.10 (s,1H), 6.75 (d,2H), 7.25 (d,2H), 8.35 (s,1H), 8.45 (s,1H). |
| (al) | p-HO—Phenyl | 4,6-Dihydroxy-2-pyrimidinyl | 53.5 | 5.15 (s,1H), 6.75 (d,2H), 7.30 (d,2H), 8.30 (s,1H), 8.80 (s,1H). |

II. Preparation of penicillins of the formula I or I'

Example 1

D-α-{3-[4-Hydroxy-2-(3'-pyridylamino)-5-pyrimidinyl]-ureido}-p-hydroxybenzyl-penicillin sodium 1.02 mgm of 5-amino-4-hydroxy-2-(3'-pyridylamino)-pyrimidine (0.005 mol) were dissolved in absolute tetrahydrofuran, and the solution was admixed with 500 mgm of triethylamine. The resulting solution was added at 0° C. to a solution of 500 mgm of phosgene in 30 ml of absolute tetrahydrofuran. The mixture was stirred for about 30 minutes while cooling wit ice. Subsequently, nitrogen was blown through the suspension to remove unreacted phosgene.

2.1 gm of amoxicillin trihydrate (0.005 mol) were suspended in 80 ml of aqueous 80% tetrahydrofuran and cooled to 0° C. Enough triethylamine was then added to obtain a solution. The suspension prepared above is added thereto over a period of 5 minutes, the pH being maintained at 7.5 with triethylamine. Another 30 ml of water were added, and the reaction mixture was maintained for one hour at 0° to 2° C. Cooling was then stopped, and the mixture was stirred for one hour at room temperature.

40 ml of water were then added, and the tetrahydrofuran was removed in vacuo. The residual aqueous phase was washed twice with 50 ml of ethylacetate. 2 N hydrochloric acid was then added dropwise to the aqueous solution, while stirring, until the pH was 2.9, the temperature being kept below 5° C. The precipitated product was suction-filtered off and dried in a desiccator. A solution of 700 mg of sodium hexanoate in 25 ml of methanol was added to the solid product, and the resulting solution was admixed with ether. The precipitated sodium salt was suction-filtered off and dried in vacuo.

Yield: 2.19 gm of the sodium salt (71%).
IR-spectrum: 1770, 1660, 1610, 1545 cm$^{-1}$;
NMR-spectrum (DMSO+CD$_3$OD) signals at ppm: 1.55 (d,6H), 4.05 (1H), 5.45 (q,2H+s,1H), 6.8 (d,2H), 7.25 (d,2H), 7.4 (m,1H), 8.2 (m,3H), 8.8 (s,1H).

EXAMPLE 2

D-α-{3-[4-Hydroxy-2-(3'-pyridylamino)-5-pyrimidinyl]-ureido}-benzyl-penicillin sodium This penicillin was prepared analogous to Example 1, starting from 2.25 gm of ampicillin sodium (0.006 mol) and the reaction product of 1.22 gm of 5-amino-4-hydroxy-2-(3'-pyridylamino)-pyrimidine with 600 mg of phosgene and 0.82 ml of triethylamine.

Yield: 2.13 gm of the sodium salt (57.5%);
IR-spectrum: 1765, 1650, 1615, 1545 cm$^{-1}$;
NMR-Spectrum (DMSO+CD$_3$OD) signals at ppm: 1.55 (d,6H), 4.05 (s,1H), 5.50 (q,2H+s,1H), 7.4 (m,6H), 8.2 (m,3H), 8.8 (s,1H).

EXAMPLE 3

D-α-{3-[4-Hydroxy-2-(6'-methoxy-3'-pyridylamino)-5-pyrimidinyl]-ureido}-p-hydroxy-benzyl-penicillin sodium This penicillin was prepared analogous to Example 1, starting from 840 mgm of amoxicillin trihydrate (0.002 mol) and the reaction product of 470 mgm (0.002 mol) of 5-amino-4-hydroxy-2-(6-methoxy-3'-pyridylamino)-pyrimidine with 200 mgm of phosgene and 0.27 ml of triethylamine.

Yield: 630 mgm of the sodium salt (48%);
IR-Spectrum: 1770, 1650, 1615, 1550 cm$^{-1}$;
NMR-Spectrum (CD$_3$OD) signals at ppm: 1.6 (d,6H), 3.9 (s,3H), 4.2 (s,1H), 5.4 (m,3H), 6.8 (m,3H), 7.2 (m,2H), 7.7–8.3 (m,3H).

EXAMPLE 4

D-α-{3-[4-Hydroxy-2-(2'-pyridylmethylamino)-5-pyrimidinyl]ureido}-p-hydroxy-benzyl-penicillin sodium This penicillin was prepared analogous to Example 1, starting from 4.2 gm of amoxicillin trihydrate (0.01 mol) and the reaction product of 2.17 gm of 5-amino-4-hydroxy-2-(2'-pyridylmethylamino)-pyrimidine (0.01 mol) with 1.05 gm of phosgene and 1.35 ml of triethylamine.

Yield: 4.06 gm of the sodium salt (64%);
IR-Spectrum: 1765, 1650, 1615, 1545 cm$^{-1}$;
NMR-Spectrum (DMSO+CD$_3$OD) signals at ppm: 1.55 (d,6H), 3.9 (s,1H), 4.6 (s,2H), 5.45 (q,2H+s,1H), 6.85 (d,2H), 7.35 (m,4H), 7.85 (m,1H), 8.2 (s,1H), 8.7 (m,1H).

EXAMPLE 5

D-α-{3-[4-Hydroxy-2-(3'-pyridylmethylamino)-5-pyrimidinyl]-ureido}-p-hydroxy-benzyl-penicillin sodium This penicillin was prepared analogous to Example 1, starting from 2.1 gm of amoxicillin trihydrate (0.005 mol) and the reaction product of 1.19 gm (0.005 mol) of 5-amino-4-hydroxy-2-(3'-pyridyl-methylamino)-pyrimidine with 500 mgm of phosgene and 0.67 ml of triethylamine.

Yield: 2.45 gm of the sodium salt (79%);
IR-Spectrum: 1765, 1640, 1610, 1560 cm$^{-1}$;
NMR-Spectrum (DMSO+CD$_3$OD) signals at ppm: 1.5 (d,6H), 3.9 (s,1H), 4.55 (s,2H), 5.35 (m,3H), 6.75 (d,2H), 7.2 (m,3H), 7.6 (m,1H), 8.0 (s,1H), 8.3 (m,2H).

EXAMPLE 6

D-α-{3-[4-Hydroxy-2-(4'-pyridylmethylamino)-5-pyrimidinyl]-ureido}-p-hydroxy-benzyl-penicillin sodium This penicillin was prepared analogous to Example 1, starting from 420 mgm amoxicillin trihydrate (0.001 mol) and the reaction product of 220 mgm of 5-amino-4-hydroxy-2-(4'-pyridylmethylamino)-pyrimidine with 100 mgm of phosgene and 0.14 ml of triethylamine.

Yield: 310 mgm of the sodium salt (50%);
IR-Spectrum: 1770, 1650, 1615, 1545 cm$^{-1}$;
NMR-Spectrum (DMSO+CD$_3$OD) signals at ppm: 1.5 (d,6H), 3.9 (s,1H), 4.5 (broad s,2H), 5.4 (q,2H+s,1H), 6.7 (d,2H), 7.2 (m,4H), 8.0 (s,1H), 8.4 (m,2H).

EXAMPLE 7

D-α-{3-(4-Hydroxy-2-(5'-pyrimidinylamino)-5-pyrimidinyl]-ureido}-p-hydroxy-benzyl-penicillin sodium 410 mgm (0.002 mol) of 5-amino-4-hydroxy-2-(5'-pyrimidinylamino)-pyrimidine were heated at 80° C. with 5 ml of trimethylsilyldiethylamine. A homogeneous mixture was obtained which was evaporated to dryness in a high vacuum. The residue was dissolved in 40 ml of dry tetrahydrofuran, and this solution was added to a solution of 200 mg of phosgene in 30 ml of tetrahydrofuran while cooling with ice. The further reaction is carried out analogous to Example 1.

Yield: 735 mgm of the sodium salt (64%);
IR-Spectrum: 1765, 1655, 1615, 1550 cm$^{-1}$;
NMR-Spectrum (DMSO+CD$_3$OD) signals at ppm: 1.55 (d,6H), 3.95 (s,1H), 5.40 (q,2H+1,1H), 6.8 (d,2H), 7.3 (d,2H), 8.3 (s,1H), 8.6 (broad s,2H), 8.9 (s,1H).

The following penicillins were synthesized analogously:

D-α-{3-[4-Hydroxy-2-(5'-pyrimidinylamino)-5-pyrimidyl]-ureido}-benzyl-penicillin sodium D-α-{3-[4-Hydroxy-2-(1',2',3',4'-tetrahydro-1',3'-dimethyl-2,',4'-dioxo- -5'-pyrimidinyl)-5-pyrimidinyl]-ureido}-p-hydroxy-benzyl-penicillin sodium.

EXAMPLE 8

D-α-{3-[4-Hydroxy-2-(2'-amino-5'-pyrimidinylamino)-5-pyrimidinyl]-ureido}-p-hydroxybenzyl-penicillin sodium 660 mgm (0.003 mol) of 5-Amino-4-hydroxy-2-(2'-amino-5-pyrimidinyl-amino)-pyrimidine were suspended in 50 ml of absolute tetrahydrofuran, and the suspension was stirred for two hours at room temperature with 2 ml of N,O-bis-trimethylsilyl acetamide. The resulting solution was carefully dried in a water aspirator vacuum and subsequently in high vacuum at 80° C. It was then taken up again in 50 ml of absolute tetrahydrofuran, and this solution is added dropwise, while cooling with ice, to a solution of 300 mgm of phosgene in 20 ml of absolute tetrahydrofuran.

The further reaction is effected with 1.26 gm of amoxicillin (0.003 mol) as described in the preceding examples.

Yield: 645 mgm of the sodium salt (33%);
IR-Spectrum: 1770, 1665, 1615, 1550 cm$^{-1}$;
NMR-Spectrum (DMSO+CD$_3$OD) signals at ppm: 1.55 (6H), 4.0 (1H), 5.40 (q,2H+s,1H), 6.75 (d,2H), 7.3 (d,2H), 8.25 (s,1H), 8.50 (broad s,2H).

EXAMPLE 9

D-α-{3-[4-Hydroxy-2-(5'-ethoxycarbonyl-2'-thienylamino)-5-pyrimidinyl]-ureido}-p-hydroxy-benzyl-penicillin sodium This penicillin was prepared analogous to Example 1, starting from 4.2 gm of amoxicillin trihydrate (0.01 mol) and the reaction product of 2.8 gm of 5-amino-4-hydroxy-2-(5'-ethoxycarbonyl-2'-thienylamino)-pyrimidine with 500 mgm of phosgene and 0.68 ml of triethylamine.

Yield: 4.05 gm of the sodium salt (59.5%);
IR-Spectrum: 1770, 1650, 1620, 1545 cm$^{-1}$;
NMR-Spectrum (DMSO+CD$_3$OD) signals at ppm: 1.3 (t,3H), 1.55 (d,6H), 4.0 (s,1H), 4.3 (q,2H), 5.4 (q,2H+s,1H), 6.8 (s,2H), 7.3 (d,2H), 7.9 (m,2H), 8.3 (s,1H).

EXAMPLE 10

D-α-{3-[4-Hydroxy-2-(2'-thienylmethylamino)-5-pyrimidinyl]-ureido}-p-hydroxy-benzyl-penicillin sodium This penicillin was prepared analogous to Example 1, starting from 8.4 gm of amoxicillin trihydrate (0.02 mol) and the reaction product of 4.48 gm (0.02 mol) of 5-amino-4-hydroxy-2-(2'-thienylmethylamino)-pyrimidine with 2.0 gm of phosgene and 2.75 ml of triethylamine.

Yield: 9.75 gm of the sodium salt (76%);
IR-Spectrum: 1770, 1660, 1620, 1560 cm$^{-1}$;
NMR-Spectrum (DMSO+CD$_3$OD) signals at ppm: 1.55 (d,6H), 4.0 (s,1H), 4.5 (s,2H), 5.35 (q,2+s,1H), 6.7 (d,2H), 6.85 (m,2H), 7.25 (d,2H), 7.35 (m,1H), 8.1 (s,1H).

EXAMPLE 11

D-α-{3-[4-Hydroxy-2-(2'-thienylmethylamino)-5-pyrimidinyl]-ureido}-benzyl-penicillin sodium This penicillin was prepared analogous to Example 1, starting from 1.86 gm of ampicillin sodium (0.005 mol) and the reaction product of 1.12 gm of 5-amino-4-hydroxy-2-(2'-thienylmethylamino)-pyrimidine with 500 mgm of phosgene and 0.68 ml of triethylamine.

Yield: 2.20 gm of the sodium salt (70.5%);
IR-Spectrum: 1765, 1655, 1610, 1545 cm$^{-1}$;
NMR-Spectrum (DMSO+CD$_3$OD) signals at ppm: 1.55 (6H), 4.05 (s,1H), 4.5 (s,2H), 5.4 (q,2+s,1H), 6.85 (m,2H), 7.4 (m,6H), 8.05 (s,1H).

The following penicillins were synthesized analogously: D-α-{3-[4-Hydroxy-2-(2'-thienylmethylamino)-5-pyrimidinyl]-ureido}-m,p-dihydroxy-benzyl-penicillin sodium, D-α-{3-[4-Hydroxy-2-(2'-thienylmethylamino)-5-pyrimidinyl]-ureido}-cyclohexa-1,4-dien-1-yl-methyl-penicillin sodium, D-α-{3-[4-Hydroxy-2-(2'-thienylmethylamino)-5-pyrimidinyl]-ureido}-2-thienylmethyl-penicillin sodium D-α-{3-[4-Hydroxy-2-(2'-thienylmethylamino)-5-pyrimidinyl]-ureido}-2-furylmethyl-penicillin sodium.

EXAMPLE 12

D-α-{3-[4-Hydroxy-2-(3'-thienylmethylamino)-5-pyrimidinyl]-ureido}-p-hydroxy-benzyl-penicillin sodium This penicillin was prepared analogous to Example 1, starting from 840 gm of amoxicillin trihydrate (0.002 mol) and the reaction product of 460 mgm of 5-amino-4-hydroxy-2-(3'-thienylmethylamino)-pyrimidine with 200 mgm of phosgene and 0.27 ml of triethylamine.

Yield: 860 mgm of the sodium salt (66%);
IR-Spectrum: 1765, 1650, 1610, 1545 cm$^{-1}$.

EXAMPLE 13

D-α-{3-[4-Hydroxy-2-(5'-methyl-2'-thienylmethylamino)-5-pyrimidinyl]-ureido}-p-hydroxy-benzyl-penicillin sodium This penicillin was prepared analogous to Example 1, starting from 1.26 gm of amoxicillin trihydrate (0.003 mol) and the reaction product of 700 mgm (0.003 mol) of 5-amino-4-hydroxy-2-(5'-methyl-2'-thienylmethylamino)-pyrimidine with 300 mgm of phosgene and 0.41 ml of triethylamine.

Yield: 380 mgm of the sodium salt (54.5%);
IR-Spectrum: 1770, 1645, 1610, 1550 cm$^{-1}$;
NMR-Spectrum (DMSO+CD$_3$OD) signals at ppm: 1.55 (6H), 2.45 (s,3H), 4.0 (s,1H), 4.5 (s,2H), 5.4 (m,3H), 6.7 (d,2H), 6.85 (2H), 7.20 (d,2H), 8.05 (s,1H).

The following penicillins were synthesized analogously.

D-α-{3-[4-Hydroxy-2-(5'-methyl-2'-thienylmethylamino)-5-pyrimidinyl]-ureido}-benzyl-penicillin sodium, D-α-{3-[4-Hydroxy-2-(5'-methyl-2'-thienylmethylamino)-5-pyrimidinyl]-ureido}-cyclohexa-1,4-dien-1-yl-methyl-penicillin sodium, D-α-{3-[4-Hydroxy-2-(5'-methyl-2'-thienylmethylamino)-5-pyrimidinyl]-ureido}-2-furylmethyl-penicillin sodium.

EXAMPLE 14

D-α-{3-[4-Hydroxy-2-(5'-chloro-2'-thienylmethylamino)-5-pyrimidinyl]-ureido}-p-hydroxy-benzyl-penicillin sodium This penicillin was prepared analogous to Example 1, starting from 1.0 gm of amoxicillin trihydrate (0.0024 mol) and the reaction product of 700 mgm of 5-amino-4-hydroxy-2-(5'-chloro-2'-thienylmethylamino)-pyrimidine with 250 mgm of phosgene and 0.33 ml of triethylamine.

Yield: 1.1 gm of the sodium salt (67%);
IR-Spectrum: 1765, 1655, 1615, 1550 cm$^{-1}$;
NMR-Spectrum (DMSO+CD$_3$OD) signals at ppm: 1.55 (6H), 4.0 (1H), 4.45 (s,2H), 5.35 (q,2H+s,1H), 6.7–7.0 (m,4H), 7.25 (d,2H), 8.10 (s,1H).

EXAMPLE 15

D-α-{3-[4-Hydroxy-2-(2'-furylmethylamino)-5-pyrimidinyl]-ureido}-p-hydroxy-benzyl-penicillin sodium This penicillin was prepared analogous to Example 1, starting from 6.3 gm of amoxicillin trihydrate (0.015 mol) and the reaction product of 3.1 gm (0.015 mol) of 5-amino-4-hydroxy-2-(2'-furylmethylamino)-pyrimidine with 1.5 gm of phosgene and 2.0 ml of triethylamine.

Yield: 6.45 gm of the sodium salt (69%);
IR-Spectrum: 1770, 1660, 1620, 1550 cm$^{-1}$;
NMR-Spectrum (DMSO+CD$_3$OD) signals at ppm: 1.5 (d,6H), 3.9 (s,1H), 4.4 (broad s,2H), 5.4 (q,2H+s,1H), 6.3 (m,2H), 6.7 (d,2H), 7.2 (d,2H), 7.5 (s,1H), 8.0 (s,1H).

EXAMPLE 16

D-α-{3-[4-Hydroxy-2-(2'-furylmethylamino)-5-pyrimidinyl]-ureido}-benzyl-penicillin sodium This penicillin was prepared analogous to Example 1, starting from 1.86 gm of ampicillin sodium (0.005 mol) and the reaction product of 1.06 gm of 5-amino-4-hydroxy-2-(2'-furylmethylamino)-pyrimidine with 500 mgm of phosgene and 0.68 ml of triethylamine.

Yield: 1.91 gm of the sodium salt (62%);
NMR-Spectrum (DMSO+CD$_3$OD) signals at ppm: 1.55 (d,6H), 4.0 (s,1H), 4.4 (broad s,2H), 5.4 (q,2H+s,1H), 6.3 (m,2H), 7.45 (m,6H), 8.05 (s,1H).

The following penicillins were prepared analogously:

D-α-{3-[4-Hydroxy-2-(2'-furylmethylamino)-5-pyrimidinyl]-ureido}-m,p-dihydroxy-benzyl-penicillin sodium;

D-α-{3-[4-Hydroxy-2-(2'-furylmethylamino)-5-pyrimidinyl]-ureido}-cyclohexa-1,4-dien-1-yl-methylpenicillin sodium;

D-α-{3-[4-Hydroxy-2-(2'-furylmethylamino)-5-pyrimidinyl]-ureido}-2-furylmethyl-penicillin sodium;

D-α-{3-[4-Hydroxy-2-(2'-furylmethylamino)-5-pyrimidinyl]-ureido}-3-furylmethyl-penicillin sodium D-α-{3-[4-Hydroxy-2-(2'-furylmethylamino)-5-pyrimidinyl]-ureido}-2-thienylmethyl-penicillin sodium; and D-α-{3-[4-Hydroxy-2-(2'-furylmethylamino)-5-pyrimidinyl]-ureido}-3-thienylmethyl-penicillin sodium.

EXAMPLE 17

D-α-{3-[4-Hydroxy-2-(5'-methyl-2'-thienylamino)-5-pyrimidinyl]-ureido}-p-hydroxy-benzyl-penicillin sodium This penicillin was prepared analogous to Example 1, starting from 500 mgm of amoxicillin trihydrate (0.0012 mol) and the reaction product of 270 mgm of 5-amino-4-hydroxy-2-(5'-methyl-2'-thienylamino)-pyrimidine with 120 mgm of phosgene and 0.17 ml of triethylamine.

Yield: 350 mgm of the sodium salt (47%);
IR-Spectrum: 1765, 1655, 1610, 1550 cm$^{-1}$;
NMR-Spectrum (DMSO+CD$_3$OD) signals at ppm: 1.55 (6H), 2.5 (s,3H), 4.0 (s,1H), 5.35 (q,2H+s,1H), 6.5 (m,2H), 6.75 (d,2H), 7.2 (d,2H), 8.1 (s,1H).

EXAMPLE 18

D-α-{3-[4-Hydroxy-2-(5'-methyl-2'-furylmethylamino)5-pyrimidinyl]-ureido}-p-hydroxy-benzyl-penicillin sodium This penicillin was prepared analogous to Example 1, starting from 840 mgm of amoxicillin trihydrate (0.002 mol) and the reaction product of 440 mgm (0.002 mol) of 5-amino-4-hydroxy-2-(5'-methyl-2'-furylmethylamino)-pyrimidine with 200 mgm of phosgene and 0.27 ml of triethylamine.

Yield: 620 mgm of the sodium salt (48%);
IR-Spectrum: 1770, 1655, 1620, 1550 cm$^{-1}$;
NMR-Spectrum (DMSO+CD$_3$OD) signals at ppm: 1.55 (d,6H), 2.45 (s,3H), 4.0 (s,1H), 5.40 (q,2H+s,1H), 6.3 (m,2H), 6.75 (d,2H), 7.2 (d,2H), 8.05 (s,1H).

EXAMPLE 19

D-α-{3-[4-Hydroxy-2-(tetrahydro-2'-furylmethylamino)-5-pyrimidinyl]-ureido}-p-hydroxy-benzyl-penicillin sodium This penicillin was prepared analogous to Example 1, starting from 4.2 gm of amoxicillin trihydrate (0.01 mol) and the reaction product of 2.1 gm of 5-amino-4-hydroxy-2-(tetrahydro-2'-furylmethylamino)-pyrimidine with 1.0 gm of phosgene and 1.35 ml of triethylamine.

Yield: 3.62 gm of the sodium salt (58%);
IR-Spectrum: 1765, 1650, 1615, 1545 cm$^{-1}$;
NMR-Spectrum (DMSO+CD$_3$OD) signals at ppm: 1.55 (d,6H), 1.9 (m,4H), 3.5–4.0 (m,6H), 5.4 (q,2H+s,1H), 6.7 (d,2H), 7.2 (d,2H), 8.0 (s,1H).

EXAMPLE 20

D-α-{3-[4-Hydroxy-2-(2'-pyrrolylmethylamino)-5-pyrimidinyl]-ureido}-p-hydroxy-benzyl-penicillin sodium This penicillin was prepared analogous to Example 1, starting from 1.0 gm of amoxicillin trihydrate (0.0024 mol) and the reaction product of 490 mgm (0.0024 mol) of 5-amino-4-hydroxy-2-(2'-pyrrolylmethylamino)-pyrimidine with 250 mgm of phosgene and 0.33 ml of triethylamine.

Yield: 635 mgm of sodium salt (42.5%);
IR-Spectrum: 1770, 1650, 1615, 1550 cm$^{-1}$;
NMR-Spectrum (DMSO+CD$_3$OD) signals at ppm: 1.55 (d,6H), 3.95 (s,1H), 4.3 (s,2H), 5.4 (m,3H), 6.1 (m,2H), 6.7 (m,3H), 7.3 (d,2H), 8.05 (s,1H).

EXAMPLE 21

D-α-{3-[4-Hydroxy-2-(2'-thiazolylamino)-5-pyrimidinyl]-ureido}-p-hydroxy-benzyl-penicillin sodium This penicillin was prepared analogous to Example 1, starting from 2.1 gm of amoxicillin trihydrate (0.005 mol) and 1.05 gm of 5-amino-4-hydroxy-2-(2'-thiazolylamino)pyrimidine which was reacted after silylation with 500 mgm of phosgene and 0.68 ml of triethylamine.

Yield: 1.12 gm of the sodium salt (36%);
IR-Spectrum: 1765, 1650, 1610, 1540 cm$^{-1}$;

NMR-Spectrum (DMSO+CD$_3$OD) signals at ppm: 1.55 (6H), 3.95 (s,1H), 5.40 (q,2H+s,1H), 6.7 (m,4H), 7.25 (d,2H), 8.0 (s,1H).

EXAMPLE 22

D-α-{3-[4-Hydroxy-2-(4'-methyl-2'-thiazolylmethylamino)-5-pyrimidinyl]-ureido}-p-hydroxy-benzyl-penicillin sodium This penicillin was prepared analogous to Example 1, starting from 2.0 gm of amoxicillin trihydrate (0.0048 mol) and the reaction product of 1.75 gm of 5-amino-4-hydroxy-2-(4'-methyl-2'-thiazolyl-methylamino)-pyrimidine with 500 mgm of phosgene and 0.65 ml of triethylamine.

Yield: 1.30 gm of the sodium salt (41%);
IR-Spectrum: 1765, 1650, 1615, 1550 cm$^{-1}$;
NMR-Spectrum (DMSO+CD$_3$OD) signals at ppm: 1.55 (d,6H), 2.25 (s,3H), 4.0 (s,1H), 4.4 (broad s,2H), 6.6 (s,1H), 6.75 (d,2H), 7.2 (d,2H), 8.0 (s,1H).

EXAMPLE 23

D-α-{3-[4-Hydroxy-2-(4'-methyl-2'-imidazolylmethylamino)-5-pyrimidinyl]-ureido}-p-hydroxy-benzyl-penicillin sodium This penicillin was prepared analogous to Example 7, starting from 1.5 gm of amoxicillin trihydrate (0.0035 mol) and the reaction product of 730 mgm of 5-amino-4-hydroxy-2-(2'-imidazolylmethylamino)-pyrimidine with trimethylsilyldiethylamine and 350 mgm of phosgene.

Yield: 1.18 gm of the sodium salt (54%);
IR-Spectrum: 1765, 1655, 1615, 1545 cm$^{-1}$;
NMR-Spectrum (DMSO+CD$_3$OD) signals at ppm: 1.55 (d,6H), 2.1 (s,3H), 4.0 (s,1H), 4.4 (s,2H), 5.40 (m,3H), 6.8 (d,2H), 7.2 (m,4H), 8.05 (s,1H).

The following penicillin was synthesized analogously:

D-α-{3-[4-Hydroxy-2-(2'-oxazolylmethylamino)-5-pyrimidinyl]-ureido}-p-hydroxy-benzyl-penicillin sodium.

EXAMPLE 24

D-α-{3-[4-Hydroxy-2-(5'-methyl-1',3',4'-triazol-2'-ylmethylamino)-5-pyrimidinyl]-ureido}-p-hydroxy-benzyl-penicillin sodium This penicillin was prepared analogous to Example 7, starting from 840 mgm of amoxicillin trihydrate (0.002 mol) and the reaction product of 440 mgm (0.002 mol) of 5-amino-4-hydroxy-2-(5'-methyl-1',3',4'-triazol-2'-ylmethylamino)pyrimidine with 200 mgm of phosgene.

Yield: 615 mgm of the sodium salt (47.5%);
IR-Spectrum: 1770, 1660, 1620, 1550 cm$^{-1}$;
NMR-Spectrum (DMSO+CD$_3$OD) signals at ppm: 1.55 (d,6H), 2.15 (s,3H), 3.95 (s,1H), 4.4 (broad s,2H), 5.45 (m,3H), 6.8 (d,2H), 7.25 (d,2H), 8.1 (s,1H).

EXAMPLE 25

D-α-{3-[4-Hydroxy-2-(5'-methyl-1',3',4'-thiadiazol-2'-ylamino)-5-pyrimidinyl]-ureido}-p-hydroxy-benzyl-penicillin sodium This penicillin was prepared analogous to Example 7, starting from 4.2 gm of amoxicillin trihydrate (0.01 mol) and 2.24 gm of 5-amino-4-hydroxy-2-(5'-methyl-1',3',4'-thiadiazol-2'-ylamino)-pyrimidine which was reacted after silylation with 1.0 gm of phosgene.

Yield: 2.4 gm of the sodium salt (33.5%).

IR-Spectrum: 1765, 1655, 1615, 1545 cm$^{-1}$;
NMR-Spectrum (DMSO+CD$_3$OD) signals at ppm: 1.55 (d,6H), 2.4 (s,3H), 4.0 (s,1H), 5.4 (q,2H+s,1H), 6.75 (d,2H), 7.25 (d,2H), 8.1 (s,1H). The following penicillin was synthesized analogously:

D-α-{3-[4-Hydroxy-2-(5'-methyl-1',3',4'-triazol-2'-ylamino)-5-pyrimidinyl]-ureido}-p-hydroxy-benzyl-penicillin sodium.

EXAMPLE 26

D-α-{3-[4-Hydroxy-2-(4'-pyrimidinylmethylamino)-5-pyrimidinyl]-ureido}-p-hydroxy-benzyl-penicillin sodium This penicillin was prepared analogous to Example 7, starting from 840 mgm of amoxicillin trihydrate (0.002 mol) and 420 mgm of 5-amino-4-hydroxy-2-(4'-pyrimidinylmethylamino)-pyrimidine.

Yield: 780 mgm (62%);
IR-Spectrum: 1770, 1650, 1610 1555 cm$^{-1}$;
NMR-Spectrum (DMSO+CD$_3$OD) signals at ppm: 1.5 (d,6H), 3.9 (s,1H), 4.5 (broad s,2H), 5.35 (q,2H+s,1H), 6.7 (d,2H), 7.2 (d,2H), 7.4 (d,1H), 8.0 (s,1H), 8.7 (d,2H), 9.0 (s,1H).

EXAMPLE 27

D-α-{3-[4-Hydroxy-2-(5'-aminosulfonyl-2'-thienylmethylamino)-5-pyrimidinyl]-ureido}-p-hydroxy-benzyl-penicillin sodium This penicillin was prepared analogous to Example 7, starting from 766 mgm of amoxicillin trihydrate (0.00183 mol) and the reaction product of 500 mgm (0.00166 mol) of 5-amino-4-hydroxy-2-(2'-thienylmethylamino)-pyrimidine with 5 ml of N,N-diethyl-trimethylsilylamine and 164 mgm (0.00166 mol) of phosgene.

Yield: 185 mgm of the sodium salt (16%);
IR-Spectrum: 1600, 1660, 1765 cm$^{-1}$;
NMR-Spectrum (DMSO+CD$_3$OD) signals at ppm: 1.5 (d,6H), 4.1 (s,1H), 4.6 (broad s,2H), 5.4 (d,3H), 6.7 (d,2H), 6.9 (d,1H), 7.2 (d,2H), 7.4 (d,1H), 8.05 (s,1H).

EXAMPLE 28

D-α-{3-[4-Hydroxy-2-(2'-methyl-5'-pyrimidinylmethylamino)-5-pyrimidinyl]-ureido}-p-hydroxy-benzyl-penicillin sodium This penicillin was prepared analogous to Example 7, starting from 990 mgm (0.00235 mol) of amoxicillin trihydrate and the reaction product of 500 mgm (0.00215 mol) of 5-amino-4-hydroxy-2-(2'-methyl-5'-pyrimidinylmethylamino)-pyrimidine with 5 ml of N,N-diethyl-trimethylsilylamine and 213 mgm of phosgene.

Yield: 265 mgm of the sodium salt (19%);
IR-Spectrum: 1765, 1660 cm$^{-1}$;
NMR-Spectrum (DMSO+CD$_3$OD) signals at ppm: 1.5 (d,6H), 2.5 (s,3H), 3.95 (s,1H), 4.4 (s,2H), 5.4 (m,3H), 6.7 (d,2H), 7.15 (d,2H), 8.05 (s,1H), 8.6 (s,2H).

EXAMPLE 29

D-α-{3-[4-Hydroxy-2-(2'-pyridylamino)-5-pyrimidinyl]-ureido}-p-hydroxy-benzyl-penicillin sodium This penicillin was prepared analogous to Example 7, starting from 1.85 gm (0.0044 mol) of amoxicillin trihydrate and the reaction product of 0.81 gm (0.004 mol) of 5-amino-4-hydroxy-2-(2'-pyridylamino)-pyrimidine with 10 ml of N,N-diethyl-trimethylsilylamine, 396 mgm of phosgene and 0.56 ml of triethylamine.

Yield: 0.9 gm of the sodium salt (37%);
IR-Spectrum: 1765, 1660, 1600 cm$^{-1}$;
NMR-Spectrum (DMSO+CD$_3$OD) signals at ppm: 1.5 (d,6H), 4.0 (s,1H), 5.4 (m,3H), 6.8 (d,2H), 7.2 (m,4H), 7.7 (m,2H), 8.3 (m,2H).

EXAMPLE 30

D-α-{3-[4-Hydroxy-2-(6'-hydroxy-3'-pyridylamino)-5-pyrimidinyl]-ureido}-p-hydroxy-benzyl-penicillin sodium This penicillin was prepared analogous to Example 7, starting from 0.879 gm (0.0021 mol) of amoxicillin trihydrate and the reaction product of 438 mgm (0.002 mol) of 5-amino-4-hydroxy-2-(6'-hydroxy-3'-pyridylamino)-pyrimidine with 12 ml of N,N-diethyl-trimethylsilylamine and 216 mgm of phosgene.

Yield: 0.311 gm of the sodium salt (25%);
IR-Spectrum: 1765, 1665, 1610 cm$^{-1}$;
NMR-Spectrum (DMSO+CD$_3$OD) signals at ppm: 1.5 (d,6H), 4.1 (s,1H), 5.4 (broad, m,3H), 6.4 (d,1H), 6.75 (d,2H), 7.25 (d,2H), 7.6 (d,1H), 7.9 (s,1H), 8.15 (s,1H).

EXAMPLE 31

D-α-{3-[4-Hydroxy-2-(6'-hydroxy-2'-pyrimidylamino-5-pyrimidinyl]-ureido}-p-hydroxy-benzyl-penicillin sodium This penicillin was prepared analogous to Example 7, starting from 420 mgm of amoxicillin trihydrate (0.001 mol) and the reaction product of 220 mgm (0.001 mol) of 5-amino-4-hydroxy-2-(6'-hydroxy-2'-pyrimidylamino)-pyrimidine with 2 ml of N,N-diethyl-trimethylsilylamine and 100 mgm of phosgene.

Yield: 264 mgm of the sodium salt (42%);
IR-Spectrum: 1765, 1660, 1610, 1020 cm$^{-1}$;
NMR-Spectrum (DMSO+CD$_3$OD) signals at ppm: 1.5 (d,6H), 4.05 (s,1H), 5.35 (q,2H), 5.45 (s,1H), 6.45 (d,1H), 6.75 (d,2H), 7.25 (d,2H), 7.6 (d,1H), 7.9 (s,1H), 8.20 (s,1H).

EXAMPLE 32

D-α-{3-[4-Hydroxy-2-(2'-hydroxy-5'-pyrimidinylamino)-5-pyrimidinyl]-ureido}-p-hydroxy-benzyl-penicillin sodium This penicillin was prepared analogous to Example 7, starting from 800 mgm of amoxicillin trihydrate (0.0019 mol) and the reaction product of 420 mgm (0.0019 mol) of 5-amino-4-hydroxy-2-(2'-hydroxy-5'-pyrimidylamino)-pyrimidine with 4 mol of N,N-diethyl-trimethylsilylamine and 190 mgm of phosgene.

Yield: 550 mgm of the sodium salt (46%);
IR-Spectrum: 1770, 1655, 1610 cm$^{-1}$;
NMR-Spectrum (DMSO+CD$_3$OD) signals at ppm: 1.55 (d,6H), 4.1 (s,1H), 5.45 (m,3H), 6.75 (d,2H), 7.25 (d,2H), 8.35 (s,1H), 8.75 (s,2H).

EXAMPLE 33

D-α-{3[4-Hydroxy-2-(6'-methylsulfinyl-3'-pyridylamino)-5-pyrimidinyl]-ureido}-p-hydroxy-benzyl-penicillin sodium This penicillin was prepared analogous to Example 7, starting from 1 gm (0.0024 mol) of amoxicillin trihydrate and the reaction product of 580 mgm (0.00218 mol) of 5-amino-4-hydroxy-2-(6'-methylsulfinyl-3'-pyridylamino)pyrimidine with 10 ml of N,N-diethyl-trimethylsilylamine and 216 mgm of phosgene.

Yield: 0.39 gm of the sodium salt (27%);
IR-Spectrum: 1770, 1650, 1020 cm$^{-1}$;
NMR-Spectrum (DMSO+CD$_3$OD) signals at ppm: 1.5 (d,6H), 2.7 (s,3H), 4.0 (s,1H), 5.4 (m,3H), 6.65 (d,2H), 7.2 (d,2H), 7.7 (d,1H), 8.25 (s,1H), 8.5 (m,1H), 8.9 (s,1H).

EXAMPLE 34

D-α-{3-[4-Hydroxy-2-(6'-methylsulfonyl-3'-pyridylamino)-5-pyrimidinyl]-ureido}-p-hydroxy-benzyl-penicillin sodium This penicillin was prepared analogous to Example 7, starting from 570 mgm (0.00136 mol) of amoxicillin trihydrate and the reaction product of 350 mgm (0.00124 mol) of 5-amino-4-hydroxy-2-(6'-methyl-sulfonyl-3'-pyridylamino)pyrimidine with 5 ml of N,N-diethyltrimethylsilylamine and 123 mgm of phosgene.

Yield: 300 mgm of the sodium salt (35%);
IR-Spectrum: 1765, 1660, 1380, 1155 cm$^{-1}$;
NMR-Spectrum (CD$_3$OD) signals at ppm: 1.5 (d,6H), 3.1 (s,3H), 4.0 (s,1H), 5.4 (m,3H), 6.65 (d,2H), 7.2 (d,2H), 7.9 (d,1H), 8.3 (s,1H), 8.6 (d,1H), 8.9 (s,1H).

EXAMPLE 35

D-α-{3-[2-(5'-Aminocarbonyl-2'-thienylamino)-4-hydroxy-5-pyrimidinyl]-ureido}-p-hydroxy-benzyl-penicillin sodium Preparation analogous to Example 7, starting from 840 mgm of amoxicillin trihydrate (0.001 mol) and the reaction product of 250 mgm of the pyrimidine of Example 1(ao) (0.001 mol) with N,N-diethyl-trimethylsilylamine.

Yield: 340 mgm of the sodium salt (51%);
NMR-Spectrum (DMSO+CD$_3$OD) signals at ppm: 1.55 (d,6H), 4.0 (s,1H), 5.45 (m,3H), 6.6 (d,1H), 6.75 (d,2H), 7.25 (d,2H), 7.45 (d,1H), 8.35 (s,1H).
IR-Spectrum 1765, 1655, 1610, 1140 cm$^{-1}$.

EXAMPLE 36

D-α-{3-[4-Hydroxy-2-(5'-tetrazolylmethylamino)-5-pyrimidinyl]-ureido}-p-hydroxy-benzyl-penicillin sodium Preparation analogous to Example 7 with the pyrimidine of Example I.

Yield: 46%.
IR-Spectrum: 1765, 1650, 1605 cm$^{-1}$;
NMR-Spectrum (DMSO+CD$_3$OD) signals at ppm: 1.55 (d,6H), 4.05 (s,1H), 4.45 (s,2H), 5.40 (q,2H), 5.50 (s,1H), 6.75 (d,2H), 7.25 (d,2H), 8.10 (s,1H).

EXAMPLE 37

D-α-{3-[4-Hydroxy-2-(2',6'-dihydroxy-4'-pyrimidinylamino)-5-pyrimidinyl]-ureido}-p-hydroxy-benzyl-penicillin sodium Synthesis analogous to Example 7 with the pyrimidine of Example I(as) and amoxycillin.

Yield: 54.5%.
IR-Spectrum: 1765, 1660, 1605 cm$^{-1}$;
NMR-Spectrum (DMSO+CD$_3$OD) signals at ppm: 1.55 (d,6H), 4.0 (s,1H), 5.45 (q,2H+s,1H), 6.75 (d,2H), 7.3 (d,2H), 8.35 (s,1H), 8.55 (s,1H).

EXAMPLE 38

D-α-{3-[4-Hydroxy-2-(2',4'-dihydroxy-5'-pyrimidinylamino)-5-pyrimidinyl]-ureido}-p-hydroxy-benzyl-penicillin sodium Synthesis analogous to Example 7 with the pyrimidine of Example I(aq) and amoxycillin.
Yield: 39% of the sodium salt.
IR-Spectrum: 1765, 1655, 1600 cm$^{-1}$;
NMR-Spectrum (DMSO+CD$_3$OD) signals at ppm: 1.55 (d,6H), 4.10 (s,1H), 5.40 (q,2H), 5.50 (s,1H), 6.70 (d,2H), 7.25 (d,2H), 8.35 (s,1H), 8.70 (s,1H).

EXAMPLE 39

D-α-{3-[4-Hydroxy-2-(4',6'-dihydroxy-2'-pyrimidinylamino)-5-pyrimidinyl]-ureido}-p-hydroxy-benzyl-penicillin sodium Synthesis analogous to Example 7, starting from amoxycillin and the aminopyrimidine of Example I(ar).
Yield: 42.5%.
IR-Spectrum: 1765, 1660, 1610 cm$^{-1}$;
NMR-Spectrum (DMSO+CD$_3$OD) signals at ppm: 1.55 (d,6H), 4.05 (s,1H), 5.45 (m,3H), 6.70 (d,2H), 7.25 (d,2H), 8.30 (s,1H), 8.85 (s,1H).

EXAMPLE 40

Pivaloyloxymethyl 6-{D-α-[3-(4-hydroxy-2-(2'-thienylmethylamino)-5-pyrimidinyl)-ureido]-p-hydroxyphenyl-acetamido}-penicillanate 1.28 gm (0.002 mol) of the end product of Example 10 were suspended in 10 ml of acetone. A solution of 340 mgm of pivaloyloxymethyl chloride (0.0022 mol) in 10 ml of acetone and 0.2 ml of a 25% sodium iodide solution in water were added thereto. The mixture was refluxed for 5 hours, cooled and admixed with 15 ml of ice water. After decanting, the precipitated rather greasy product was again admixed with 10 ml of ice water and stritted for 5 minutes. The mixture was then suction-filtered, and the colorless product was dissolved in ethyl acetate, washed with water, with sodium bicarbonate solution and again with water, and subsequently dried in vacuo.
Yield: 950 mgm (66%).
IR-Spectrum: 1770, 1720, 1650 cm$^{-1}$;
NMR-Spectrum (CDCl$_3$+CD$_3$OD) signals at ppm: 1.2 (s,9H), 1.55 (d,6H), 4.2 (s,1H), 4.4 (s,2H), 5.45 (q,2H), 5.5 (s,1H), 5.65 (q,2H), 6.7 (d,2H), 6.85 (m,2H), 7.30 (d,2H), 7.40 (m,1H), 8.1 (s,1H).

The following penicillanates were synthesized analogously:

1-Propionyloxyethyl 6-{D-α-[3-(4-hydroxy-2-(2'-thienylmethylamino)-5-pyrimidinyl)-ureido]-p-hydroxy-phenylacetamido}-penicillanate;

1'-Acetoxyethyl-6-{D-α-[3-(4-hydroxy-2-(2'-thienylmethylamino)-5-pyrimidinyl)-ureido]-p-hydroxy-phenylacetamido}-penicillanate; and Pivaloyloxymethyl 6-{D-α-[3-(4-hydroxy-2-(5'-chloro-2'-thienylmethylamino)-5-pyrimidinyl)-ureido]-p-hydroxyphenylacetamido}-penicillanate.

EXAMPLE 41

Pivaloyloxymethyl 6-{D-α-[3-(4-hydroxy-2-(2'-furylmethylamino)-5-pyrimidinyl)-ureido]-p-hydroxy-phenylacetamido}-penicillanate Synthesis analogous to Example 39, starting from 625 mgm (0.001 mol) of the end product of Example 15 and 170 mgm of pivaloyloxymethyl chloride.
Yield: 420 mgm (69%);
IR-spectrum: 1770, 1715, 1650 cm$^{-1}$;
NMR-Spectrum (CDCl$_3$+CD$_3$OD) signals at ppm: 1.2 (s,9H), 1.55 (d,6H), 4.3 (s,1H), 4.5 (broad s,2H), 5.4 (q,2H+s,1H), 5.65 (q,2H), 6.3 (m,2H), 6.7 (d,2H), 7.2 (d,2H), 7.45 (s,1H), 8.1 (s,1H).

EXAMPLE 42

Pivaloyloxymethyl 6-{D-α-[3-(4-hydroxy-2-(5'-aminosulfonyl-2'-thienyl-methylamino)-5-pyrimidinyl)-ureido]-p-hydroxyphenyl-acetamido}-penicillanate Synthesis analogous to Example 39, starting from the sodium salt of Example 27 and pivaloyloxymethyl chloride.
Yield: 74%;
IR-Spectrum: 1770, 1700, 1660 cm$^{-1}$;
NMR-Spectrum (CDCl$_3$+CD$_3$OD) signals at ppm: 1.2 (s,9H), 1.55 (d,6H), 4.25 (s,1H), 4.6 (s,2H), 5.4 (m,3H), 5.70 (q,2H), 6.7 (d,2H), 6.9 (d,1H), 7.45 (d,1H), 8.05 (s,1H).

EXAMPLE 43

Pivaloyloxymethyl 6-{D-α-[3-(4-hydroxy-2-(3'-pyridylmethylamino)-5-pyrimidinyl)-ureido]-p-hydroxy-phenylacetamido}-penicillanate Preparation analogous to Example 39, starting from the sodium salt of Example 5 and pivaloyloxymethyl chloride.
Yield: 58%;
IR-Spectrum: 1770, 1710, 1650, 1600 cm$^{-1}$;
NMR-Spectrum (CD$_3$OD) signals at ppm: 1.15 (s,9H), 1.60 (d,2H), 4.20 (s,1H), 4.55 (s,2H), 5.45 (m,3H), 5.70 (q,2H), 6.70 (d,2H), 7.20 (m,3H), 7.6 (m,1H), 8.05 (s,1H), 8.35 (m,2H).

III. Preparation of cephalosporins of the formula I or I'

EXAMPLE 44

Sodium 7-{D-α-[3-(4-hydroxy-2-(3'-pyridylamino)-5-pyrimidinyl)-ureido]-p-hydroxyphenyl-acetamido}-3-acetoxymethyl-ceph-3-em-4-carboxylate 1.96 gm (0.005 mol) of the ureidocarboxylic acid of Example II(b) were dissolved, together with 2.1 gm of benzhydrol 7-amino-3-acetoxy-methyl-ceph-3-em-4-carboxylate (0.005 mol), in a mixture of 50 ml of methylene chloride and 10 ml of dimethyl-formamide. 1.15 gm (0.0055 mol) of dicyclohexyl carbodiimide were added to the solution while cooling with ice, and the solution was stirred for 8 hours at 5° C. The urea formed thereby was filtered off, and the filtrate was evaporated to dryness in vacuo. To remove small impurities, the residue was rapidly chromatographed on a silicagel column (eluant: methylene chloride/methanol 12:1). Yield of benzhydryl ester 3.4 gm (82%).

The product thus obtained was dissolved in a little methylene chloride, and the solution was stirred for 45 minutes with 2 ml of anisole and 10 ml of trifluoroacetic acid while cooling with ice. Subsequently, 50 ml of toluene were added twice, each time with evaporation of the mixture to dryness in vacuo. The resulting product was admixed with ether and isolated by suction filtration. By addition of the calculated amount of sodium ethylhexanoate in methanol and by addition of ether, the sodium salt was precipitated, suction-filtered off and dried in vacuo.

Yield of the sodium salt: 2.50 gm (91%).

IR-Spectrum: 1765, 1660, 1615, 1550 cm$^{-1}$;

NMR-Spectrum (DMSO+CD$_3$OD) signals at ppm: 2.1 (s,3H), 3.45 (q,2H), 4.85 (q,2H+d,1H), 5.55 (s,1H), 5.60 (d,1H), 6.75 (d,2H), 7.25 (d,2H), 7.4 (m,1H), 8.3 (m,3H), 8.7 (s,1H).

EXAMPLE 45

Sodium 7-{D-α-[3-(4-hydroxy-2-(3'-pyridylamino)-5-pyrimidinyl)-ureido]-p-hydroxyphenyl-acetamido}-3-[(1-methyl-tetrazol-5-yl)-thiomethyl]-ceph-3-em-4-carboxylate 3.94 gm (0.01 mol) of the ureidocarboxylic acid of Example II(b) were reacted analogous to Example 44 with 4.94 gm (0.01 mol) of benzhydryl 7-amino-3-[(1-methyltetrazol-5-yl)-thio-methyl]-ceph-3-em-4-carboxylate. After splitting of the protective group, 4.85 gm (65%) of the sodium salt were obtained.

IR-Spectrum: 1765, 1660, 1610, 1540 cm$^{-1}$;

NMR-Spectrum (DMSO+CD$_3$OD) signals at ppm: 3.50 (q,2H), 3.90 (s,3H), 4.30 (q,2H, partly masked by solvent), 4.80 (d,1H), 5.50 (s,1H), 5.70 (d,1H), 6.75 (d,2H), 7.35 (d,2H), 7.4 (m,1H), 8.3 (m,3H), 8.75 (s,1H).

EXAMPLE 46

Sodium 7-{D-α-[3-(4-hydroxy-2-(3'-pyridylamino)-5-pyrimidinyl)-ureido]-p-hydroxyphenyl-acetamido}-3-[(2-methyl-thiadiazol-5-yl)-thiomethyl]-ceph-3-em-4-carboxylate Prepared analogous to Example 44, starting from 790 mgm (0.002 mol) of the ureidocarboxylic acid of Example II(b) and 1.02 gm (0.002 mol) of benzhydryl 7-amino-3-[(2-methyl-thiadiazol-5-yl)-thiomethyl]-ceph-3-em-4-carboxylate. After splitting of the protective group, 540 mgm (39%) of the sodium salt were obtained.

IR-Spectrum: 1760, 1655, 1615, 1540 cm$^{-1}$;

NMR-Spectrum (DMSO+CD$_3$OD) signals at ppm: 2.7 (s,3H), 3.50 (q,2H), 4.45 (q,2H), 4.90 (d,1H), 5.50 (s,1H), 5.65 (d,1H), 6.75 (d,2H), 7.3 (d,2H), 7.4 (m,1H), 8.3 (m,3H), 8.75 (s,1H).

EXAMPLE 47

Sodium 7-{D,L-α-[3-(4-hydroxy-2-(3'-pyridylamino)-5-pyrimidinyl)-ureido]-2-thienylacetamido}-3-[(1-methyl-tetrazol-5-yl)-thiomethyl]-ceph-3-em-4-carboxylate This cephalosporin was prepared, starting from 1.11 gm (0.0029 mol) of the ureidocarboxylic acid of Example II(d) and 1.5 gm (0.003 mol) of the benzhydryl ester used in Example 45, and performing the reaction analogous to Example 44. After splitting of the protective group, 920 mgm (48%) of the sodium salt were obtained.

IR-Spectrum: 1760, 1660, 1610, 1540 cm$^{-1}$;

NMR-Spectrum (DMSO+CD$_3$OD) signals at ppm: 3.55 (q,2H), 3.90 (s,3H), 4.35 (q,2H), 4.90 (dd,1H), 5.5 (dd,1H), 5.75 (broad s,1H), 6.9 (m,2H), 7.35 (d,2H), 8.25 (m,3H), 8.75 (s,1H).

The following cephalosporin was synthesized analogously:

Sodium 7-{D-α-[3-(4-hydroxy-2-(6'-methoxy-3'-pyridyl)-5-pyrimidinyl)-ureido-p-hydroxy-phenyl-acetamido}-3-[(1-methyl-tetrazol-5-yl)-thiomethyl]-ceph-3-em-4-carboxylate.

EXAMPLE 48

Sodium 7-{D-α-[3-(4-hydroxy-2-(2'-thienylmethyl)-5-pyrimidinyl)-ureidol]-p-hydroxy-phenyl-acetamido}-3-[(1,2,4-thiadiazol-5-yl)-thiomethyl]-ceph-3-em-4-carboxylate This cephalosporin was prepared, starting from 415 mgm (0.001 mol) of the ureidocarboxylic acid of Example II(g) and 500 mgm (0.001 mol) of benzhydryl 7-amino-3-[(1,2,4-thiadiazol-5-yl)-thiomethyl]-ceph-3-em-4-carboxylate analogous to Example 44. After splitting of the protective group, 410 mgm (35%) of the sodium salt were obtained.

IR-spectrum: 1760, 1660, 1615, 1540 cm$^{-1}$;

NMR-Spectrum (DMSO+CD$_3$OD) signals at ppm: 3.50 (q,2H), 4.50 (m,4H), 4.95 (d,1H), 5.50 (s,1H), 5.60 (d,1H), 6.75 (d,2H), 6.85 (m,2H), 7.25 (d,2H), 7.4 (m,1H), 8.1 (s,1H).

EXAMPLE 49

Sodium 7-{D-α-[3-(4-hydroxy-2-(5'-ethoxycarbonyl-2-thienylamino)-5-pyrimidinyl)-ureido]-p-hydroxy-phenyl-acetamido}-3-acetoxymethyl]-ceph-3-em-4-carboxylate This cephalosporin was prepared analogous to Example 44, starting from 4.70 gm (0.01 mol) of the ureidocarboxylic acid of Example II(f) and 4.20 gm (0.01 mol) of the cephalosporin derivative used in Example 44.

Yield after separation of the protective group: 3.95 gm (51%) of the sodium salt.

IR-Spectrum: 1760, 1655, 1610, 1545 cm$^{-1}$;

NMR-Spectrum (DMSO+CD$_3$OD) signals at ppm: 1.3 (t,3H), 2.05 (s,2H), 3.55 (q,2H), 4.30 (q,2H), 4.85 (m,2+1H), 5.4 (s,1H), 5.6 (d,1H), 6.8 (d,2H), 7.35 (d,2H), 7.9 (m,2H), 8.05 (s,1H).

EXAMPLE 50

Sodium 7-{D-α-[3-(4-hydroxy-2-(2'-thienylmethylamino)-5-pyrimidinyl)-ureido]-p-hydroxy-phenyl-acetamido}-3-[(2-methyl-1,3,4-thiadiazol-5-yl)-thiomethyl]-ceph-3-em-4-carboxylate Prepared analogous to Example 44, starting from 580 mgm (0.0014 mol) of the ureidocarboxylic acid of Example II(g) and 720 mgm (0.0014 mol of the cephalosporin used in Example 46.

Yield after separation of the benzhydryl group: 500 mgm (46%) of the sodium salt.

IR-Spectrum: 1760, 1660, 1610, 1550 cm$^{-1}$;

NMR-Spectrum (DMSO+CD$_3$OD) signals at ppm: 2.75 (s,3H), 3.55 (q,2H), 4.25 (q,2H, partly masked by solvent), 4.5 (broad s,2H), 5.0 (d,1H), 5.45 (s,1H), 5.65 (d,1H), 6.6–7.4 (m,7H), 8.1 (s,1H).

EXAMPLE 51

Sodium 7-{D-α-[3-(4-hydroxy-2-(3'-pyridylamino)-5-pyrimidinyl)-ureido]-2-furyl-acetamido}-3-[(1-methyl-tetrazol-5-yl)-thiomethyl]-ceph-3-em-4-carboxylate Analogous to Example 44, 775 mgm of the ureidocarboxylic acid of Example II(c) (0.002 mol) were reacted with 1.0 gm (0.0021 mol) of the cephalosporin benzhydryl ester used in Example 45. After separation of the benzhydryl protective group, 730 mgm (50%) of the sodium salt were obtained.

IR-Spectrum: 1770, 1655, 1615, 1545 cm$^{-1}$;
NMR-Spectrum (DMSO+CD$_3$OD) signals at ppm: 3.55 (q,2H), 3.90 (s,3H), 4.35 (q,2H), 4.95 (d,1H), 5.45 (d,1H), 5.75 (s,1H), 6.4 (m,2H), 7.4 (m,1H), 7.6 (broad s,1H), 8.25 (m,3H), 8.8 (broad s,1H).

EXAMPLE 52

Sodium 7-{D-α-[3-(4-hydroxy-2-(5'-ethoxycarbonyl-2'-thienyl)-5-pyrimidinyl)-ureido]-p-hydroxy-phenyl-acetamido}-3-[(1-methyl-tetrazol-5-yl)-thiomethyl]-ceph-3-em-4-carboxylate Analogous to Example 44, 470 mgm (0.001 mol) of the ureidocarboxylic acid of Example II(f) were reacted with 500 mgm (0.001 mol) of the benzhydryl ester used in Example 45. After separation of the benzhydryl protective group, 440 mgm (53.5%) of the sodium salt were obtained.

IR-Spectrum: 1760, 1655, 1615, 1540 cm$^{-1}$;
NMR-Spectrum (DMSO+CD$_3$OD) signals at ppm: 1.3 (t,3H), 3.4 (q,2H), 3.9 (s,3H), 4.35 (m,4H), 4.85 (d,1H), 5.40 (s,1H), 5.55 (d,1H), 6.7 (d,2H), 7.35 (d,2H), 7.85 (m,2H), 8.25 (s,1H).

EXAMPLE 53

Sodium 7-{D-α-[3-(4-hydroxy-2-(2'-furylmethylamino)-5-pyrimidinyl)-ureido]-p-hydroxy-phenyl-acetamido}-3-[(2-methyl-thiadiazol-5-yl)-thiomethyl]-ceph-3-em-4-carboxylate Synthesized analogous to Example 44, starting from 1.12 gm of the ureidocarboxylic acid of Example II(j) (0.0028 mol) and 1.53 gm (0.003 mol) of benzhydryl 7-amino-3-[(2-methyl-thiadiazol-5-yl)-thiomethyl]-ceph-3-em-4-carboxylate.

Yield of sodium salt: 760 mgm (36);
IR-Spectrum: 1770, 1660, 1610, 1545 cm$^{-1}$;
NMR-Spectrum (DMSO+CD$_3$OD) signals at ppm: 2.75 (s,3H), 3.45 (q,2H), 4.45 (m,4H), 4.95 (d,1H), 5.40 (s,1H), 5.60 (d,1H), 6.3 (m,2H), 6.85 (d,2H), 7.35 (d,2H), 7.5 (s,1H), 8.05 (s,1H).

The following cephalosporins were prepared analogously:
Sodium 7-{D-α-[3-(4-hydroxy-2-(2'-pyridylmethylamino)-5-pyrimidinyl)-uredio]-p-hydroxy-phenyl-acetamido}-3-[(1-methyl-tetrazol-5-yl)-thiomethyl]-ceph-3-em-4-carboxylate,
Sodium 7-{D-α-[3-(4-hydroxy-2-(4'-pyridylmethylamino)-5-pyrimidinyl)-ureido]-p-hydroxy-phenyl-acetamido}-3-[(1-methyl-tetrazol-5-yl)-thiomethyl]-ceph-3-em-4-carboxylate.

EXAMPLE 54

Sodium 7{D-α-[(4-hydroxy-2-(2'-furylmethylamino)-5-pyrimidinyl)-ureido]-p-hydroxy-phenyl-acetamido}-3-acetoxymethyl-ceph-3-em-4-carboxylate 1.21 gm (0.01 mol) of N,N-dimethyl-aniline were added to a solution of 3.99 gm of the ureidocarboxylic acid of Example II(j) (0.01 mol) in 30 ml of anhydrous methylene chloride and 30 ml of dimethylformamide. The solution was cooled to −15° C., and at this temperature a solution of 1.1 gm (0.01 mol) of ethyl chloroformate in 5 ml of methylene chloride was added. The resulting mixture was kept at this temperature for 45 minutes. 3 gm of N,O-bis-trimethylsilyl-acetamide were added to a suspension of 2.72 gm (0.01 mol) of 7-aminocephalosporanic acid in 80 ml of anhydrous acetonitrile, whereby a solution was obtained. The solution was cooled to −20° C. and added to the above solution. Thereafter, the mixture was reacted at −10° C. for 60 minutes and then at +10° C. for 60 minutes. After this time 5 ml of methanol were added, and insoluble material was filtered off. The solvent was then removed in vacuo. The residue was taken up in 100 ml of water, and the solution was adjusted to pH 7.5. At this pH value it was extracted twice with ethyl acetate, and the organic phase was discarded. The aqueous phase was adjusted to pH 2.9 with dilute hydrochloric acid while cooling with ice, and the precipitated product was suction-filtered off, washed with a little water and dried in vacuo. The aqueous solution was extracted twice with ethyl acetate, the ethyl acetate phase was dried, and the solvent was distilled off in vacuo. A second batch was obtained which was identical to the product first obtained.

Both solid products were combined and dissolved in 80 ml of dry methanol with the calculated amount of sodium ethyl-hexanoate. Insoluble matter was filtered off, and ether was added to the filtrate until complete precipitation. The precipitated solid product was suction-filtered off and dried.

Yield: 3.60 gm of the sodium salt (53%);
IR-Spectrum: 1765, 1655, 1615, 1645 cm$^{-1}$;
NMR-Spectrum (DMSO+CD$_3$OD) signals at ppm: 2.05 (s,3H), 3.45 (q,2H), 4.5 (s,2H), 4.80 (q,2H+d,1H), 5.50 (s,1H), 5.65 (d,1H), 6.35 (m,2H), 6.75 (d,2H), 7.30 (d,2H), 7.45 (s,1H), 8.05 (s,1H).

EXAMPLE 55

Sodium 7-{D-α-[3-(4-hydroxy-2-(2'-furylmethylamino)-5-pyrimidinyl)-ureido]-p-hydroxy-phenyl-acetamido}-3-carbamoyloxymethyl-ceph-3-em-4-carboxylate Preparation analogous to Example 54, starting from 1.32 gm (0.005 mol) of 7-amino-3-carbamoyloxymethyl-ceph-3-em-4-carboxylic acid and 2.00 gm of the ureidocarboxylic acid of Example II(j) (0.005 mol).

Yield of the sodium salt: 1.47 gm (41%);
IR-Spectrum: 1765, 1660, 1610, 1540 cm$^{-1}$;
NMR-Spectrum (DMSO+CD$_3$OD) signals at ppm: 3.55 (q,2H), 4.45 (broad s,2H), 4.8 (broad, 2H+1H), 5.45 (s,1H), 5.65 (d,1H), 6.25 (m,2H), 6.85 (d,2H), 7.35 (d,2H), 7.45 (s,1H), 8.0 (s,1H).

EXAMPLE 56

Sodium
7-{D-α-[(4-hydroxy-2-(2'-furylmethylamino)-5-pyrimidinyl)-ureido]-p-hydroxy-phenyl-acetamido}-3-[(1-methyl-tetrazol-5-yl)-thiomethyl]-ceph-3-em-4-carboxylate Preparation analogous to Example 54, starting from 400 mgm (0.001 mol) of the ureidocarboxylic acid of Example II(j) and 334 mgm (0.001 mol) of 7-amino-[(1-methyl-tetrazol-5-yl)-thiomethyl]-ceph-3-em-4-carboxylic acid.

Yield of the sodium salt: 430 mgm (58%);
IR-Spectrum: 1765, 1655, 1610, 1540 cm$^{-1}$;
NMR-Spectrum (DMSO+CD$_3$OD) signals at ppm: 3.50 (q,2H), 3.95 (s,3H), 4.35 (q,2H), 4.50 (s,2H); 4.95 (d,1H), 5.45 (s,1H), 5.60 (d,1H), 6.35 (m,2H), 6.7 (d,2H), 7.2 (d,2H), 7.5 (s,1H), 8.05 (s,1H).

EXAMPLE 57

Sodium
7-{D-α-[3-(4-hydroxy-2-(2'-furylmethylamino)-5-pyrimidinyl)-uredio]-p-hydroxy-phenyl-acetamido}-3-[(2-methylaminothiadiazol-5-yl)-thiomethyl]-ceph-3-em-4-carboxylate Preparation analogous to Example 54, starting from 800 mgm (0.002 mol) of the ureidocarboxylic acid of Exmple II(j) and 720 mgm (0.002 mol) of 7-amino-3-[(2-methyl-amino-thiadiazol-5-yl)thiomethyl]-ceph-3-em-4-carboxylic acid.

Yield of the sodium salt: 960 mgm (62%);
IR-Spectrum: 1770, 1650, 1615, 1545 cm$^{-1}$;
NMR-Spectrum (DMSO+CD$_3$OD) signals at ppm: 3.0 (s,3H), 3.65 (q,2H), 4.15 (m, partly masked by solvent=2H), 4.4 (s,2H), 5.0 (d,1H), 5.5 (s,1H), 5.70 (d,1H), 6.3 (m,2H), 6.85 (d,2H), 7.35 (d,2H), 7.5 (s,1H), 8.05 (s,1H).

EXAMPLE 58

Sodium
7-{D-α-[3-(4-hydroxy-2-(3'-pyridylmethylamino)-5-pyrimidinyl)-uredio]-p-hydroxy-phenyl-acetamido}-3-carbamoyloxymethyl-ceph-3-em-4-carboxylate Preparation anlogous to Example 54, starting from 2.64 gm (0.01 mol) of 7-amino-3-carbamoyloxymethyl-ceph-3-em-4-carboxylic acid and 4.10 gm (0.01 mol) of the ureidocarboxylic acid of Example II(e).

Yield of the sodium salt: 60%;
IR-Spectrum: 1765, 1660, 1610, 1540 cm$^{-1}$;
NMR-Spectrum (DMSO+CD$_3$OD) signals at ppm: 3.55 (q,2H), 4.5 (s,2H), 4.8 (broad, 2H+1H), 5.45 (s,1H), 5.65 (d,1H), 6.85 (d,2H), 7.35 (m,3H), 7.7 (m,1H), 8.1 (s,1H), 8.5 (m,2H).

EXAMPLE 59

Sodium
7-{D-α-[3-(4-hydroxy-2-(3'-pyridylmethylamino)-5-pyrimidinyl)-ureido]-p-hydroxy-phenyl-acetamido}-3-[(1-methyl-tetrazol-5-yl)-thiomethyl]-ceph-3-em-4-carboxylate Preparation analogous to Example 54, starting from 985 mgm (0.003 mol) of 7-amino-3-[(1-methyl-tetrazol-5-yl)-thiomethyl]-ceph-3-em-4-carboxylic acid and 1.23 gm (0.003 mol) of the ureidocarboxylic acid of Example II(e).

Yield of the sodium salt: 1.58 gm (71%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (q,2H), 4.50 (s,2H), 4.85 (d,1H), 5.45 (s,1H), 5.65 (d,1H), 6.85 (d,2H), 7.35 (m,3H), 7.75 (m,1H), 8.1 (s,1H), 8.5 (m,2H).

EXAMPLE 60

Sodium
7-{D-α-[3-(4-hydroxy-2-(2'-thienylmethylamino)-5-pyrimidinyl)-ureido]-p-hydroxy-phenyl-acetamido}-3-carbamoyloxymethyl-ceph-3-em-4-carboxylate Preparation analogous to Example 54, starting from 1.0 gm (0.0038 mol) of the cephalosporin derivative of Example 58 and 1.6 gm (0.00385 mol) of the ureidocarboxylic acid of Example II(g).

Yield of the sodium salt: 1.33 gm (50.5%);
IR-Spectrum: 1765, 1655, 1605, 1545 cm$^{-1}$;
NMR-Spectrum (DMSO+CD$_3$OD) signals at ppm: 3.55 (q,2H), 4.55 (broad s,2H), 4.85 (m,2+1H), 5.45 (s,1H), 5.65 (d,1H), 6.65 (d,2H), 6.80 (m,2H), 7.30 (d,2H), 7.45 (m,1H), 8.05 (s,1H).

EXAMPLE 61

Sodium
7-{D-α-[3-(4-hydroxy-2-(2'-thienylmethylamino)-5-pyrimidinyl)-ureido]-p-hydroxy-phenyl-acetamido}-3-[(tetrazol-5-yl)-thiomethyl]-ceph-3-em-4-carboxylate Prepared analogously to Example 54, starting from 415 mgm (0.001 mol) of the ureidocarboxylic acid of Example II(g), and 315 mgm (0.001 mol) of 7-amino-3-(tetrazol-5-yl)-thiomethyl-ceph-3-em-4-carboxylate. 385 mgm (52%) of the sodium salt were obtained;

IR-Spectrum: 1765, 1655, 1615, 1540 cm$^{-1}$;
NMR-Spectrum (DMSO+CD$_3$OD) signals at ppm: 3.4 (q,2H), 4.35 (q,2H), 4.5 (s,2H), 4.85 (d,1H), 5.40 (s,1H), 5.55 (d,1H), 6.75 (d,2H), 6.85 (m,2H), 7.30 (d,2H), 7.45 (m,1H), 8.05 (s,1H).

EXAMPLE 62

Sodium
7-{D-α-[3-(4-hydroxy-2-(2'-thienylmethylamino)-5-pyrimidinyl)-ureido]-p-hydroxy-phenyl-acetamido}-3-[(1-methyl-tetrazol-5-yl)-thiomethyl]-ceph-3-em-4-carboxylate Preparation analogous to Example 54, starting from 830 mgm (0.002 mol) of the ureidocarboxylic acid of Example II(g) and 656 mgm (0.002 mol) of 7-amino-3-[(1-methyltetrazol-5-yl)-thiomethyl]-ceph-3-em-4-carboxylic acid.

Yield of the sodium salt: 940 mgm (63%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (q,2H), 4.50 (s, 2H), 4.85 (d,1H), 5.45 (s,1H), 5.65 (d,1H), 6.85 (d,2H), 6.95–7.4 (m,5H), 8.05 (s,1H).

EXAMPLE 63

Sodium
7-{D-α-[3-(4-hydroxy-2-(2'-thienylmethylamino)-5-pyrimidinyl)-uredio]-p-hydroxy-phenyl-acetamido}-3-[(2-methyl-oxadiazol-5-yl)-thiomethyl]-ceph-3-em-4-carboxylate This cephalosporin was prepared analogous to Example 54, starting from 2.08 gm (0.005 mol) of the ureidocarboxylic acid of Example II(g), and 1.65 gm (0.005 mol) of 7-amino-3-[(2-methyl-1,3,4-oxadiazol)-5-yl-thiomethyl]-ceph-3-em-4-carboxylate.

Yield of the sodium salt: 2.22 gm (59%);
IR-Spectrum: 1765, 1650, 1610, 1540 cm$^{-1}$;
NMR-Spectrum (DMSO+CD$_3$OD) signals at ppm: 2.45 (s,3H), 3.6 (q,2H), 4.2 (q,2H), 4.45 (s,2H), 4.95 (d,1H), 5.45 (s,1H), 5.60 (d,1H), 6.75 (d,2H), 6.85–7.4 (m,5H), 8.05 (s,1H).

EXAMPLE 64

Sodium 7-{D-α-[3-(4-hydroxy-2-(2'-thienylmethylamino)-5-pyrimidinyl)-uredio]-m,p-dihydroxy-phenyl-acetamido}-3-[(1-methyl-tetrazol-5-yl)-thiomethyl]-ceph-3-em-4-carboxylate Preparation analogous to Example 54, starting from 2.15 gm (0.005 mol) of the ureidocarboxylic acid of Example II(k) and 1.64 gm (0.005 mol) of the cephalosporin derivative used in Example 62.

Yield of the sodium salt: 2.49 gm (65%);
IR-Spectrum: 1765, 1660, 1605, 1545 cm$^{-1}$;
NMR-Spectrum (DMSO+CD$_3$OD) signals at ppm: 3.50 (q,2H), 3.90 (s,3H), 4.30 (q,2H partly masked by solvent), 4.50 (s,2H), 4.80 (d,1H), 5.50 (s,1H), 5.70 (d,1H), 6.7 (d,1H), 7.0 (m,4H), 7.35 (m,1H), 8.1 (s,1H).

EXAMPLE 65

Sodium 7-{D-α-[3-(4-hydroxy-2-(2'-thienylmethylamino)-5-pyrimidinyl)-uredio]-2-furyl-acetamido}-3-acetoxymethylceph-3-em-4-carboxylate Preparation analogous to Example 54, starting from 390 mgm (0.001 mol) of the ureidocarboxylic acid of Example II(l) and 272 mgm (0.001 mol) of 7-aminocephalosporanic acid.

Yield of the sodium salt: 390 mgm (54%);
IR-Spectrum: 1765, 1660, 1610, 1540 cm$^{-1}$;
NMR-Spectrum (DMSO+CD$_3$OD) signals at ppm: 2.1 (s,3H), 3.45 (q,2H), 4.5 (s,2H), 4.85 (d,1H+q,2H), 5.5 (d,1H), 5.85 (s,1H), 6.3 (m,2H), 7.0 (m,2H), 7.3 (m,1H), 7.5 (s,1H), 8.1 (s,1H).

EXAMPLE 66

Sodium 7-{D-α-[3-(4-hydroxy-2-(2'-thienylmethylamino)-5-pyrimidinyl)-uredio]-2-furyl-acetamido}-3-[(1-methyl-tetrazol-5-yl)-thiomethyl]-ceph-3-em-4-carboxylate Preparation analogous to Example 54, starting from 780 mgm (0.002 mol) of the ureidocarboxylic acid of Example II(l) and 655 mgm (0.002 mol) of the cephalosporin derivative used in Example 62.

Yield of the sodium salt: 650 mgm (46%);
IR-Spectrum: 1770, 1665, 1620, 1550 cm$^{-1}$;
NMR-Spectrum (DMSO+CD$_3$OD) signals at ppm: 3.45 (q,2H), 3.90 (s,3H), 4.35 (q,2H), 4.50 (s,2H), 4.9 (d,1H), 5.5 (d,1H), 5.75 (s,1H), 6.3 (m,2H), 7.0 (m,2H), 7.3 (m,1H), 7.5 (s,1H), 8.1 (s,1H).

The following cephalosporin was synthesized analogously:

Sodium 7-{D,L-α-[3-(4-hydroxy-2-(2'-thienylmethylamino)-5-pyrimidinyl)-uredio]-3-furyl-acetamido}-3-[(1-methyl-tetrazol-5-yl)-thiomethyl]-ceph-3-em-4-carboxylate.

EXAMPLE 67

Sodium 7-{D-α-[(4-hydroxy-2-(2'-thienylmethylamino)-5-pyrimidinyl)-ureido]-2-thienyl-acetamido}-3-[acetoxymethyl]-ceph-3-em-4-carboxylate Preparation analogous to Example 54, starting from the reaction product of 1.21 gm (0.003 mol) of the ureidocarboxylic acid of Example II(m) and 815 mgm (0.003 mol) of 7-amino-cephalosporanic acid.

Yield of the sodium salt: 1.44 gm (61%);
IR-Spectrum: 1765, 1660, 1615, 1535 cm$^{-1}$;
NMR-Spectrum (DMSO+CD$_3$OD) signals at ppm: 2.05 (s,3H), 3.55 (q,2H), 4.50 (s,2H), 4.80 (m,2+1H), 5.45 (d,1H), 5.75 (s,1H), 7.0 (m,4H), 7.25 (m,2H), 8.1 (s,1H).

EXAMPLE 68

Sodium 7-{D-α-[3-(4-hydroxy-2-(2'-thienylmethylamino)-5-pyrimidinyl)-ureido]-2-thienyl-acetamido}-3-[(1-methyltetrazol-5-yl)-thiomethyl]-ceph-3-em-4-carboxylate This cephalosporin was prepared analogous to Example 54, starting from 1.20 gm (0.0029 mol) of the ureidocarboxylic acid of Example II(m) and 980 mgm (0.003 mol) of the cephalosporin derivative used in Example 62. 1.28 gm (57.5%) of the sodium salt were obtained.

IR-Spectrum: 1770, 1660, 1610, 1540 cm$^{-1}$;
NMR-Spectrum (DMSO+CD$_3$OD) signals at ppm: 3.55 (q,2H), 3.90 (s,3H), 4.35 (q,2H), 4.50 (s,2H), 4.90 (d,1H), 5.5 (d,1H), 5.75 (s,1H), 7.0 (m,4H), 7.25 (m,2H), 8.10 (s,1H).

The following cephalosporin was prepared analogously:

Sodium-7-{D-α-[3-(4-hydroxy-2-(3'-thienylmethylamino)-5-pyrimidinyl)-ureido]-p-hydroxy-phenylacetamido}-3-[(1-methyl-tetrazol-5-yl)-thiomethyl]-ceph-3-em-4-carboxylate.

EXAMPLE 69

Sodium 7-{D-α-[3-(4-hydroxy-2-(5'-methyl-2'-thienylmethylamino)-5-pyrimidinyl)-ureido]-p-hydroxy-phenyl-acetamido}-3-acetoxymethyl-ceph-3-em-4-carboxylate Preparation analogous to Example 54, starting from 1.72 gm (0.004 mol) of the ureidocarboxylic acid of Example II(h) and 1.09 gm (0.004 mol) of 7-amino-cephalosporanic acid.

Yield of the sodium salt: 1.55 gm (46%);
IR-Spectrum: 1765, 1655, 1605, 1545 cm$^{-1}$;
NMR-Spectrum (DMSO+CD$_3$OD) signals at ppm: 2.1 (s,3H), 2.4 (s,3H), 3.55 (q,2H), 4.50 (s,2H), 4.80 (m,2+1H), 5.45 (s,1H), 5.65 (d,1H), 6.7 (d,2H), 6.8 (broad s, 2H), 7.20 (d,2H), 8.1 (s,1H).

The following cephalosporin was prepared analogously:

Sodium-7-{D-α-[3-(4-hydroxy-2-(5'-chloro-2'-thienylmethylamino)-5-pyrimidinyl-3-yl)-ureido]-p-hydroxy-phenylacetamido}-3-acetoxymethyl-ceph-3-em-4-carboxylate.

EXAMPLE 70

Sodium 7-{D-α-[3-(4-hydroxy-2-(5'-methyl-2'-thienylmethylamino-5-pyrimidinyl)-ureido]-p-hydroxyphenylacetamido}-3-[(1-methyl-tetrazol-5-yl)-thiomethyl]-ceph-3-em-4-carboxylate Preparation analogous to Example 54, starting from 430 mgm (0.001 mol) of the ureidocarboxylic acid of Example II(h) and 328 mgm (0.001 mol) of 7-amino-[(1-methyltetrazol-5-yl)-thiomethyl]-ceph-3-em-4-carboxylic acid.

Yield of the sodium salt: 410 mgm (53.5%);
IR-Spectrum (DMSO+CD$_3$OD) signals at ppm: 2.4 (s,3H), 3.5 (q,2H), 3.9 (s,3H), 4.40 (q,2H), 4.50 (s,2H), 4.85 (d,1H), 5.45 (s,1H), 5.65 (d,1H), 6.7 (d,2H), 6.8 (broad s,2H), 7.25 (d,2H), 8.1 (s,1H).

EXAMPLE 71

Sodium 7-{D-α-[3-(4-hydroxy-2-(5'-chloro-2'-thienylmethylamino-5-pyrimidinyl)-ureido]-p-hydroxy-phenyl-acetamido}-3-[(1-methyl-tetrazol-5-yl)-thiomethyl]-ceph-3-em-4-carboxylate Preparation analogous to Example 54, starting from 450 mgm (0.001 mol) of the ureidocarboxylic acid of Example II(i) and 328 mgm (0.001 mol) of 7-amino-[(1-methyl-tetrazol-5-yl)-thiomethyl]-ceph-3-em-4-carboxylic acid.

Yield of the sodium salt: 540 mgm (61.5%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (q,2H), 4.50 (s,2H), 4.85 (d,1H), 5.45 (s,1H), 5.65 (d,1H), 6.7–7.0 (m,4H), 7.25 (d,2H), 8.15 (s,1H).

EXAMPLE 72

Sodium 7-{D-α-[3-(4-hydroxy-2-(2'-furylmethylamino-5-pyrimidinyl)-ureido]-p-hydroxy-phenyl-acetamido}-3-[(1,2,3,-triazol-4-yl)-thiomethyl]-ceph-3-em-4-carboxylate 3.99 gm (0.01 mol) of the ureidocarboxylic acid of Example II(j) were reacted analogous to Example 54 with 3.12 gm (0.01 mol) of 7-amino-3-[(1,2,3-triazol-4-yl)-thiomethyl]-ceph-3-em-4-carboxylic acid. 4.05 gm (57%) of the sodium salt were obtained.

IR-Spectrum: 1770, 1660, 1610, 1540 cm$^{-1}$;
NMR-Spectrum (DMSO+CD$_3$OD) signals at ppm: 3.55 (q,2H), 4.30 (q,2H), 4.4 (s,2H, partly masked by solvent), 4.85 (d,1H), 5.50 (s,1H), 5.70 (d,1H), 6.3 (m,2H), 6.75 (d,2H), 7.25 (d,2H), 7.5 (s,1H), 7.75 (s,1H), 8.05 (s,1H).

EXAMPLE 73

Sodium 7-{D-α-[3-(4-hydroxy-2-(2'-furylmethylamino-5-pyrimidinyl)-ureido]-p-hydroxy-phenyl-acetamido}-3-[(1,3,4-thiadiazol-2-yl)-thiomethyl]-ceph-3-em-4-carboxylate Prepared analogous to Example 54, starting from 800 mgm (0.002 mole) of the ureidocarboxylic acid of Example II(j) and 660 mgm (0.002 mol) of 7-amino-3-[(1,3,4-thiadiazol-2-yl)-thiomethyl]-ceph-3-em-4-carboxylic acid. 810 mgm (55%) of the sodium salt were obtained.

IR-Spectrum: 1770, 1655, 1615, 1540 cm$^{-1}$;
NMR-Spectrum (DMSO+CD$_3$OD) signals at ppm: 3.50 (q,2H), 4.45 (m,4H), 4.90 (d,1H), 5.50 (s,1H), 5.65 (d,1H), 6.35 (m,2H), 6.70 (d,2H), 7.2 (d,2H), 7.5 (s,1H), 8.05 (s,1H), 8.55 (s,1H).

EXAMPLE 74

Sodium 7-{D-α-[3-(4-hydroxy-2-(2'-furylmethylamino)-5-pyrimidinyl)-ureido]-2-furyl-acetamido}-3-acetoxymethylceph-3-em-4-carboxylate 1.86 gm (0.005 mol) of the ureidocarboxylic acid of Example II(n) were reacted analogous to Example 54 with 1.36 gm of 7-amino-cephalosporanic acid. 1.76 gm (54.5%) of the sodium salt were obtained.

IR-Spectrum: 1765, 1660, 1605, 1545 cm$^{-1}$;
NMR-Spectrum (DMSO+CD$_3$OD) signals at ppm: 2.05 (s,3H), 3.55 (q,2H), 4.4 (s,2H), 4.85 (m, 2+1H), 5.45 (d,1H), 5.75 (s,1H), 6.3 (m,4H), 7.5 (m,2H), 8.1 (s,1H).

EXAMPLE 75

Sodium 7-{D-α-[3-(4-hydroxy-2-(2'-furylmethylamino)-5-pyrimidinyl)-ureido]-2-furyl-acetamido}-3-[(1-methyl-tetrazol-5-yl)-thiomethyl]-ceph-3-em-4-carboxylate Preparation analogous to Example 54, starting from 373 mgm (0.001 mol) of the ureidocarboxylic acid of Example II(n) and 328 mgm (0.001 mol) of 7-amino-[(1-methyltetrazol-5-yl)-thiomethyl]-ceph-3-em-4-carboxylic acid.

Yield of the sodium salt: 420 mgm (60%);
NMR-Spectrum (DMSO+CD$_3$OD) signals at ppm: 3.5 (q,2H), 3.9 (s,3H), 4.40 (m,4H), 4.95 (d,1H), 5.45 (d,1H), 5.70 (s,1H), 6.35 (m,4H), 7.45 (m,2H), 8.1 (s,1H).
IR-Spectrum: 1765, 1655, 1610, 1550 cm$^{-1}$.

EXAMPLE 76

Sodium 7-{D-α-[3-(4-hydroxy-2-(2'-furylmethylamino)-5-pyrimidinyl)-ureido]-2-thienyl-acetamido}-3-acetoxymethyl-ceph-3-em-4-carboxylate 1.15 gm (0.003 mol) of the ureidocarboxylic acid of Example II(o) were reacted analogous to Example 54 with 815 mgm of 7-amino-cephalosporanic acid. 890 mgm (45%) of the sodium walt were obtained.

IR-Spectrum: 1765, 1655, 1610, 1550 cm$^{-1}$;
NMR-Spectrum (DMSO+CD$_3$OD) signals at ppm: 2.05 (s,3H), 3.50 (g,2H), 4.50 (s,2H), 4.85 (m,3H), 5.5 (d,1H), 5.7 (s,1H), 6.3 (m,2H), 7.0 (m,2H), 7.35 (m,1H), 7.5 (m,1H), 8.1 (s,1H).

EXAMPLE 77

Sodium 7-{D-α-[3-(4-hydroxy-2-(2'-furylmethylamino)-5-pyrimidinyl)-ureido]-2-thienyl-acetamido}-3-[(1-methyltetrazol-5-yl)-thiomethyl]-ceph-3-em-4-carboxylate Preparation analogous to Example 54, starting from 385 mgm (0.001 mol) of the ureidocarboxylic acid of Example II(c) and 328 mgm (0.001 mol) of 7-amino-[(1-methyltetrazol-5-yl)-thiomethyl]-ceph-3-em-4-carboxylic acid.

Yield of the sodium salt: 405 mgm (57%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (m,4H), 4.95 (d,1H), 5.45

(d,1H), 5.70 (s,1H), 6.3 (m,2H), 7.0 (m,2H), 7.4 (m,2H), 8.1 (s,1H).

EXAMPLE 78

Sodium 7-{D-α-[3-(4-hydroxy-2-(5'-methyl-2'-furylmethylamino)-5-pyrimidinyl)-ureido]-p-hydroxy-phenylacetamido}-3-[(1-methyl-tetrazol-5-yl)-thiomethyl]-ceph-3-em-4-carboxylate Preparation analogous to Example 54, starting from 1.65 gm (0.004 mol) of the ureidocarboxylic acid of Example II(p) and 1.32 gm (0.004 mol) of 7-amino-[(1-methyltetrazol-5-yl)-thiomethyl]-ceph-3-em-4-carboxylic acid.

Yield of the sodium salt: 1.82 gm (60.5%);
IR-Spectrum: 1765, 1650, 1610, 1550 cm$^{-1}$;
NMR-Spectrum (DMSO+CD$_3$OD) signals at ppm: 2.5 (s,3H), 3.5 (q,2H), 3.9 (s,3H), 4.40 (m,4H), 4.85 (d,1H), 5.45 (s,1H), 5.65 (d,1H), 6.3 (m,2H), 6.80 (d,2H), 7.30 (d,2H), 8.1 (s,1H).

The following cephalosporins were synthesized analogously:

Sodium 7-{D-α-[3-(4-hydroxy-2-(5'-methyl-2'-furylmethylamino)-5-pyrimidinyl)-ureido]-2-thienylacetamido}-3-[(1-methyl-tetrazol-5-yl)-thiomethyl]-ceph-3-em-4-carboxylate; and Sodium 7-{D-α-[3-(4-hydroxy-2-(5'-methyl-2'-furylmethylamino)-5-pyrimidinyl)-ureido]-2-furylacetamido}-3-[(1-methyl-tetrazol-5-yl)-thiomethyl]-ceph-3-em-4-carboxylate.

EXAMPLE 79

Sodium 7-{D-α-[3-(4-hydroxy-2-(2'-tetrahydro-furylmethylamino)-5-pyrimidinyl)-ureido]-p-hydroxy-phenylacetamido}-3-[(1-methyl-tetrazol-5-yl)-thiomethyl]-ceph-3-em-4-carboxylate Preparation analogous to Example 54, starting from 403 mgm (0.001 mol) of the ureidocarboxylic acid of Example II(q) and 328 mgm (0.001 mol) of 7-amino-[(1-methyltetrazol-5-yl)-thiomethyl]-ceph-3-em-4-carboxylic acid.

Yield of the sodium salt: 426 mgm (58%);
IR-Spectrum: 1770, 1655, 1610, 1550 cm$^{-1}$;
NMR-Spectrum (DMSO+CD$_3$OD) signals at ppm: 1.9 (m,4H), 3.5–4.0 (m,7H), 3.9 (s,3H), 4.40 (q,2H), 4.85 (d,1H), 5.45 (s,1H), 5.65 (d,1H), 6.70 (d,2H), 7.20 (d,2H), 8.0 (s,1H).

EXAMPLE 80

Sodium 7-{D-α-[3-(4-hydroxy-2-(2'-pyrrolylmethylamino)-5-pyrimidinyl)-ureido]-p-hydroxy-phenyl-acetamido}-3-[(1-methyl-tetrazol-5-yl)-thiomethyl]-ceph-3-em-4-carboxylate Preparation analogous to Example 54, starting from 800 mgm (0.002 mol) of the ureidocarboxylic acid of Example II(r) and 656 mgm (0.002 mol) of 7-amino-[(1-methyltetrazol-5-yl)-thiomethyl]-ceph-3-em-4-carboxylic acid.

Yield of the sodium salt: 650 mgm (44.5%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (m,4H), 4.85 (d,1H), 5.45 (s,1H), 5.65 (d,1H), 6.1 (m,2H), 6.75 (d,2H), 7.25 (d,2H), 8.1 (s,1H).

The following cephalosporin was prepared analogously:

Sodium 7-{D-α-[3-(4-hydroxy-2-(2'-pyrrolylmethylamino)-5-pyrimidinyl)-ureido]-p-hydroxy-phenylacetamido}-3-acetoxymethyl-ceph-3-em-4-carboxylate.

EXAMPLE 81

Sodium 7-{D-α-[3-(4-hydroxy-2-(4'-methyl-2'-imidazolylmethylamino)-5-pyrimidinyl)-ureido]-p-hydroxy-phenylacetamido}-3-[(1-methyl-tetrazol-5-yl)-thiomethyl]-ceph-3-em-4-carboxylate Preparation analogous to Example 54, starting from 1.6 gm (0.004 mol) of the ureidocarboxylic acid of Example II(s) and 1.32 gm (0.004 mol) of 7-amino-](1-methyl-tetrazol-5-yl)-thiomethyl]-ceph-3-em-4-carboxylic acid.

Yield of the sodium salt: 1.55 gm (51%);
IR-Spectrum: 1770, 1655, 1610, 1555 cm$^{-1}$;
NMR-Spectrum (DMSO+CD$_3$OD) signals at ppm: 2.1 (s,3H), 3.5 (q,2H), 3.9 (s,3H), 4.40 (m,4H), 4.90 (d,1H), 5.45 (s,1H), 5.70 (d,1H), 6.85 (d,2H), 7.35 (m,4H), 8.05 (s,1H).

The following cephalosporins were prepared analogously:

Sodium 7-{D-α-[3-(4-hydroxy-2-(2'-oxazolylmethylamino)-5-pyrimidinyl)-ureido]-p-hydroxy-phenylacetamido}-3-[(1-methyl-tetrazol-5-yl)-thiomethyl]-ceph-3-em-4-carboxylate; and Sodium 7-{D-α-[3-(4-hydroxy-2-(5'-methyl-2'-triazolylmethylamino)-5-pyrimidinyl)-ureido]-p-hydroxy-phenylacetamido}-3-[(1-methyl-tetrazol-5-yl)-thiomethyl]-ceph-3-em-4-carboxylate.

EXAMPLE 82

Sodium 7-{D-α-[3-(4-hydroxy-2-(5'-methyl-2'-thienylamino)5-pyrimidinyl)-ureido]-p-hydroxy-phenyl-acetamido}-3-acetoxymethyl-ceph-3-em-4-carboxylate Preparation analogous to Example 54, starting from 2.72 gm of 7-amino-cephalosporanic acid (0.01 mol) and 4.15 gm (0.01 mol) of the ureidocarboxylic acid of Example II(u).

Yield of the sodium salt: 3.73 gm (53.5%);
NMR-Spectrum (DMSO+CD$_3$OD) signals at ppm: 2.05 (s,3H), 2.5 (s,3H), 3.45 (q,2H), 4.8 (m,3H), 5.4 (s,1H), 5.65 (d,1H), 6.5 (m,2H), 6.8 (d,2H), 7.25 (d,2H), 8.15 (s,1H).

EXAMPLE 83

Sodium 7-{D-α-[3-(4-hydroxy-2-(5'-methyl-2'-thienylamino)-5-pyrimidinyl)-ureido]-p-hydroxy-phenyl-acetamido}-3-[(1-methyltetrazol-5-yl)-thiomethyl]-ceph-3-em-4-carboxylate Preparation analogous to Example 54, starting from 2.07 gm (0.005 mol) of the ureidocarboxylic acid of Example II(u) and 1.64 gm (0.005 mol) of 7-amino-[(1-methyltetrazol-5-yl)-thiomethyl]-ceph-3-em-4-carboxylic acid.

Yield of the sodium salt: 2.2 gm (59%);
IR-Spectrum: 1765, 1665, 1615, 1555 cm$^{-1}$;
NMR-Spectrum (DMSO+CD$_3$OD) signals at ppm: 2.45 (s,3H), 3.45 (q,2H), 3.9 (s,3H), 4.40 (q,2H), 4.85 (d,1H), 5.45 (s,1H), 5.65 (d,1H), 6.55 (m,2H), 6.85 (d,2H), 7.35 (d,2H), 8.1 (s,1H).

EXAMPLE 84

Sodium 7-{D-α-[3-(4-hydroxy-2-(4'-methyl-2'-thiazolylamino)-5-pyrimidinyl)-ureido]-p-hydroxy-phenyl-acetamido}-3-[(1-methyltetrazol-5-yl)-thiomethyl]-ceph-3-em-4-carboxylate Preparation analogous to Example 54, starting from 1.0 gm (0.0024 mol) of the ureidocarboxylic acid of Example II(u) and 800 mgm (0.0025 mol) of 7-amino-[(1-methyltetrazol-5-yl)-thiomethyl]-ceph-3-em-4-carboxylic acid.

Yield of the sodium salt: 630 mgm (35.5%);
IR-Spectrum: 1765, 1655, 1610, 1550 cm$^{-1}$;
NMR-Spectrum (DMSO+CD$_3$OD) signals at ppm: 2.5 (s,3H), 3.5 (q,2H), 3.9 (s,3H), 4.40 (q,2H), 4.85 (d,1H), 5.45 (s,1H), 5.65 (d,1H), 6.45 (s,1H), 6.80 (d,2H), 7.25 (d,2H), 8.05 (s,1H).

The following cephalosporin was prepared analogously:

Sodium 7-{D-α-[3-(4-hydroxy-2-(2'-thiazolylamino)-5-pyrimidinyl)-ureido]-p-hydroxy-phenyl-acetamido}-3-[(1-methyltetrazol-5-yl)-thiomethyl]-ceph-3-em-4-carboxylate.

EXAMPLE 85

Sodium 7-{D-α-[3-(4-hydroxy-2-(6'-methylsulfinyl-3'-pyridylamino)-5-pyrimidinyl)-ureido]-p-hydroxy-phenylacetamido}-3-acetoxymethyl-ceph-3-em-4-carboxylate Synthesized analogous to Example 54, starting from 7-amino-cephalosporanic acid and the ureidocarboxylic acid of Example II(v).

Yield of the sodium salt: 44%;
IR-Spectrum: 1760, 1655, 1605, 1550 cm$^{-1}$;
NMR-Spectrum (DMSO+CD$_3$OD) signals at ppm: 2.05 (s,3H), 2.7 (s,3H), 3.40 (q,2H), 4.65 (m,2H), 4.85 (d,1H), 5.45 (s,1H), 5.60 (d,1H), 6.70 (d,2H), 7.2 (d,2H), 7.7 (d,1H), 8.25 (s,1H), 8.45 (m,1H), 8.85 (s,1H).

Using the method of Example 54 and the corresponding cephalosporin derivative of the formula V, the cephalosporins of the formula

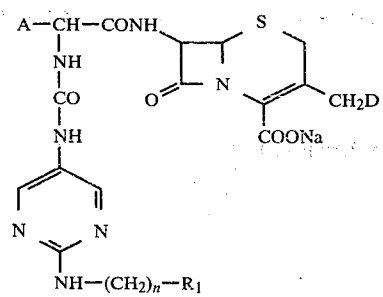

shown in the following table were synthesized:

| Example No. | A | —(CH$_2$)$_n$R$_1$ | D | With the ureidocarboxylic acid of Example 1 | IR-Spectrum (cm$^{-1}$) | NMR-Spectrum (DMSO/CD$_3$OD) signals at ppm |
|---|---|---|---|---|---|---|
| 86 | p-HO—Phenyl | 6-Methylsulfinyl-3-pyridyl | −S−C(=N−N(CH$_3$)−N=N) | II(v) | 1760, 1655, 1605 | 2.75 (s,3H), 3.50 (q,2H), 3.95 (s,3H), 4.30 (m,2H), 4.80 (d,1H), 5.50 (s,1H), 5.65 (d,1H), 6.75 (d,2H), 7.25 (d,2H), 7.7 (d,1H), 8.40 (m,1H), 8.85 (s,1H). |
| 87 | p-HO—Phenyl | 6-Methylsulfinyl-3-pyridyl | −S−C(=N−N(CH$_3$)−N=N) | II(y) | 1765, 1660, 1610 | 3.05 (s,3H), 3.45 (q,2H), 3.90 (s,3H), 4.35 (q,2H), 4.85 (d,1H), 5.45 (s,1H), 5.65 (d,1H), 6.80 (d,2H), 7.30 (d,2H), 7.85 (d,1H), 8.25 (s,1H), 8.6 (d,1H), 8.90 (s,1H). |
| 88 | p-HO—Phenyl | 6-Methylsulfinyl-3-pyridyl | —OCOCH$_3$ | II(y) | 1765, 1660, 1615 | 2.05 (s,3H), 3.10 (s,3H), 3.4 (q,2H), 4.8 (m,3H), 5.45 (s,1H), 5.65 (d,1H), 6.80 (d,2H), 7.30 (d,2H), 7.80 (d,1H), 8.25 (s,1H), 8.65 (d,1H), 8.90 (s,1H). |
| 89 | 2-Thienyl | 6-Methylsulfinyl-3-pyridyl | −S−C(=N−N(CH$_3$)−N=N) | II(x) | 1760, 1655, 1610 | 2.80 (s,3H), 3.45 (q,2H), 3.90 (s,3H), 4.35 (m,2H), 4.85 (dd,1H), 5.5 (dd,1H), 5.65 (broad s,1H), 6.9 (m,2H), 7.35 (m,1H), 7.85 (d,1H), 8.30 (s,1H), 8.6 (d,1H), 8.85 (s,1H). |
| 90 | p-HO—Phenyl | 3-Pyridylmethyl | —OCOCH$_3$ | II(e) | 1760, 1655, 1605 | 2.05 (s,3H), 3.45 (q,2H), 4.05 (s,2H), 4.85 (m,3H), 5.45 (s,1H), 5.60 (d,1H), |

-continued

| Example No. | A | —(CH₂)ₙR₁ | D | With the ureido-carboxylic acid of Example 1 | IR-Spectrum (cm⁻¹) | NMR-Spectrum (DMSO/CD₃OD) signals at ppm |
|---|---|---|---|---|---|---|
| | | | | | | 6.75 (d,2H), 7.35 (m,2 + 1H), 7.7 (m,1H), 8.10 (s,1H), 8.5 (m,2H). |
| 91 | 2-Thienyl | 3-Pyridyl-methyl | 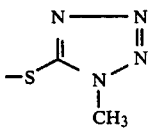 | II(ab) | 1760, 1660, 1610 | 3.40 (q,2H), 3.95 (s,3H), 4.35 (m,2H), 4.45 (m,2H,1H), 5.50 (dd,1H), 5.70 (s,1H), 7.0 (m,2H), 7.3 (m,1H), 7.65 (m,1H), 8.05 (s,1H), 8.45 (m,2H). |
| 92 | 2-Furyl | 3-Pyridyl-methyl | —OCOCH₃ | II(aa) | 1765, 1655, 1615 | 2.05 (s,3H), 3.40 (q,2H), 4.40 (m,2 + 2H), 4.80 (dd,1H), 5.45 (dd,1H), 5.70 (s,1H), 6.3 (m,2H), 7.3 (m,1H), 7.4 (m,1H), 7.7 (m,1H), 8.1 (s,1H), 8.5 (m,2H). |
| 93 | p-HO—Phenyl | 2-Methyl-5-pyrimidinyl | —OCOCH₃ | II(ac) | 1760, 1650, 1610 | 2.05 (s,3H), 2.45 (s,3H), 3.40 (q,2H), 4.35 (m,2H), 4.85 (d,1H), 5.45 (s,1H), 5.55 (d,1H), 6.75 (d,2H), 7.30 (d,2H), 8.30 (s,1H), 9.1 (s,2H). |
| 94 | p-HO—Phenyl | 5-Aminosulfonyl-2-thienyl-methyl | —OCOCH₃ | II(ad) | 1760, 1655, 1610 | 2.05 (s,3H), 3.45 (m,2H), 4.35 (m,2H), 4.60 (s,2H), 4.85 (d,1H), 5.40 (s,1H), 5.55 (d,1H), 6.75 (d,2H), 6.9 (d,1H), 7.25 (d,2H), 7.35 (d,1H), 8.05 (s,1H). |
| 95 | p-HO—Phenyl | 5-Aminosulfonyl-2-thienyl-methyl | 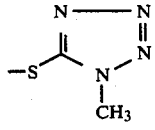 | II(ad) | 1765, 1655, 1610 | 3.40 (m,2H), 3.95 (s,3H), 4.40 (m,2 + 1H), 4.60 (s,2H), 5.40 (s,1H), 5.55 (d,1H), 6.75 (d,2H), 6.95 (d,1H), 7.30 (d,2H), 7.40 (d,1H), 8.05 (s,1H). |
| 96 | p-HO—Phenyl | 5-Aminosulfonyl-2-thienyl-methyl | —OCONH₂ | II(ad) | 1760, 1660, 1610 | 3.40 (q,2H), 4.65 (s,2H), 4.75 (m,2H), 5.45 (s,1H), 5.55 (d,1H), 6.75 (d,2H), 6.9 (d,1H), 7.35 (d,2H), 7.45 (s,1H), 8.05 (s,1H). |
| 97 | p-HO—Phenyl | 5-Aminosulfonyl-2-thienyl-methyl | 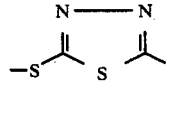 | II(ad) | 1760, 1655, 1605 | 2.75 (s,3H), 3.55 (q,2H), 4.25 (q,2H), 4.60 (s,2H), 4.95 (d,1H), 5.45 (s,1H), 5.60 (d,1H), 6.7 (d,2H), 6.95 (d,1H), 7.25 (d,2H), 7.40 (d,1H), 8.05 (s,1H). |
| 98 | 2-Thienyl | 5-Aminosulfonyl-2-thienyl-methyl | 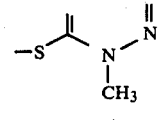 | II(ae) | 1760, 1650, 1605 | 3.45 (q,2H), 4.35 (m,2H), 4.60 (s,2H), 4.95 (dd,1H), 5.50 (m,1H), 5.65 (s,1H), 7.0 (m,3H), 7.4 (m,2H), 8.05 (s,1H). |
| 99 | p-HO—Phenyl | 6-Methyl-sulfinyl-3-pyridyl | 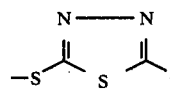 | II(v) | 1760, 1660, 1610 | 2.75 (s,3H), 2.80 (s,3H), 3.50 (q,2H), 4.25 (q,2H), 5.45 (s,1H), 5.60 (d,1H), 6.75 (d,2H), 7.25 (d,2H), 7.7 (d,1H), 8.25 (s,1H), 8.5 (m,1H), 8.9 (s,1H). |
| 100 | p-HO—Phenyl | 6-Methyl-sulfonyl-3-pyridyl | 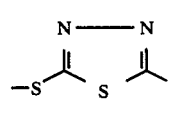 | II(y) | 1760, 1655, 1615 | 2.75 (s,3H), 3.10 (s,3H), 3.55 (q,2H), 4.30 (q,2H), 5.0 (d,1H), 5.50 (s,1H), 5.60 (d,1H), 6.75 (d,2H), 7.25 (d,2H), 7.85 (d,1H), 8.25 (s,1H), 8.55 (m,1H), 8.95 (s,1H). |

| Example No. | A | —(CH$_2$)$_n$R$_1$ | D | With the ureido-carboxylic acid of Example 1 | IR-Spectrum (cm$^{-1}$) | NMR-Spectrum (DMSO/CD$_3$OD) signals at ppm |
|---|---|---|---|---|---|---|
| 101 | p-HO—Phenyl | 5-Amino-carbonyl-2-thienyl | —S—C(=N-N=C(N(CH$_3$))) (1-methyl-tetrazol-5-yl-thio) | II(af) | 1760, 1660, 1600 | 3.50 (q,2H), 3.95 (s,3H), 4.30 (m,2H), 4.95 (d,1H), 5.40 (s,1H), 5.55 (d,1H), 6.6 (d,1H), 6.75 (d,2H), 7.25 (d,2H), 7.45 (d,1H), 8.40 (s,1H). |
| 102 | p-HO—Phenyl | 5-Amino-carbonyl-2-thienyl | —OCOCH$_3$ | II(af) | 1765, 1665, 1620 | 2.05 (s,3H), 3.40 (q,2H), 4.80 (m,2H), 4.90 (d,1H), 5.45 (s,1H), 5.55 (d,1H), 6.65 (d,1H), 6.75 (d,2H), 7.25 (d,2H), 7.40 (d,1H), 8.35 (s,1H). |
| 103 | 2-Thienyl | 5-Amino-carbonyl-2-thienyl | 1-methyl-tetrazol-5-yl-thio | II(ag) | 1760, 1660, 1610 | 3.45 (q,2H), 3.95 (s,3H), 4.30 (m,2H), 4.95 (dd,1H), 5.50 (dd,1H), 5.60 (s,1H), 6.65 (d,1H), 7.0 (m,2H), 7.4 (m,2H), 8.35 (s,1H). |
| 104 | p-HO—Phenyl | 6-Hydroxy-3-pyridyl | 1-methyl-tetrazol-5-yl-thio | II(z) | 1760, 1660, 1615 | 3.40 (q,2H), 3.95 (s,3H), 4.30 (m,2H), 4.90 (d,1H), 5.45 (s,1H), 5.55 (d,1H), 6.45 (d,1H), 6.75 (d,2H), 7.25 (d,2H), 7.6 (d,1H), 7.9 (s,2H), 8.20 (s,1H). |
| 105 | p-HO—Phenyl | 6-Hydroxy-3-pyridyl | —OCOCH$_3$ | II(z) | 1765, 1665, 1610 | 2.05 (s,3H), 3.50 (q,2H), 4.80 (m,3H), 5.40 (s,1H), 5.55 (d,1H), 6.50 (d,1H), 6.80 (d,2H), 7.30 (d,2H), 7.6 (d,1H), 7.9 (s,2H), 8.20 (s,1H). |
| 106 | p-HO—Phenyl | 6-Hydroxy-3-pyridyl | —S—C(=N)—S—C(CH$_3$)=N— (4-methyl-thiazol-2-yl-thio) | II(z) | 1760, 1660, 1610 | 2.70 (s,3H), 3.50 (m,2H), 4.25 (q,2H), 4.95 (d,1H), 5.45 (s,1H), 5.55 (d,1H), 6.40 (d,1H), 6.75 (d,2H), 7.30 (d,2H), 7.6 (d,1H), 7.95 (s,2H), 8.20 (s,1H). |
| 107 | p-HO—Phenyl | 2-Hydroxy-5-pyrimidinyl | —OCOCH$_3$ | II(ah) | 1765, 1660, 1615 | 2.05 (s,3H), 3.45 (m,2H), 4.85 (m,2 + 1H), 5.50 (s,1H), 5.60 (d,1H), 6.80 (d,2H), 7.30 (d,2H), 8.35 (s,1H), 8.70 (s,2H). |
| 107(a) | p-HO—Phenyl | 2-Hydroxy-5-pyrimidinyl | 1-methyl-tetrazol-5-yl-thio | II(ah) | 1760, 1660, 1610 | 3.40 (q,2H), 3.90 (s,3H), 4.30 (m,2H), 4.95 (d,1H), 5.40 (s,1H), 5.50 (d,1H), 6.75 (d,2H), 7.25 (d,2H), 8.30 (s,1H), 8.70 (s,2H). |
| 108 | p-HO—Phenyl | 2,4-Dihydroxy-5-pyrimidinyl | 1-methyl-tetrazol-5-yl-thio | II(ai) | 1760, 1650, 1600 | 3.45 (m,2H), 3.95 (s,3H), 4.35 (m,2H), 4.90 (d,1H), 5.45 (s,1H), 5.50 (d,1H), 6.70 (d,2H), 7.20 (d,2H), 8.30 (s,1H), 8.50 (s,1H). |
| 109 | p-HO—Phenyl | 2,6-Dihydroxy-4-pyrimidinyl | 1-methyl-tetrazol-5-yl-thio | II(ak) | 1760, 1660, 1605 | 3.40 (m,2H), 3.90 (s,3H), 4.30 (m,2H), 4.95 (d,1H), 5.40 (s,1H), 5.50 (d,1H), 6.70 (d,2H), 7.25 (d,2H), 8.35 (s,1H), 8.45 (s,1H). |
| 110 | p-HO—Phenyl | 2,6-Dihydroxy-4-pyrimidinyl | —OCOCH$_3$ | II(ak) | 1760, 1655, 1610 | 2.05 (s,3H), 3.50 (m,2H), 4.85 (m,3H), 5.40 (s,1H), 5.50 (d,1H), 6.75 (d,2H), 7.30 (d,2H), 8.30 (s,1H), 8.50 (s,1H). |

-continued

| Example No. | A | —(CH$_2$)$_n$R$_1$ | D | With the ureido-carboxylic acid of Example 1 | IR-Spectrum (cm$^{-1}$) | NMR-Spectrum (DMSO/CD$_3$OD) signals at ppm |
|---|---|---|---|---|---|---|
| 111 | p-HO—Phenyl | 4,6-Dihydroxy-2-pyrimidinyl | —S—C(=N-N)N(CH$_3$)—N (thiadiazole ring with CH$_3$) | II(al) | 1765, 1660, 1610 | 3.45 (m,2H), 3.90 (s,3H), 4.30 (m,2H), 4.90 (d,1H), 5.40 (s,1H), 5.50 (d,1H), 6.75 (d,2H), 7.35 (d,2H), 8.35 (s,1H), 8.80 (s,1H). |
| 112 | p-HO—Phenyl | 4,6-Dihydroxy-2-pyrimidinyl | —OCOCH$_3$ | II(al) | 1760, 1655, 1610 | 2.10 (s,3H), 3.45 (m,2H), 4.80 (m,2H + d,1H), 5.45 (s,1H), 5.55 (d,1H), 6.75 (d,2H), 7.30 (d,2H), 8.35 (s,1H), 8.75 (s,1H). |

EXAMPLE 113

Sodium 7-{D-α-[3-(4-hydroxy-2-(3'-pyridylamino)-5-pyrimidinyl)-ureido]-phenyl-acetamido}-3-methyl-ceph-3-em-4-carboxylate A suspension of 2.66 gm of cefalexin monohydrate (0.0073 mol) in 80 ml of tetrahydrofuran and 20 ml of water was dissolved in triethylamine while cooling with ice (solution A). 1.48 gm (0.0073 mol) of 5-amino-4-hydroxy-2-(3'-pyridylamino)-pyrimidine were dissolved in tetrahydrofuran, the solution was admixed with 1 ml of triethylamine, and the mixture was added, while cooling with ice, to a solution of 750 mgm of phosgene in 18 ml of tetrahydrofuran. The resulting mixture was evaporated to 40 ml in vacuo and added, while cooling with ice, to solution A. The pH value was kept at 7.5 with triethylamine. The solution thus obtained was stirred for one hour at 5° C. and for another hour at room temperature. After this time the tetrahydrofuran was removed in vacuo, the residue was diluted with 20 ml of water, and the aqueous mixture was shaken twice with ethyl acetate. The aqueous phase was then covered with ethyl acetate and slowly adjusted to a pH of 2.9 while cooling and stirring. The ethyl acetate layer was separated, the aqueous phase was shaken once again with ethyl acetate, the two organic phases were combined, and the solvent was distilled off in vacuo. The sodium salt was prepared in conventional manner.

Yield: 2.94 gm (68%);
IR-Spectrum: 1765, 1655, 1610, 1540 cm$^{-1}$;
NMR-Spectrum (DMSO+CD$_3$OD) signals at ppm: 2.0 (s,3H), 3.40 (q,2H), 5.05 (d,1H), 5.45 (s,1H), 5.65 (d,1H), 7.45 (m,6H), (m,3H), 8.75 (s,1H).

Using a procedure analogous to that described in Example 113, but substituting the p-hydroxy analog of cefalexin monohydrate and the reaction product of the indicated pyrimidine derivative with phosgene, the following cephalosporins were obtained:

EXAMPLE 114

Sodium 7-{D-α-[3-(4-hydroxy-2-(3'-pyridylmethylamino)-5-pyrimidinyl)-ureido]-p-hydroxyphenyl-acetamido}-3-methylceph-3-em-4-carboxylate With the reaction product of 5-amino-4-hydroxy-2-(3'-pyridylmethylamino)-pyrimidine and phosgene:
Yield: 71%
IR-Spectrum: 1765, 1660, 1610, 1540 cm$^{-1}$;
NMR-Spectrum (DMSO+CD$_3$OD) signals at ppm: 2.0 (s,3H), 3.4 (q,2H), 4.5 (s,2H), 4.95 (d,1H), 5.45 (s,1H), 5.60 (d,1H), 6.8 (d,2H), 7.3 (m,3H), 7.7 (m,1H), 8.1 (s,1H), 8.5 (m,2H).

EXAMPLE 115

Sodium 7-{D-α-[3-(4-hydroxy-2-(2'-thienylmethylamino)-5-pyrimidinyl)-ureido]-p-hydroxyphenyl-acetamido}-3-methyl-ceph-3-em-4-carboxylate With the reaction product of 5-amino-4-hydroxy-2-(3'-pyridylmethylamino)-pyrimidine and phosgene:
Yield: 64%;
IR-Spectrum: 1770, 1660, 1610, 1550 cm$^{-1}$;
NMR-Spectrum (DMSO+CD$_3$OD) signals at ppm: 2.05 (s,3H), 3.4 (q,2H), 4.5 (s,2H), 4.95 (d,1H), 5.45 (s,1H), 5.65 (d,1H), 6.70 (d,2H), 6.85 (m,2H), 7.25 (d,2H), 7.35 (m,1H), 8.05 (s,1H.

EXAMPLE 116

Sodium 7-{D-α-[3-(4-hydroxy-2-(2'-furylmethylamino)-5-pyrimidinyl)-ureido]-p-hydroxyphenyl-acetamido}-3-methyl-ceph-3-em-4-carboxylate With the reaction product of 5-amino-4-hydroxy-2-(2-'-furylmethylamino)-pyrimidine and phosgene:
Yield: 71%;
IR-Spectrum: 1765, 1655, 1610, 1545 cm$^{-1}$;
NMR-Spectrum (DMSO+CD$_3$OD) signals at ppm: 2.0 (s,3H), 3.35 (q,2H), 4.4 (s,2H), 4.95 (d,1H), 5.4 (s,1H), 5.65 (d,1H), 6.3 (m,2H), 6.7 (d,2H), 7.2 (d,2H), 7.5 (s,1H), 8.05 (s,1H).

EXAMPLE 117

Sodium 7-{D-α-[3-(4-hydroxy-2-(3'-pyridylamino)-5-pyrimidinyl)-ureido]-phenyl-acetamido}-3-acetoxymethylceph-3-em-4-carboxylate 2.03 gm (0.01 mol) of 5-amino-4-hydroxy-2-(3'-pyridylamino)-pyrimidine were dissolved in tetrahydrofuran, the solution was admixed with 1.35 ml of triethylamine, and the mixture was added, while cooling with ice, to a solution of 1.0 gm of phosgene in tetrahydrorfuran. The resulting mixture was reacted, as described in Example 113, with 4.25 gm (0.01 mol) of cephaloglycin dihydrate. The reaction mixture was worked up as described in Example 113, except that the desired end product was precipitated from water at pH 3.0.

Yield: 3.16 gm of the sodium salt (48.5%);

NMR-Spectrum (DMSO+CD$_3$OD) signals at ppm: 2.05 (s,3H), 3.45 (q,2H), 4.85 (m,3H), 5.45 (s,1H), 5.65 (d,1H), 7.45 (m,6H), 8.25 (m,3H), 8.75 (s,1H).

Using a procedure analogous to that described in Example 117, but substituting cephaloglycin dihydrate and the reaction product of the indicated pyrimidine derivative with phosgene, the following cephalosporins were obtained:

EXAMPLE 118

Sodium 7-{D-α-[3-(4-hydroxy-2-(2'-thienylmethylamino)-5-pyrimidinyl)-ureido]-phenyl-acetamido}-3-acetoxymethyl-ceph-3-em-4-carboxylate With the reaction product of 5-amino-4-hydroxy-2-(2'-thienylmethylamino)-pyrimidine and phosgene:

Yield: 62.5%;

IR-Spectrum: 1765, 1655, 1610, 1540 cm$^{-1}$;

NMR-Spectrum (DMSO+CD$_3$OD) signals at ppm: 2.05 (s,3H), 3.4 (q,2H), 4.45 (s,2H), 4.85 (m,3H), 5.45 (s,1H), 5.60 (d,1H), 6.85 (m,2H), 7.45 (m,6H), 8.1 (s,1H).

EXAMPLE 119

Sodium 7-{D-α-[3-(4-hydroxy-2-(2'-furylmethylamino)-5-pyrimidinyl)-ureido]-phenyl-acetamido}-3-acetoxymethyl-ceph-3-em-4-carboxylate With the reaction product of 5-amino-4-hydroxy-2-(2'-furylmethylamino)-pyrimidine and phosgene:

Yield: 64%;

IR-Spectrum: 1770, 1660, 1610, 1550 cm$^{-1}$;

NMR-Spectrum (DMSO+CD$_3$OD) signals at ppm: 2.05 (s,3H), 3.45 (q,2H), 4.45 (s,2H), 4.85 (m,2+1H), 5.45 (s,1H), 5.65 (d,1H), 6.3 (m,2H), 7.5 (m,6H), 8.05 (s,1H).

EXAMPLE 120

Sodium 7-{D-α-[3-(4-hydroxy-2-(4'-methyl-2'-thiazolylmethylamino)-5-pyrimidinyl)-ureido]-p-hydroxy-phenylacetamido}-3-[(1-methyl-tetrazol-5-yl)-thiomethyl]-ceph-3em-4-carboxylate Preparation analogous to Example 113, starting from 405 mgm of 7-[D-α-amino-(p-hydroxyphenylacetamido)]-3-[(1-methyl-tetrazol-5-yl)-thiomethyl]-ceph-3-em-4-carboxylic acid (0.001 mol) and the reaction product of 240 mgm of 5-amino-4-hydroxy-2-(4'-methyl-2'-thiazolylmethylamino)-pyrimidine (0.001 mol) with phosgene. During the work-up the resulting cephalosporin was precipitated from water at pH 2.9, suction-filtered off, dried and converted into the sodium salt in known manner.

Yield: 315 mgm (45.5%);

IR-Spectrum: 1765, 1655, 1610, 1540 cm$^{-1}$;

NMR-Spectrum (DMSO+CD$_3$OD) signals at ppm: 2.45 (s,3H), 3.5 (q,2H), 3.9 (s,3H), 4.35 (q,2H), 4.85 (d,1H), 5.45 (s,1H), 5.65 (d,1H), 6.15 (s,1H), 6.85 (d,2H), 7.35 (d,2H), 8.05 (s,1H).

The following cephalosporins were synthesized analogously:

Sodium 7-{D-α-[3-(4-hydroxy-2-(3'-pyridylmethylamino)-5-pyrimidinyl)-ureido]-2-furyl-acetamido}-3-acetoxy-methyl-ceph-3-em-4-carboxylate;

Sodium 7-{D-α-[3-(4-hydroxy-2-(3'-pyridylmethylamino)-5-pyrimidinyl)-ureido]-2-thienyl-acetamido}-3-acetoxy-methyl-ceph-3-em-4-carboxylate;

Sodium 7{D-α-[3-(4-hydroxy-2-(3'-pyridylmethylamino)-5-pyrimidinyl)-ureido]-3-furyl-acetamido}-3-acetoxy-methyl-ceph-3-em-4-carboxylate; and Sodium 7-{D-α-[3-(4-hydroxy-2-(3'-pyridylmethylamino)-5-pyrimidinyl)-ureido]-phenyl-acetamido}-3-acetoxy-methyl-ceph-3-em-4-carboxylate.

EXAMPLE 121

Sodium 7-{D-α-[3-(4-hydroxy-2-(5'-methyl-2'-thiadiazolylamino)-5-pyrimidinyl)-ureido]-p-hydroxyphenyl-acetamido}-3-[(1-methyl-tetrazol-5-yl)-thiomethyl]-ceph-3-em-4-carboxylate 1.14 gm (0.005 mol) of 5-amino-4-hydroxy-2-(5'-methyl-2'-thiadiazolylamino)-pyrimidine were suspended in 50 ml of tetrahydrofuran, and the susepsnion was treated until dissolution with trimethylsilyl-diethylamine. Some insoluble material was filtered off in an atmosphere of nitrogen, the tetrahydrofuran was distilled off, and the residue was evaporated to dryness in a high vacuum. The residual product was dissolved in 30 ml of tetrahydrofuran, and the solution was added, while cooling with ice, to a solution of 500 mgm of phosgene in tetrahydrofuran. Subsequently, nitrogen is blown through the solution to remove unreacted phosgene. The further reaction with 7-[D-α-amino-p-hydroxyphenyl-acetamido]-3-[(1-methyl-tetrazol-5-yl)-thiomethyl]-ceph-3-em-4-carboxylic acid was carried out analogously to Example 92.

Yield: 980 mgm (28.5%) of the sodium salt;

IR-Spectrum: 1765, 1665, 1605, 1545 cm$^{-1}$;

NMR-Spectrum (DMSO+CD$_3$OD) signals at ppm: 2.45 (s,3H); 3.5 (q,2H), 3.9 (s,3H), 4.35 (q,2H), 4.85 (d,1H), 5.40 (s,1H), 5.60 (d,1H), 6.80 (d,2H), 7.25 (d,2H), 8.05 (s,1H).

The following cephalosporin was prepared analogously:

Sodium 7-{d-α-[-(4-hydroxy-2-(5'-methyl-2'-triazolylamino)-5-pyrimidinyl)-ureido]-p-hydroxy-phenyl-acetamido}-3-[(1-methyl-tetrazol-5-yl)-thiomethyl]-ceph-3-em-4-carboxylate

EXAMPLE 122

Sodium 7-{D-α-[-(4-hydroxy-2-(2'-thienylmethylamino)-5-pyrimidinyl)-ureido]-p-hydroxy-phenyl-acetamido}-3-acetoxymethyl-ceph-3-em-4-carboxylate This cephalosporin was prepared analogous to Example 113, starting from 810 mgm of 7-(D-α-amino-p-hydroxy-phenylacetamido)-3-acetoxy-methyl-ceph-3-em-4-carboxylate (0.002 mol) and the reaction product of 440 mgm of 5-amino-4-hydroxy-2-(2'-thienylmethylamino)-pyrimidine (0.002 mol) with 200 mgm of phosgene. The reaction mixture was worked up analogous to Example 92.

Yield: 615 mgm of the sodium salt (44.5%);

IR-Spectrum: 1765, 1660, 1540 cm$^{-1}$;

NMR-Spectrum (DMSO+CD$_3$OD) signals at ppm: 2.05 (2,3H), 3.35 (q,2H), 4.45 (s,2H), 4.80 (m,2+1H), 5.45 (s,1H), 5.65 (d,1H), 6.7 (d,2H), 6.8 (m,2H), 7.30 (d,2H), 7.45 (m,1H), 8.05 (s,1H).

The following cephalosporins were prepared analogously:

Sodium 7-55 D-α-[3-(4-hydroxy-2-(2'-furylmethylamino)-5-pyrimidinyl)-ureido]-m,p-dihydroxy-phenyl-acetamido}-3-acetoxy-methyl-ceph-3-em-4-carboxylate;

Sodium 7-{D-α-[3-(4-hydroxy-2-(2'-furylmethylamino)-5-pyrimidinyl)-ureido]-m,p-dihydroxy-phenyl-acetamido}-3-carbamoyloxymethyl-ceph-3-em-4-carboxylate;

Sodium 7-{D-α-[3-(4-hydroxy-2-(2'-furylmethylamino)-5-pyrimidinyl)-ureido]-m,p-dihydroxy-phenyl-acetamido}-3-[(1-methyl-tetrazol-5-yl)-thiomethyl]-ceph-3-em-4-carboxylate;

Sodium 7-{D-α-[3-(4-hydroxy-2-(3'-furylmethylamino)-5-pyrimidinyl)-ureido]-p-hydroxy-phenyl-acetamido}-3-acetoxymethyl-ceph-3-em-4-carboxylate;

Sodium 7-{D-α-[3-(4-hydroxy-2-(2'-furylmethylamino)-5-pyrimidinyl)-ureido]-m,p-dihydroxy-phenyl-acetamido}-3-[(1-methyl-tetrazol-5-yl)-thiomethyl]-ceph-3-em-4-carboxylate; and Sodium 7-{D-α-[3-(4-hydroxy-2-(5'-nitro-2'-furylmethylamino)-5-pyrimidinyl)-ureido]-p-hydroxy-phenyl-acetamido}-3-[(1-methyl-tetrazol-5-yl)-thiomethyl]-ceph-3-em-4-carboxylate.

EXAMPLE 123

Sodium 7-{D-α-[3-(4-hydroxy-2-(5'-pyrimidinyl-amino)-5-pyrimidinyl)-ureido]-p-hydroxy-phenyl-acetamido}-3-[(1-methyltetrazol-5-yl)-thiomethyl]-ceph-3-em-4-carboxylate Preparation analogous to Example 84, starting from 5-amino-4-hydroxy-2-(5'-pyrimidinylamino)-pyrimidine and the cephalosporin derivative of Example 93.

Yield of the sodium salt: 260 mgm (35.5%);
IR-Spectrum: 1765, 1655, 1610, 1550 cm$^{-1}$;
NMR-Spectrum (DMSO+CD$_3$OD) signals at ppm: 3.5 (q,2H), 3.9 (s,3H), 4.40 (q,2H), 4.85 (d,1H), 5.45 (s,1H), 5.65 (d,1H), 6.85 (d,2H), 7.35 (d,2H), 8.0 (s,1H), 8.3 (broad s,2H), 8.8 (s,1H).

EXAMPLE 124

Sodium 7-{D-α-[3-(4-hydroxy-2-(3'-pyridylamino)-5-pyrimidinyl)-ureido]-p-hydroxy-phenyl-acetamido}-3-[(1,2,3-triazol-4-yl)-thiomethyl]-ceph-3-em-4-carboxylate 680 mgm of the cephalosporin derivative obtained in Example 44 were dissolved in 10 ml of a phosphoric acid buffer solution of pH 6.3. 100 mgm of 4-mercapto-1,2-3-triazole were added to this solution, and the mixture was heated for 6 hours at 70° C. in an atmosphere of nitrogen, the pH value being maintained at 6.0 to 6.5. After this time, the reaction mixture was cooled and extracted twice with ethyl acetate. Subsequently, 2 N hydrochloric acid was added, while cooling, until the solution has a pH of 2.9. The precipitated product was suction-filtered off, washed with a little water and dried. The residue was converted into the sodium salt in conventional manner.

Yield: 460 mgm (64%);
IR-Spectrum: 1765, 1660, 1615, 1545 cm$^{-1}$;
NMR-Spectrum (DMSO+CD$_3$OD) signals at ppm: 3.5 (q,2H), 4.25 (q,2H), 4.90 (d,1H), 5.45 (s,1H), 5.60 (d,1H), 6.8 (d,2H), 7.25 (d,2H), 7.4 (m,1H), 7.95 (s,1H), 8.25 (m,3H), 8.75 (s,1H).

EXAMPLE 125

Sodium 7-{D-α-[3-(4-hydroxy-2-(3'-pyridylmethylamino)-5-pyrimidinyl)-ureido]-p-hydroxy-phenyl-acetamido}-3-[(2-methyl-1,3,4-thiadiazol-5-yl)-thiomethyl]-ceph-3-em-4-carboxylate Preparation analogous to Example 124, starting from 685 mgm of the corresponding acetoxycephalosporin derivative (0.001 mol), which was reacted with 135 mgm of 5-mercapto-2-methyl-1,3,4-thiadiazole.

Yield: 455 mgm (65%) of the sodium salt;
IR-Spectrum: 1765, 1670, 1615, 1550 cm$^{-1}$;
NMR-Spectrum (DMSO+CD$_3$OD) signals at ppm: 2.7 (s,3H), 3.55 (q,2H), 4.45 (s,2H), 4.95 (d,1H), 5.45 (s,1H), 5.65 (d,1H), 6.85 (d,2H), 7.35 (m,3H), 7.7 (m,1H), 8.1 (s,1H), 8.45 (m,2H).

EXAMPLE 126

Sodium 7-{D-α-[3-(4-hydroxy-2-(3'-pyridylmethylamino)-5-pyrimidinyl)-ureido]-2-furyl-acetamido}-3-[(1-methyl-tetrazol-5-yl)-thiomethyl]-ceph-3-em-4-carboxylate Preparation analogous to Example 124, starting from sodium 7-{D-α-[3-(4-hydroxy-2-(4'-pyridylmethylamino)-5-pyrimidinyl)-ureido]-2-furyl-acetamido}-3-acetoxymethyl-ceph-3-em-4-carboxylate by reaction with 1-methyl-5-mercaptotetrazole.

Yield: 66.5%.

EXAMPLE 127

Sodium 7-{D-α-[3-(4-hydroxy-2-(2'-thienylmethylamino)-5-pyrimidinyl)-ureido]-p-hydroxy-phenyl-acetamido}-3-[(1,3,4-thiadiazol-2-yl)-thiomethyl]-ceph-3-em-4-carboxylate Preparation analogous to Example 124, by reacting the cephalosporin derivative obtained in Example 122 with 2-mercapto-1,3,4-thiadiazole.

Yield: 71%.

EXAMPLE 128

Sodium 7-{D-α-[3-(4-hydroxy-2-(2'-thienylmethylamino)-5-pyrimidinyl)-ureido]-p-hydroxy-phenyl-acetamido}-3-[(2-acetylamino-thiadiazol-5-yl)-thiomethyl]-ceph-3-em-4-carboxylate Prepared analogous to Example 124 from 690 mgm of the cephalosporin derivative of Example 122 (0.001 mol) and 175 mgm of 2-acetylamino-5-mercapto-1,3,4-thiadiazole.

Yield: 480 mgm (59%) of the sodium salt;
IR-Spectrum: 1765, 1655, 1620, 1540 cm$^{-1}$;
NMR-Spectrum (DMSO+CD$_3$OD) signals at ppm: 2.4 (s,3H), 3.70 (q,2H), 4.25 (q,2H), 4.45 (s,2H), 4.95 (d,1H), 5.45 (s,1H), 5.65 (d,1H), 6.7-7.45 (m,7H), 8.05 (s,1H).

EXAMPLE 129

Sodium
7-{D-α-[3-(4-hydroxy-2-(2'-thienylmethylamino)-5-pyrimidinyl)-ureido]-p-hydroxy-phenyl-acetamido}-3-[(2-methylamino-thiadiazol-5-yl)-thiomethyl]-ceph-3-em-4-carboxylate Prepared analogous to Example 96 from the same cephalosporin derivative by reaction with 2-methylamino-5-mercapto-1,3,4-thiadiazole.
Yield: 61%.

EXAMPLE 130

Sodium
7-{D-α-[3-(4-hydroxy-2-(2'-thienylmethylamino)-5-pyrimidinyl)-ureido]-p-hydroxy-phenyl-acetamido}-3-[(1,3,4-triazol-4-yl)-thiomethyl]-ceph-3-em-4-carboxylate Prepared analogous to Example 96 from the same cephalosporin derivative by reaction with 4-mercapto-1,3,4-triazole. Yield: 68%.

Analogous to Example 96 the following cephalosporins were prepared starting from sodium 7-{D-α-[3-(4-hydroxy-2-(2'-furylmethylamino)-5-pyrimidinyl)-ureido]-p-hydroxy-phenyl-acetamido}-3-acetoxymethyl-ceph-3-em-4-carboxylate.

EXAMPLE 131

Sodium
7-{D-α-[3-(4-hydroxy-2-(2'-furylmethylamino)-5-pyrimidinyl)-ureido]-p-hydroxy-phenyl-acetamido}-3-[(tetrazol-5-yl)-thiomethyl]ceph-3-em-4-carboxylate By reaction with 5-mercapto-tetrazole.
Yield: 57%.
IR-Spectrum: 1770, 1655, 1615, 1545 cm$^{-1}$;
NMR-Spectrum (DMSO+CD$_3$OD) signals at ppm: 3.45 (q,2H), 4.45 (m,4H), 4.90 (d,1H), 5.45 (s,1H), 5.60 (d,1H), 6.3 (m,2H), 6.7 (d,2H), 7.2 (d,2H), 7.5 (s,1H), 8.05 (s,1H).

EXAMPLE 132

Sodium
7-{D-α-[3-(4-hydroxy-2-(2'-thienylmethylamino)-5-pyrimidinyl)-ureido]-p-hydroxy-phenyl-acetamido}-3-[(1,2,4-thiadiazol-5-yl)-thiomethyl]-ceph-3-em-4-carboxylate By reaction with 5-mercapto-1,2,4-thiadiazole.
Yield: 64.5%.

EXAMPLE 133

Sodium
7-{D-α-[3-(4-hydroxy-2-(2'-furylmethylamino)-5-pyrimidinyl)-ureido]-p-hydroxy-phenyl-acetamido}-3-[(2-acetylamino-1,3,4-thiadiazol-5-yl)-thiomethyl]ceph-3-em-4-carboxylate By reaction with 2-acetylamino-1,3,4-thiadiazole.
Yield: 56%;
NMR-Spectrum (DMSO+CD$_3$OD) signals at ppm: 2.45 (s,3H), 3.70 (q,2H), 4.3–4.4 (m,4H) (partly masked by solvent), 4.95 (d,1H), 5.45 (s,1H), 5.60 (d,1H), 6.3 (m,2H), 6.7 (d,2H), 7.2 (d,2H), 7.5 (s,1H), 8.05 (s,1H).

EXAMPLE 134

Sodium
7-{D-α-[3-(4-hydroxy-2-(2'-furylmethylamino)-5-pyrimidinyl)-ureido]-p-hydroxy-phenyl-acetamido}-3-[(1,3,4-triazol-2-yl)-thiomethyl]ceph-3-em-4-carboxylate By reaction with 2-mercapto-1,3,4-triazole.
Yield: 66%.
NMR-Spectrum (DMSO+CD$_3$OD) signals at ppm: 3.50 (q,2H), 4.4 (m,4H), 4.90 (d,1H), 5.40 (s,1H), 5.65 (d,1H), 6.35 (m,2H), 6.7 (d,2H), 7.2 (d,2H), 7.55 (s,1H), 8.05 (s,1H), 8.35 (s,1H).

EXAMPLE 135

Sodium
7-{D-α-[3-(4-hydroxy-2-(2'-furylmethylamino)-5-pyrimidinyl)-ureido]-p-hydroxy-phenyl-acetamido}-3-[(2-dimethylamino-1,3,4-thiadiazol-5-yl)-thiomethyl]-ceph-3-em-4-carboxylate By reaction with 2-dimethylamino-5-mercapto-1,3,4-thiadiazole.
Yield: 60%.
NMR-Spectrum (DMSO+CD$_3$OD) signals at ppm: 3.05 (d,6H), 3.50 (q,2H), 4.35 (q,2H), 4.45 (s,2H), 5.0 (d,1H), 5.70 (d,1H), 6.30 (m,2H), 6.7 (d,2H), 7.2 (d,2H), 7.55 (s,1H), 8.05 (s,1H).

EXAMPLE 136

Sodium
7-{D-α-[3-(4-hydroxy-2-(2'-furylmethylamino)-5-pyrimidinyl)-ureido]-p-hydroxy-phenyl-acetamido}-3-[(2-methyl-1,3,4-oxadiazol-5-yl)-thiomethyl]ceph-3-em-4-carboxylate By reaction with 2-methyl-5-mercapto-1,3,4-oxadiazole.
Yield: 63.5%.
NMR-Spectrum (DMSO+CD$_3$OD) signals at ppm: 2.45 (s,3H), 3.6 (q,2H), 4.2 (2H), 4.45 (s,2H), 4.95 (d,1H), 5.45 (s,1H), 5.60 (d,1H), 6.35 (m,2H), 6.8 (d,2H), 7.25 (d,2H), 7.5 (s,1H), 8.05 (s,1H).

EXAMPLE 137

Pivaloyloxymethyl
7-{D-α-[3-(4-hydroxy-2-(3'-pyridylamino)-5-pyrimidinyl)-ureido]-p-hydroxy-phenyl-acetamido}-3-[1-methyl-tetrazol-5-yl)-thiomethyl]-ceph-3-em-4-carboxylate A solution of 965 mgm (0.0013 mol) of the end product of Example 45 and 325 mgm of pivaloyloxymethyl iodide in 15 ml of dimethylformamide was stirred for one hour at room temperature. Subsequently, 50 ml of ethyl acetate and 50 ml of 0.1 M sodium bicarbonate solution were added thereto. The ethyl acetate layer was dried successively with water, dilute hydrochloric acid and magnesium sulfate, and was then evaporated to dryness in vacuo. The residue was stirred with anhydrous ether and suction-filtered off.
Yield: 710 mgm (66%);
IR-Spectrum: 1775, 1735 cm$^{-1}$;
NMR-Spectrum (CDCL$_3$+CD$_3$OD) signals at ppm: 1.10 (s,9H), 3.6 (m,2H), 4.0 (s,3H), 4.5 (m,2H), 4.95 (d,1H), 5.5 (s,1H), 5.75 (d,1H), 5.85 (dd,2H), 6.85 (d,2H), 7.3 (d,2H), 7.45 (m,1H), 8.3 (m,3H), 8.75 (s,1H).

The following cephalosporin was prepared analogously:

Pivaloyloxymethyl 7-{D-α-[3-(4-hydroxy-2-(3'-pyridylmethylamino)-5-pyrimidinyl)-ureido]-p-hydroxy-phenyl-acetamido}-3-[1-methyl-tetrazol-5-yl)-thiomethyl]-ceph-3-em-4-carboxylate.

EXAMPLE 138

Pivaloyloxymethyl 7-{D-α-[3-(4-hydroxy-2-(2'-thienylmethylamino)-5-pyrimidinyl)-ureido]-p-hydroxy-phenyl-acetamido}-3-[1-methyl-tetrazol-5-yl)-thiomethyl]-ceph-3-em-4-carboxylate Preparation analogous to Example 109, starting from 3.75 gm of the end product of Example 62, which was reacted with 1.2 gm of pivaloyloxymethyl iodide.

Yield: 2.79 gm (68%);

IR-Spectrum: 1770, 1740 cm$^{-1}$;

NMR-Spectrum (CDCl$_3$+CD$_3$OD) signals at ppm: 1.10 (s,9H), 3.55 (q,2H), 3.95 (s,3H), 4.45 (m,4H), 4.95 (d,1H), 5.55 (s,1H), 5.65 (d,1H), 5.8 (dd,2H), 6.65–7.35 (m,7H), 8.05 (s,1H).

The following cephalosporin was prepared analogously:

Propionyloxy-1-ethyl-1 7-{D-α-[3-(4-hydroxy-2-(2'-thienylmethylamino)-5-pyrimidinyl)-ureido]-p-hydroxy-phenylacetamido}-3-[(1-methyl-tetrazol-5-yl)-thiomethyl]-ceph-3-em-4-carboxylate.

EXAMPLE 139

Pivaloyloxymethyl 7-{D-α-[3-(4-hydroxy-2-(2'-furylmethylamino)-5-pyrimidinyl)-ureido]-p-hydroxy-phenyl-acetamido}-3-[1-methyl-tetrazol-5-yl)-thiomethyl]-ceph-3-em-4-carboxylate Preparation analogous to Example 109, starting from 735 mgm of the end product of Example 64, which was reacted with 220 mgm of pivaloyloxymethyl iodide.

Yield: 500 mgm (61%).

IR-Spectrum: 1770, 1740 cm$^{-1}$;

NMR-Spectrum (CDCl$_3$+CD$_3$OD) signals at ppm: 1.05 (s,9H), 3.55 (q,2H), 3.95 (s,3H), 4.45 (m,4H), 4.95 (d,1H), 5.55 (s,1H), 5.65 (d,1H), 5.75 (dd,2H), 6.3 (m,2H), 6.75 (d,2H), 7.35 (d,2H), 7.45 (s,1H), 8.05 (s,1H).

The following cephalosporins were prepared analogously:

Propionyloxy-1-ethyl-1 7-{D-α-[3-(4-hydroxy-2-(2'-furylmethylamino)-5-pyrimidinyl)-ureido]-p-hydroxy-phenylacetamido}-3-[(1-methyl-tetrazol-5-yl)-thiomethyl]-ceph-3-em-4-carboxylate; and Pivaloyloxymethyl 7-{D-α-[3-(4-hydroxy-2-(2'-furylmethylamino-5-pyrimidinyl)-ureido]-p-hydroxy-phenyl-acetamido}-3-acetoxymethyl-ceph-3-em-4-carboxylate.

EXAMPLE 140

Sodium 7-{D-α-[3-(4-Hydroxy-2-(3'-pyridylmethylamino)-5-pyrimidinyl)-ureido]-p-hydroxy-phenyl-acetamido}-3-[(4'-aminocarbonyl-pyridino)-methyl]-ceph-3-em-4-carboxylate A mixture of 2 mmols of the cephalosporin of Example 90 and 2.5 mmol of pyridine carboxamide, 4 gm of potassium thiocyanate and 10 ml of water was heated at 50° C. for 8 hours. The resulting solution was introduced into a column filled with the ion exchange resin Amberlite XAD-2, and eluted first with water and then with a 7:3 mixture of water and methanol. From the fractions containing the desired product methanol was distilled off in vacuo, and the solution was freeze-dried.

NMR-Spectrum (D$_2$O): 3.55 (m,2H), 4.5 (s,2H), 5.1 (d,1H), 5.4 (q,2H), 5.7 (s,1H), 5.8 (d,1H), 6.8 (d,2H), 7.4 (m,2+1H), 7.7 (m,1H), 8.15 (s,1H), 8.3 (m,2H), 8.5 (m,2H), 9.0 (m,2H).

The following compounds were prepared analogously:

Sodium 7-{D-α-[3-(4-hydroxy-2-(2'-thienylmethylamino)-5-pyrimidinyl)-ureido]-p-hydroxy-phenyl-acetamido}-3-(pyridinomethyl)-ceph-3-em-4-carboxylate;

Sodium 7-{D-α-[3-(4-hydroxy-2-(2'-thienylmethylamino)-5-pyrimidinyl)-ureido]-p-hydroxy-phenyl-acetamido}-3-[(4'-aminocarbonyl-pyridino)-methyl]-ceph-3-em-4-carboxylate; and Sodium 7-{D-α-[3-(4-hydroxy-2-(2'-furylmethylamino)-5-pyrimidinyl)-ureido]-p-hydroxy-phenyl-acetamido}-3-[(4'-aminocarbonyl-pyridino)-methyl]-ceph-3-em-4-carboxylate.

EXAMPLE 141

Sodium 7-{D-α-[(4-hydroxy-2-(2'-methyl-5°-pyrimidinylmethylamino-5-pyrimidinyl)-ureido]-p-hydroxy-phenylacetamido}-3-acetoxymethyl-ceph-3-em-4-carboxylate Prepared according to the method described in Example 44, starting from benzhydryl 7-amino-3-acetoxymethyl-ceph-3-em-4-carboxylate and the ureidocarboxylic acid of Example II(am).

Yield: 52% (sodium salt);

IR-Spectrum: 1760, 1660, 1610, 1540 cm$^{-1}$;

NMR-Spectrum (DMSO+CD$_3$OD), signals at ppm: 2.05 (s,3H), 3.45 (q,2H), 4.40 (s,2H), 4.80 (m,3H), 5.55 (s,1H), 5.60 (d,1H), 6.70 (d,2H), 7.25 (d,2H), 8.05 (s,1H), 8.65 (s,2H).

EXAMPLE 142

Sodium 7-{D-α-[(4-hydroxy-2-(2'-methyl-5'-pyrimidinylmethylamino-5-pyrimidinyl)-ureido]-p-hydroxy-phenyl-acetamido}-3-[(1-methyl-tetrazol-5-yl)-thiomethyl]-ceph-3-em-4-carboxylate Prepared according to the method described in Example 44, starting from the ureidocarboxylic acid of Example II(am) and benzhydryl 7-amino-3-[(1-methyl-tetrazol-5-yl)-thiomethyl]-ceph-3-em-4-carboxylate.

Yield: 58% (sodium salt);

IR-Spectrum: 1760, 1660, 1615 cm$^{-1}$;

NMR-Spectrum (DMSO+CD$_3$OD), signals at ppm: 3.50 (q,2H), 3.90 (s,3H), 4.2–4.5 (m,2+2H), 4.90 (d,1H), 5.50 (s,1H), 5.60 (d,1H), 6.75 (d,2H), 7.30 (d,2H), 8.05 (s,1H), 8.65 (s,2H).

The compounds of the formula I and their non-toxic, pharmacologically acceptable salts have useful pharmacodynamic properties and are very compatible. They can, therefore, be used for the prophylaxis and chemotherapy of local and systemic infections in the human or veterinary medicine. The diseases which can be prevented or cured with the compounds according to the invention, include, for example, diseases of the respiratory tract, of the pharingeal cavity or of the urinary tract; the compounds are particularly effective against pharyngitis, pneumonia, peritonitis, pyelonephritis, otitis, cystitis, endocarditis, bronchitis, arthritis and general systemic infections. Furthermore, these compounds can be used as active ingredients for preserving inorganic or organic materials, especially organic materials such as polymers, lubricants, dyes, fibers, leather, paper and wood, as well as food.

These utilities are made possible by the fact that the compounds of the formula I and their salts possess a cery strong activity in vitro as well as in vivo against harmful microorganisms, particularly against gramposi- tive and gramnegative bacteria and against microorgan- isms similar to bacteria, wherefore they have an espe- cially broad spectrum of activity.

With these β-lactams, for example, local and/or sys- temic diseases can be treated and/or prevented which are caused by the following pathogens or mixtures thereof:

Micrococcaceae, such as staphylococci;
Lactobacteriaceae, such as streptococci;
Neisseriaceae, such as neisseria;
Corynebacteriaceae, such as corynebacteria
Enterobacteriaceae, such as escherichiae-bacteria of the coli group;
Klebsiella bacteria, e.g. K. pneumonia;
Proteae bacteria of the proteus group, e.g. proteus vulgaris;
Salmonella bacteria, e.g. s. thyphimurium;
Shigella bacteria, e.g., shigella dysenteriae;
Pseudomonas bacteria, e.g. pseudomonas aeruginosa;
Aeromonas bacteria, e.g. aeromonas lique faciens;
Spirillaceae, such as vibrio bacteria, e.g., vibrio chol- erae;
Parvobacteriaceae or brucellaceae, such as pasteu- rella bacteria;
Brucella bacteria; e.g. brucella abortus;
Haemophilus bacteria, e.g. haemophilus influencae;
Bordetella pertussis;
Moraxella bacteria, e.g. moraxella lacunata;
Bacteriodaceae, such as bacteroides bacteria;
Fusiforme bacteria, e.g. fusobacterium fusiforme;
Sphaerophorus bacteria, e.g. spaerophorus necroph- orus;
Bacillaceae, such as aerobe spore formers, e.g. bacil- lus anthracis;
Anaerobe spore former chlostridia, e.g. chlostridium perfringens;
Spirochaetaceae, such as borrelia bacteria;
Treponema bacteria, e.g. treponema palidum;
Leptospira bacteria, such as leptospira interrogans.

The above list of pathogens is merely illustrative and should not in any way be considered restrictive.

In the following tables I and II typical, especially effective penicillins and cephalosporins according to the invention are listed. The indicated penicillins can be prepared according to method A or B, and the cephalo- sporins according to method A, B or C.

TABLE I

Penicillins

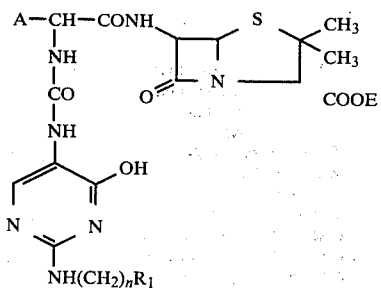

| A | —(CH$_2$)$_n$R$_1$ | E |
|---|---|---|
| p-HO—Phenyl | 2-Pyridyl | H |
| Phenyl | 3-Pyridyl | H |
| p-HO—Phenyl | 3-Pyridyl | H |
| p-HO—Phenyl | 6-Hydroxy-3-pyridyl- | H |
| p-HO—Phenyl | 2-Pyridylmethyl- | H |
| Phenyl | 3-Pyridylmethyl- | H |
| p-HO—Phenyl | 3-Pyridylmethyl- | H |
| p-HO—Phenyl | 4-Pyridylmethyl- | H |
| p-HO—Phenyl | 3-Pyridylmethyl- | —CH$_2$OCOC(CH$_3$)$_3$ |
| p-HO—Phenyl | 5-Pyrimidinyl | H |
| p-HO—Phenyl | 2-Amino-5-pyrimidinyl- | H |
| p-HO—Phenyl | 2-Propylamino-5-pyrimidinyl | H |
| p-HO—Phenyl | 1,2,3,4,-Tetrahydro-1,3-dimethyl-2,4-dioxo-5-pyrimidinyl | H |
| p-HO—Phenyl | 2-Cyclopropyl-4-hydroxy-5-pyrimidinyl- | H |
| p-HO—Phenyl | 4-Pyrimidinylmethyl- | H |
| p-HO—Phenyl | 2-Methyl-5-pyrimidinyl-methyl | H |
| p-HO—Phenyl | 5-Methyl-2-thienyl- | H |
| p-HO—Phenyl | 5-Ethoxycarbonyl-2-thienyl | H |
| p-HO—Phenyl | 5-Aminocarbonyl-2-thienyl | H |
| Phenyl | 2-Thienylmethyl- | H |
| p-HO—Phenyl | 2-Thienylmethyl- | H |
| p-HO—Phenyl | 2-Thienylmethyl- | —CH$_2$OCOC(CH$_3$)$_3$ |
| p-HO—Phenyl | 2-Thienylmethyl- | —CHOCOC$_2$H$_5$<br>\|<br>CH$_3$ |

TABLE I-continued
Penicillins

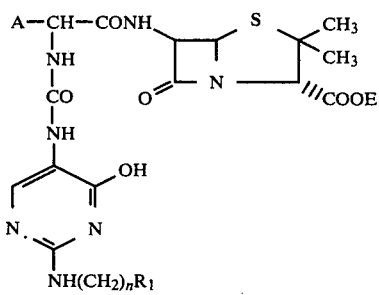

| A | —(CH$_2$)$_n$R$_1$ | E |
|---|---|---|
| m,p-Di-OH—Phenyl | 2-Thienylmethyl- | H |
| 2-Thienyl | 2-Thienylmethyl- | H |
| 2-Furyl | 2-Thienylmethyl- | H |
| p-HO—Phenyl | 3-Thienylmethyl- | H |
| p-HO—Phenyl | 5-Methyl-2-thienyl-methyl | H |
| p-HO—Phenyl | 5-Chloro-2-thienyl-methyl | H |
| Phenyl | 2-Furylmethyl- | H |
| p-HO—Phenyl | 2-Furylmethyl- | H |
| p-HO—Phenyl | 2-Furylmethyl- | —CH$_2$OCOC(CH$_3$)$_3$ |
| p-HO—Phenyl | 2-Furylmethyl- | —CHOCOC$_2$H$_5$<br>\|<br>CH$_3$ |
| m,p-Di-HO—Phenyl | 2-Furylmethyl- | H |
| 2-Furyl | 2-Furylmethyl- | H |
| 3-Furyl | 2-Furylmethyl- | H |
| 2-Thienyl | 2-Furylmethyl | H |
| 3-Thienyl | 2-Furylmethyl | H |
| p-HO—Phenyl | 5-Methyl-2-furylmethyl | H |
| p-HO—Phenyl | Tetrahydro-2-furylmethyl | H |
| p-HO—Phenyl | 5-Aminosulfonyl-2-thienyl-methyl | H |
| p-HO—Phenyl | 5-Aminosulfonyl-2-thienylmethyl | —CH$_2$OCOC(CH$_3$)$_3$ |
| p-HO—Phenyl | 6-Methylsulfinyl-3-pyridyl | H |
| p-HO—Phenyl | 6-Methylsulfinyl-3-pyridyl | —CH$_2$OCOC(CH$_3$)$_3$ |
| p-HO—Phenyl | 6-Methylsulfonyl-3-pyridyl | H |
| p-HO—Phenyl | 6-Methylsulfonyl-3-pyridyl | —CH$_2$OCOC(CH$_3$)$_3$ |
| p-HO—Phenyl | 4-Methyl-2-thiazolyl- | H |
| p-HO—Phenyl | 4-Methyl-2-thiazolylmethyl | H |
| p-HO—Phenyl | 5-Methyl-1,3,4-thiadiazol-2-yl | H |
| p-HO—Phenyl | 1,3,4-Triazol-2-yl-methyl- | H |
| p-HO—Phenyl | 5-Tetrazolylmethyl- | H |
| p-HO—Phenyl | 2-Hydroxy-5-pyrimidinyl | H |
| p-HO—Phenyl | 2,4-Dihydroxy-5-pyrimidinyl | H |
| p-HO—Phenyl | 4,6-Dihydroxy-5-pyrimidinyl | H |
| p-HO—Phenyl | 2,6-Dihydroxy-4-pyrimidinyl | H |

TABLE II
Cephalosporins

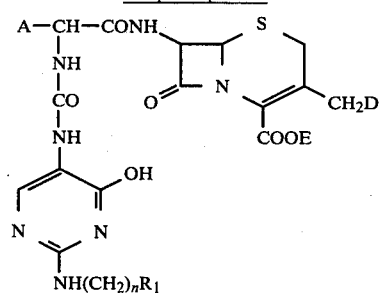

| | A | —(CH$_2$)$_n$R$_1$ | D | E |
|---|---|---|---|---|
| 1 | p-HO—Phenyl | 3-Pyridyl | —OCOCH$_3$ | H |

TABLE II-continued

Cephalosporins

[Structure: A—CH(NH—CO—NH—[2-amino-pyrimidinyl with OH and NH(CH₂)ₙR₁])—CONH— cephem with CH₂D at 3-position and COOE]

| | A | —(CH₂)ₙR₁ | D | E |
|---|---|---|---|---|
| 2 | p-HO—Phenyl | 3-Pyridyl | —S—(1-methyl-tetrazol-5-yl) | H |
| 3 | p-HO—Phenyl | 6-Methylsulfinyl-3-pyridyl | —S—(1-methyl-tetrazol-5-yl) | H |
| 4 | p-HO—Phenyl | 6-Methylsulfinyl-3-pyridyl | —OCOCH₃ | H |
| 5 | p-HO—Phenyl | 6-Methylsulfonyl-3-pyridyl | —S—(1-methyl-tetrazol-5-yl) | H |
| 6 | p-HO—Phenyl | 6-Methylsulfonyl-3-pyridyl | —OCOCH₃ | H |
| 7 | 2-Furyl | 6-Methylsulfinyl-3-pyridyl | —S—(1-methyl-tetrazol-5-yl) | H |
| 8 | 2-Thienyl | 6-Methylsulfinyl-3-pyridyl | —S—(1-methyl-tetrazol-5-yl) | H |
| 9 | p-HO—Phenyl | 6-Hydroxy-3-pyridyl | —S—(1-methyl-tetrazol-5-yl) | H |
| 10 | Phenyl | 3-Pyridylmethyl | —S—(1-methyl-tetrazol-5-yl) | H |
| 11 | p-HO—Phenyl | 3-Pyridylmethyl | H | H |
| 12 | p-HO—Phenyl | 3-Pyridylmethyl | —OCOCH₃ | H |
| 13 | p-HO—Phenyl | 3-Pyridylmethyl | —OCONH₂ | H |

TABLE II-continued
Cephalosporins
| | A | —(CH$_2$)$_n$R$_1$ | D | E |
|---|---|---|---|---|
| 14 | p-HO—Phenyl | 3-Pyridylmethyl | 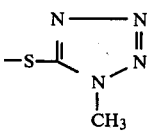 | H |
| 15 | p-HO—Phenyl | 3-Pyridylmethyl | 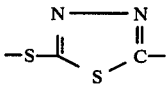 | —CH$_2$OCOC(CH$_3$)$_3$ |
| 16 | p-HO—Phenyl | 3-Pyridylmethyl | 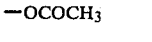 | H |
| 17 | 2-Furyl | 3-Pyridylmethyl | —OCOCH$_3$ | H |
| 18 | 2-Furyl | 3-Pyridylmethyl | 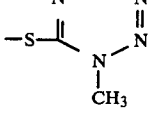 | H |
| 19 | 3-Furyl | 3-Pyridylmethyl | 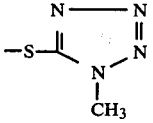 | H |
| 20 | 2-Thienyl | 3-Pyridylmethyl | 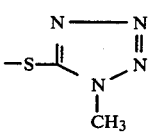 | H |
| 21 | p-HO—Phenyl | 2-Pyridylmethyl | 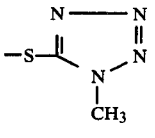 | H |
| 22 | p-HO—Phenyl | 4-Pyridylmethyl | 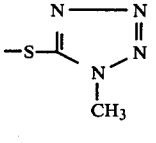 | H |
| 23 | p-HO—Phenyl | 5-Pyrimidinyl | 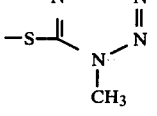 | H |

TABLE II-continued

Cephalosporins

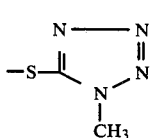

| | A | —(CH$_2$)$_n$R$_1$ | D | E |
|---|---|---|---|---|
| 24 | p-HO—Phenyl | 2-Methyl-5-pyrimidinyl | H | H |
| 25 | p-HO—Phenyl | 2-Methyl-5-pyrimidinyl | —OCOCH$_3$ | H |
| 26 | p-HO—Phenyl | 2-Methyl-5-pyrimidinyl | —OCONH$_2$ | H |
| 27 | p-HO—Phenyl | 2-Methyl-5-pyrimidinyl | 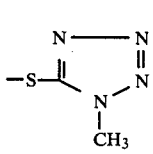 | H |
| 28 | p-HO—Phenyl | 2-Methyl-5-pyrimidinyl | 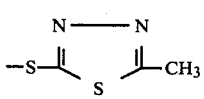 | —CH$_2$OCOC(CH$_3$)$_3$ |
| 29 | p-HO—Phenyl | 2-Methyl-5-pyrimidinyl | 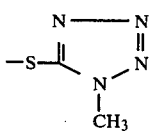 | H |
| 30 | 2-Furyl | 2-Methyl-5-pyrimidinyl | —OCOCH$_3$ | H |
| 31 | 2-Furyl | 2-Methyl-5-pyrimidinyl | 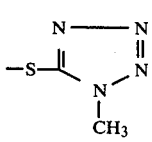 | H |
| 32 | 2-Thienyl | 2-Methyl-5-pyrimidinyl | 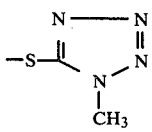 | H |
| 33 | p-HO—Phenyl | 5-Ethoxycarbonyl-2-thienyl | —OCOCH$_3$ | H |
| 34 | p-HO—Phenyl | 5-Ethoxycarbonyl-2-thienyl | 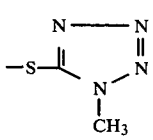 | H |
| 35 | p-HO—Phenyl | 5-Ethoxycarbonyl-2-furyl | 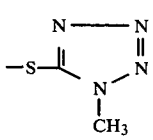 | H |

TABLE II-continued
Cephalosporins

|  | A | —(CH$_2$)$_n$R$_1$ | D | E |
|---|---|---|---|---|
| 36 | p-HO—Phenyl | 5-Aminosulfonyl-2-thienylmethyl | 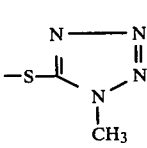 | H |
| 37 | p-HO—Phenyl | 5-Aminosulfonyl-2-thienylmethyl | 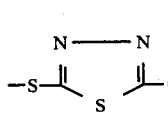 | —CH$_2$OCOC(CH$_3$)$_3$ |
| 38 | p-HO—Phenyl | 5-Aminosulfonyl-2-thienylmethyl | —OCOCH$_3$ | H |
| 39 | p-HO—Phenyl | 5-Aminosulfonyl-2-thienylmethyl | —OCONH$_2$ | H |
| 40 | p-HO—Phenyl | 5-Aminosulfonyl-2-thienylmethyl | 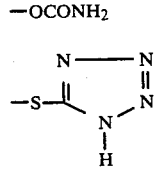 | H |
| 41 | p-HO—Phenyl | 2-Thienylmethyl- |  | H |
| 42 | p-HO—Phenyl | 2-Thienylmethyl- | —OCOCH$_3$ | H |
| 43 | p-HO—Phenyl | 2-Thienylmethyl- | —OCONH$_2$ | H |
| 44 | p-HO—Phenyl | 2-Thienylmethyl- | 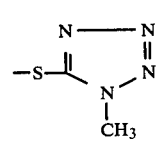 | H |
| 45 | p-HO—Phenyl | 2-Thienylmethyl | 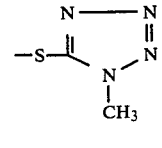 | H |
| 46 | p-HO—Phenyl | 2-Thienylmethyl- | 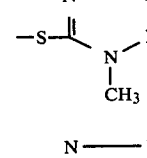 | —CH$_2$OCOC(CH$_3$)$_3$ |
| 47 | p-HO—Phenyl | 2-Thienylmethyl- | 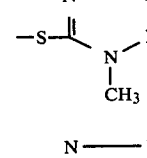 | —CHOCOC$_2$H$_5$<br>\|<br>CH$_3$ |
| 48 | p-HO—Phenyl | 2-Thienylmethyl- | 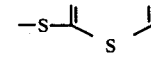 | H |

TABLE II-continued

Cephalosporins $$A-CH-CONH \cdots \text{(cephalosporin nucleus with } CH_2D, COOE\text{)}$$

with the ureido side chain containing pyrimidine –OH and $NH(CH_2)_nR_1$.

| | A | —(CH$_2$)$_n$R$_1$ | D | E |
|---|---|---|---|---|
| 49 | p-HO—Phenyl | 2-Thienylmethyl | -S-(1,3,4-thiadiazol-2-yl) | H |
| 50 | p-HO—Phenyl | 2-Thienylmethyl | -S-(1,3,4-thiadiazol-2-yl) isomer | H |
| 51 | p-HO—Phenyl | 2-Thienylmethyl | -S-(5-NHCH$_3$-1,3,4-thiadiazol-2-yl) | H |
| 52 | p-HO—Phenyl | 2-Thienylmethyl | -S-(5-NHCOCH$_3$-1,3,4-thiadiazol-2-yl) | H |
| 53 | p-HO—Phenyl | 2-Thienylmethyl | -S-(tetrazol-yl, NH) | H |
| 54 | p-HO—Phenyl | 2-Thienylmethyl | -S-(5-CH$_3$-1,3,4-oxadiazol-2-yl) | H |
| 55 | m,p-Di-OH—Phenyl | 2-Thienylmethyl | -S-(1-CH$_3$-tetrazol-5-yl) | H |
| 56 | 2-Furyl | 2-Thienylmethyl | —OCOCH$_3$ | H |
| 57 | 2-Furyl | 2-Thienylmethyl | -S-(1-CH$_3$-tetrazol-5-yl) | H |
| 58 | 3-Furyl | 2-Thienylmethyl | -S-(1-CH$_3$-tetrazol-5-yl) | H |
| 59 | 2-Thienyl | 5-Aminosulfonyl-2-thienyomethyl | -S-(1-CH$_3$-tetrazol-5-yl) | H |

TABLE II-continued

Cephalosporins

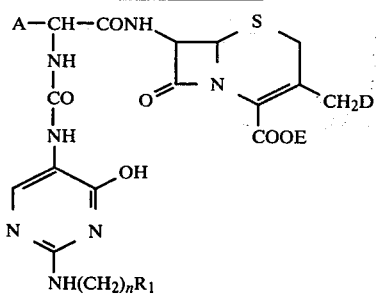

| | A | —(CH$_2$)$_n$R$_1$ | D | E |
|---|---|---|---|---|
| 60 | 2-Thienyl | 2-Thienylmethyl | -S-(N-methyl tetrazolyl) | H |
| 61 | p-HO—Phenyl | 3-Thienylmethyl | -S-(N-methyl tetrazolyl) | H |
| 62 | Phenyl | 2-Furylmethyl | —OCOCH$_3$ | H |
| 63 | p-HO—Phenyl | 2-Furylmethyl | H | H |
| 64 | p-HO—Phenyl | 2-Furylmethyl | —OCOCH$_3$ | H |
| 65 | p-HO—Phenyl | 2-Furylmethyl | —OCONH$_2$ | H |
| 66 | p-HO—Phenyl | 2-Furylmethyl | -S-(NH tetrazolyl) | H |
| 67 | p-HO—Phenyl | 2-Furylmethyl | -S-(N-methyl tetrazolyl) | H |
| 68 | p-HO—Phenyl | 2-Furylmethyl | -S-(N-methyl tetrazolyl) | —CH$_2$OCOC(CH$_3$)$_3$ |
| 69 | p-HO—Phenyl | 2-Furylmethyl | -S-(N-methyl tetrazolyl) | —CHOCOC$_2$H$_5$<br>    \|<br>   CH$_3$ |
| 70 | p-HO—Phenyl | 2-Furylmethyl | -S-(methyl thiadiazolyl) | H |
| 71 | p-HO—Phenyl | 2-Furylmethyl | -S-(thiadiazolyl) | H |
| 72 | p-HO—Phenyl | 2-Furylmethyl | -S-(thiadiazolyl) | H |

TABLE II-continued

Cephalosporins

A—CH—CONH—[β-lactam-cephem]—CH₂D, COOE structure with NH-CO-NH linked to pyrimidine bearing OH and NH(CH₂)ₙR₁

| | A | —(CH₂)ₙR₁ | D | E |
|---|---|---|---|---|
| 73 | p-HO—Phenyl | 2-Furylmethyl | -S-[1,3,4-thiadiazol-2-yl]-NHCH₃ | H |
| 74 | p-HO—Phenyl | 2-Furylmethyl | -S-[1,3,4-thiadiazol-2-yl]-NHCOCH₃ | H |
| 75 | p-HO—Phenyl | 2-Furylmethyl | -S-[tetrazol-NH] | H |
| 76 | p-HO—Phenyl | 2-Furylmethyl | -S-[1,3,4-oxadiazol-2-yl]-CH₃ | H |
| 77 | p-HO—Phenyl | 2-Furylmethyl | -S-[1,2,4-triazol-NH] | H |
| 78 | p-HO—Phenyl | 2-Furylmethyl | -S-[1,3,4-thiadiazol-2-yl]-N(CH₃)₂ | H |
| 79 | m,p-Di-OH—Phenyl | 2-Furylmethyl | -S-[1-methyltetrazol-5-yl] | H |
| 80 | 2-Furyl | 2-Furylmethyl | —OCOCH₃ | H |
| 81 | 2-Furyl | 2-Furylmethyl | -S-[1-methyltetrazol-5-yl] | H |
| 82 | 2-Thienyl | 2-Furylmethyl | —OCOCH₃ | H |
| 83 | 2-Thienyl | 2-Furylmethyl | -S-[1-methyltetrazol-5-yl] | H |
| 84 | 2-Thienyl | 2-Furylmethyl | -S-[1-methyltetrazol-5-yl] | —CH₂OCOC(CH₃)₃ |

TABLE II-continued

Cephalosporins

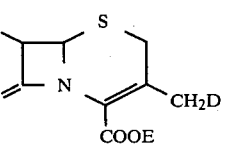

| | A | —(CH$_2$)$_n$R$_1$ | D | E |
|---|---|---|---|---|
| 85 | p-HO—Phenyl | 3-Furylmethyl | 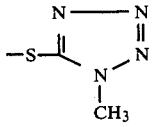 | H |
| 86 | p-HO—Phenyl | 3-Furylmethyl | —OCOCH$_3$ | H |
| 87 | p-HO—Phenyl | Tetrahydro-2-furylmethyl | 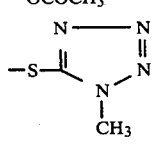 | H |
| 88 | p-HO—Phenyl | 6-Methylsulfinyl-3-pyridyl | —OCOCH$_3$ | H |
| 89 | p-HO—Phenyl | 6-Methylsulfinyl-3-pyridyl | 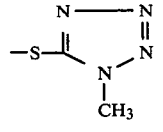 | H |
| 90 | p-HO—Phenyl | 6-Methylsulfinyl-3-pyridyl | 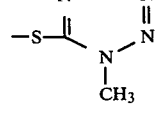 | —CH$_2$OCOC(CH$_3$)$_3$ |
| 91 | p-HO—Phenyl | 6-Methylsulfinyl-3-pyridyl | 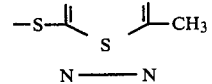 | H |
| 92 | 2-Thienyl | 6-Methylsulfinyl-pyridyl | 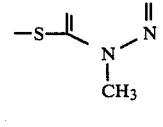 | H |
| 93 | p-HO—Phenyl | 6-Methylsulfonyl 3-pyridyl | —OCOCH$_3$ | H |
| 94 | p-HO—Phenyl | 6-Methylsulfonyl-3-pyridyl | 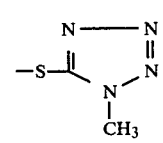 | H |
| 95 | p-HO—Phenyl | 6-Methylsulfonyl-3-pyridyl | 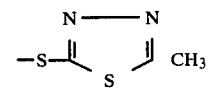 | H |

TABLE II-continued

Cephalosporins

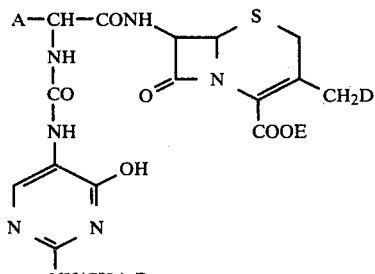

| | A | —(CH$_2$)$_n$R$_1$ | D | E |
|---|---|---|---|---|
| 96 | 2-Thienyl | 6-Methylsulfonyl-3-pyridyl | 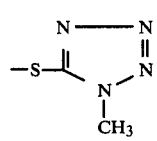 | H |
| 97 | p-HO—Phenyl | 5-Methy-2-pyrrolylmethyl | —OCOCH$_3$ | H |
| 98 | p-HO—Phenyl | 5-Methyl-2-pyrrolylmethyl | 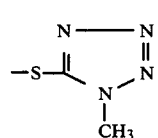 | H |
| 99 | p-HO—Phenyl | 4-Methyl-2-imidazolyl-methyl | 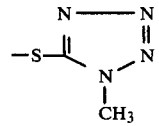 | H |
| 100 | p-HO—Phenyl | 4-Methyl-2-thiazolyl- | 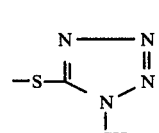 | H |
| 101 | p-HO—Phenyl | 4-Methyl-2-thiazolylmethyl- | 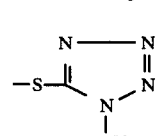 | H |
| 102 | p-HO—Phenyl | 5-Methyl-2-thiadiazolyl- | 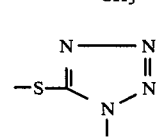 | H |
| 103 | p-HO—Phenyl | 2-Triazolyl-methyl | 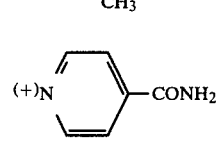 | H |
| 104 | p-HO—Phenyl | 2-Thienylmethyl | 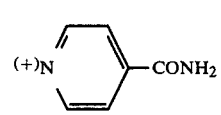 | — |
| 105 | p-HO—Phenyl | 2-Thienylmethyl | 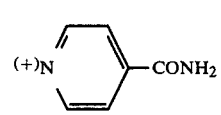 | — |

TABLE II-continued

Cephalosporins

[Structure shown: A—CH(NH—CO—NH—[pyrimidine with OH and NH(CH₂)ₙR₁])—CONH—[cephem nucleus]—CH₂D, with COOE group]

| | A | —(CH₂)ₙR₁ | D | E |
|---|---|---|---|---|
| 106 | p-HO—Phenyl | 2-Furylmethyl | (+)N-pyridyl-CONH₂ | — |
| 107 | p-HO—Phenyl | 3-Pyridylmethyl | (+)N-pyridyl-CONH₂ | — |
| 108 | p-HO—Phenyl | 6-Methylsulfonyl-3-pyridyl | (+)N-pyridyl-CONH₂ | — |
| 109 | p-HO—Phenyl | 5-Aminosulfonyl-2-thienylmethyl | (+)N-pyridyl-CONH₂ | — |
| 110 | p-HO—Phenyl | 6-Methylsulfinyl-3-pyridyl | (+)N-pyridyl-CONH₂ | — |
| 111 | p-HO—Phenyl | 2-Methyl-5-pyrimidinyl-methyl | (+)N-pyridyl-CONH₂ | — |
| 112 | p-HO—Phenyl | 5-Aminocarbonyl-2-thienyl | OCOCH₃ | H |
| 113 | p-HO—Phenyl | 5-Aminocarbonyl-2-thienyl | —S-(1-methyl-tetrazol-5-yl) | H |
| 114 | 2-Thienyl | 5-Aminocarbonyl-2-thienyl | —S-(1-methyl-tetrazol-5-yl) | H |
| 115 | p-HO—Phenyl | 6-Hydroxy-3-pyridyl | —OCOCH₃ | H |
| 116 | p-HO—Phenyl | 6-Hydroxy-3-pyridyl | —S-(1-methyl-tetrazol-5-yl) | H |

TABLE II-continued

Cephalosporins

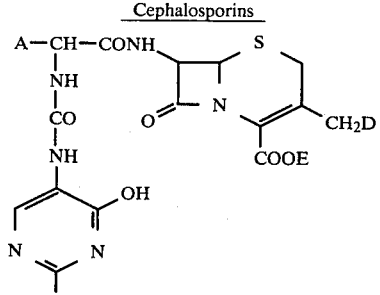

|     | A | —(CH$_2$)$_n$R$_1$ | D | E |
|-----|---|---|---|---|
| 117 | p-HO—Phenyl | 6-Hydroxy-3-pyridyl | 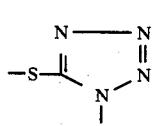 | H |
| 118 | p-HO—Phenyl | 2-Hydroxy-5-pyrimidinyl | —OCOCH$_3$ | H |
| 119 | p-HO—Phenyl | 2-Hydroxy-5-pyrimidinyl | 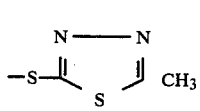 | H |
| 120 | p-HO—Phenyl | 2-Hydroxy-5-pyrimidinyl | 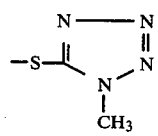 | H |
| 121 | 2-Thienyl | 2-Hydroxy-5-pyrimidinyl | 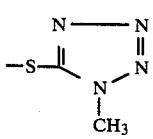 | H |
| 122 | 2-Thienyl | 6-Hydroxy-3-pyridyl | 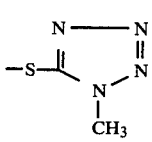 | H |
| 123 | p-HO—Phenyl | 2,4-Dihydroxy-5-pyrimidinyl | 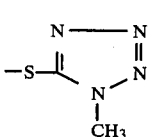 | H |
| 124 | p-HO—Phenyl | 2,6-Dihydroxy-4-pyrimidinyl | —OCOCH$_3$ | H |
| 125 | p-HO—Phenyl | 2,6-Dihydroxy-4-pyrimidinyl | 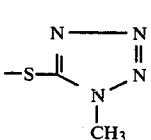 | H |
| 126 | p-HO—Phenyl | 4,6-Dihydroxy-2-pyrimidinyl | —OCOCH$_3$ | H |
| 127 | p-HO—Phenyl | 4,6-Dihydroxy-2-pyrimidinyl |  | H |

The effectiveness of the β-lactam antibiotics of the present invention can be demonstrated by the following tests:

1. In vitro tests:

These tests were performed according to the method of the serial dilution test in the microtiter system. The effect of the substances on bacteriostasis was examined in a fluid medium. The activity of bacteriostasis was examined at the following concentrations: 128, 64, 32, 16, 8, 4, 2, 1, 0.5, 0.25, 0.12 and 0.06 μg/ml. A nutrient medium of the following composition was used. 10 gm of peptone, 8 gm of meat extract-oxoid, 3 gm of sodium chloride, 2 gm of sec. sodium phosphate were diluted with distilled water to 100 ml (pH 7.2–7.4). Only in the test against streptococci 1% of glucose was added. The age of the primary cultures was about 20 hours. The standardization of the pathogen suspension was effected by using a photometer according to "Eppendorf" (test tube dismeter 14 mm, filter 546 nm) with the aid of the turbidity of a comparison suspension consisting of barium sulfate, this suspension being prepared by addition of 3.0 ml of 1% barium chloride solution to 97 ml of 1% sulfuric acid. After the standardization, streptococcus aronson were further diluted to a concentration of 1:15 and the other microorganisms to a concentration of 1:1500 by means of a sodium chloride solution.

16 mg of the test substance were put into a 10 ml-measuring flask and filled up to the mark with the solvent. The further dilution series was standardized with distilled water or the respective solvent.

The cavities of the microtiter plates were filled with 0.2 ml of nutrient medium. Then, 0.01 ml of the corresponding test substance dilution was added and inoculated with 0.01 ml of the standardized suspension. The bacteria were incubated at 37° C. for 18–20 hours. Control tests merely using the solvent were carried out simultaneously.

The measurement was carried out macroscopically to determine the minimal inhibitory (threshold) concentration, i.e. the lower still bacteriostatically effective concentration.

The following test organisms were used:

Staphylococcus aureus SG 511, Escherichia coli ATCC 11 775, Pseudomonas aeruginosa Hamburgensis and Pseudomonas aeruginosa Walter, Serratia marcescens ATCC 13880, Klebsiella pneumoniae ATCC 10 031 and 272, Proteus mirabilis Hamburgensis, Proteus rettgeri, Enterbacter cloaceae ATCC 13 047 and E. Coli R+TEM (β-lactamase carrier).

The following tables III and IV show the minimum inhibiting concentrations (MIC) for typical representatives of the compounds according to this invention:

a. Penicillins

Sodium salts of compounds of the formula I where A=p-hydroxyphenyl and R has the following meanings:

| | |
|---|---|
| 3-Pyridylmethyl | = A |
| 5-Aminocarbonyl-2-thienyl | = B |
| 2-Thienylmethyl | − C |
| 2-Furylmethyl | = D |
| 6-Methylsulfonyl-3-pyridyl | = E |
| 2-Methyl-5-pyrimidinylmethyl | = F |
| 6-Hydroxy-3-pyridyl | = G |
| in comparison with Azlocillin | = H |

TABLE III

| Compound | E. Coli ATCC 9637 | E. Coli ATCC 11775 | Pseud. aerug. Hbg. | Pseud. aerug. Walter | Serrat. marcesc. ATCC 13880 | Klebs. pneum. ATCC 10031 | Klebs. pneum. 272 | Prot. mirabilis | Prot. rettgeri | Eb. cloaceae ATCC 13047 |
|---|---|---|---|---|---|---|---|---|---|---|
| | | | | | MIC-values in μgm/ml | | | | | |
| A | 0.5 | 0.5 | 1 | 1 | 0.5 | 8 | 8 | 0.12 | 1 | 4 |
| B | 0.5 | 0.25 | 1 | 1 | 0.2 | 2 | 2 | 0.06 | 0.5 | ·2 |
| C | 0.5 | 0.5 | 2 | 1 | 0.5 | 2 | 2 | 0.25 | 0.12 | 0.5 |
| D | 0.5 | 1 | 1 | 2 | 0.5 | 4 | 8 | 0.25 | 0.5 | 4 |
| E | 0.2 | 0.2 | 1 | 1 | 0.2 | 2 | 2 | 0.06 | 0.25 | 2 |
| F | 0.5 | 0.5 | 1 | 1 | 0.5 | 8 | 8 | 0.06 | 0.5 | 4 |
| G | 0.2 | 0.2 | 0.5 | 0.5 | 0.1 | 4 | 4 | 0.01 | 0.5 | 4 |
| H | 16 | 8 | 8 | 8 | 4 | 32 | 32 | 2 | 8 | 32 |

(b) Cephalosporins

Sodium salts of compounds of the formula I with the following meanings of A, R and D.

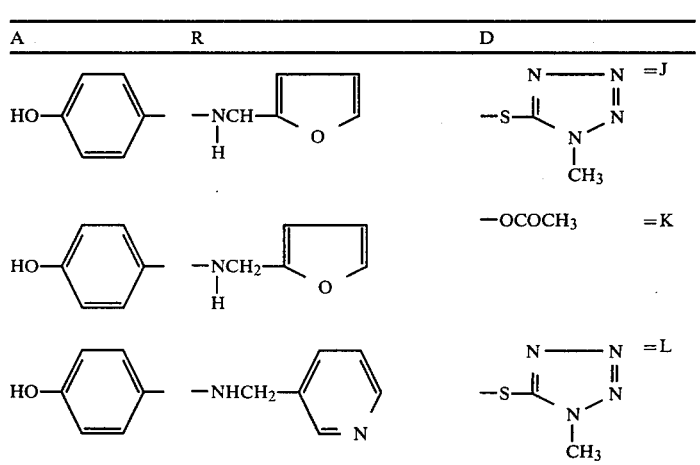

-continued

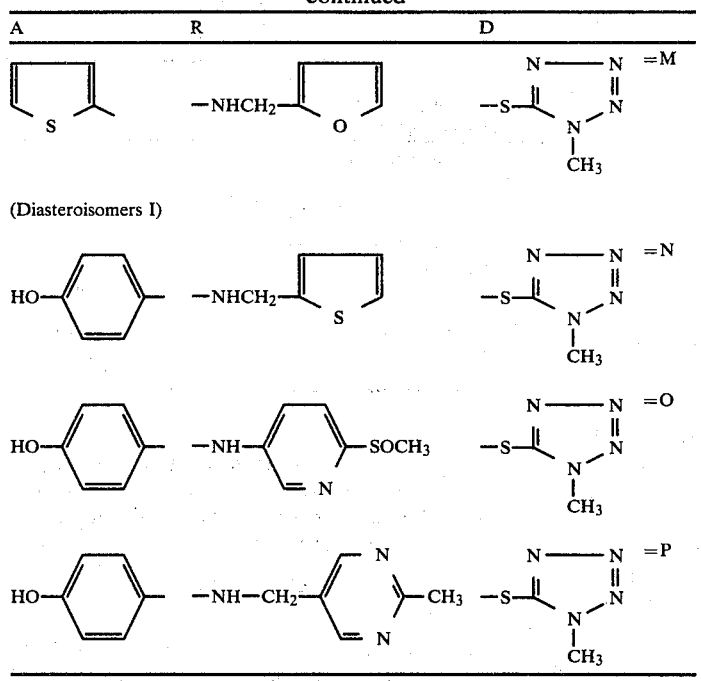

(Diasteroisomers I)

TABLE IV

| Compound | S. aureus SG 511 | E. Coli ATCC 11775 | Pseud. aerug. Hbg. | Pseud. aerug. Walter | Klebs. pneum. ATCC 10031 | Klebs. pneum. 272 | Prot. mir. Hbg. | Prot. rettg. | Eb. cloaceae | E. coli R + TEM | Serr. marcesc. ATCC 13880 |
|---|---|---|---|---|---|---|---|---|---|---|---|
| Cefuroxim | 1 | 8 | >128 | >128 | 2 | 4 | 0.5 | 2 | 32 | 4 | 8 |
| Cephazolin | 0.06 | 4 | >128 | >128 | 1 | 2 | 4 | >128 | >128 | 4 | >128 |
| J | 0.5 | 0.25 | 8 | 4 | 0.5 | 0.5 | 0.12 | 0.5 | 0.5 | 8 | 0.25 |
| K | 1 | 0.5 | 16 | 8 | 1 | 1 | 0.25 | 1 | 4 | 16 | 2 |
| L | 0.5 | 0.12 | 4 | 4 | 0.25 | 0.25 | 0.06 | 0.5 | 0.25 | 4 | 0.25 |
| M | 0.25 | 0.25 | 8 | 4 | 0.25 | 0.5 | 0.12 | 0.5 | 0.25 | 2 | 0.5 |
| N | 0.5 | 0.25 | 8 | 4 | 0.25 | 0.25 | 0.12 | 0.5 | 0.25 | 4 | 0.25 |
| O | 0.25 | 0.25 | 4 | 4 | 0.25 | 0.25 | 0.12 | 0.5 | 0.5 | 4 | 0.5 |
| P | 0.25 | 0.12 | 4 | 4 | 0.25 | 0.5 | 0.06 | 0.25 | 0.5 | 4 | 0.25 |

As can be seen from the above tables, the compounds of the invention are distinctly superior to the comparison compounds in their activity against typical gram-negative hospital bacteria, while retaining the activity against gram-positive bacteria. The good activity against Pseudomonas strains is emphasized.

The acute toxicity was determined by peroral and subcutaneous administration of the compounds of tables III and IV to white mice.

The $LD_{50}$ is the dose which leads to the death of 50% of the animals within 8 days. All compounds showed after oral administration an $LD_{50}$ of more than 4 gm/kg, after subcutaneous administration an $LD_{50}$ of more than 3 gm/kg, i.e. at 3 gm/kg no animal died. This means that the compounds are for practical purposes completely non-toxic.

A number of compounds of this invention were tested in vivo in mice against experimental infections. Bacteria E. coli ATCC 11775 and Psuedomonas aeruginosa Walter were used as pathogens. An intraperitoneal infection with 0.2 ml of a 5% suspension of the bacteria was induced. This corresponds to about $2 \times 10^6$ E. Coli germs and $8 \times 10^5$ pseudomonas germs/mouse. Female NMRI mice were divided into groups of 10 animals each, two control groups remained untreated, the remaining groups were treated with different doses of the respective penicillins or cephalosporins for the determination of the $ED_{50}$ (dose at which 50% of the animals survived). The groups with E. coli infection were treated with the test compound three times on the first day (1, 4, and 7 hours post infectionem) and for two days thereafter twice a day. The groups with the pseudomonas infection were treated with the test compound 6 times on the first day (1, 3, 6, 9, 12 and 15 hours post infectionem) and for two days thereafter twice a day. The observation time was in both cases 7 days. The results of these tests with representatives of the penicillins and cephalosporins according to the invention are shown in the following table:

TABLE V

| Compound | In vivo activity in mice $ED_{50}$ (mg*/kg) |
|---|---|
| (a) E. coli infection (s.c. administration): | |
| A | 0.7 |
| B | 1.3 |
| C | 0.8 |
| D | 0.8 |
| Azlocillin | ~35 |
| J | 0.3 |
| L | 0.2 |
| M | 0.8 |

TABLE V-continued

| Compound | In vivo activity in mice<br>ED$_{50}$ (mg*/kg) |
|---|---|
| N | 0.6 |
| Cefuroxim | 37 |
| (b) Pseudomonas (s.c. administration): | |
| A | 1.2 |
| B | 4.8 |
| C | 2.5 |
| D | 1.5 |
| Azlocillin | ~110 |
| J | 6.3 |
| L | 4.6 |
| Cefuroxim | >200 i.e. at 200 mg/kg all animals died |

*per dose

The further object of the present invention is to provide pharmaceutical compositions for the treatment of infectious diseases in humans as well as in animals.

Preferred pharmaceutical compositions are tablets, coated pills, capsules, granulates, suppositories, solutions, suspensions, emulsions, ointments, gels, cremes, powders and sprays. In human or veterinary medicine it is of advantage to apply the active ingredient or a mixture or different active ingredients of the formula I at a dosage between 5 and 500, preferably between 10 and 200 mg/kg body weight every 24 hours, optionally in the form of several single administrations. A single administration contains the active ingredient or ingredients according to the invention, preferably in amounts of about 1 to about 250, especially 10 to 60 mg/kg body weight. However, it may be necessary to deviate from the mentioned dosages. The deviation depends upon the kind and the body weight of the subject to be treated, on the kind and severity of the disease, on the kind of composition and method of administration of the drug, as well as on the period or interval within which the administration is effected. Thus, it may be sufficient in some cases to take less than the above-mentioned amount of active ingredient, while in other cases the above-mentioned amount of active ingredient must be exceeded. The optimum dosage and method of administration of the active ingredients which are required in any particular case can easily be determined by thos skilled in the art based on their special knowledge.

If the penicillin or cephalosporin compounds are used as animal feed additives, they can be administered at the usual concentrations and together with the feed or with feed compositions or with drinking water. In this manner, an infection by gram-negative or gram-positive bacteria can be prevented, ameliorated and/or cured, and also a growth promotion and an improvement of the utilization of the feed can be achieved.

The compounds of the present invention can be compounded into conventional pharmaceutical means of administration such as tablets, coated pills, capsules or ampules. The single dose for adults is generally between 100 and 1,000 mg, preferably 200 to 500 mg, the daily dose lying between 150 and 5,000 mg, preferably 500 to 2,500 mg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 143

| Tablets | |
|---|---|
| The tablet composition is compounded from the following ingredients: | |
| Pivaloyloxymethyl 7-{D-α-[3-(4-hydroxy-2-(3'-pyridylmethylamino-5-pyrimidinyl)-ureido]-p-hydroxy-phenylacetamido}-3-[(1-methyl-tetrazol-5-yl)-thiomethyl]-ceph-3-em-4-carboxylate | 2.0 parts |
| Lactose | 5.0 parts |
| Potato starch | 1.8 parts |
| Magnesium stearate | 0.1 parts |
| Talcum | 0.1 parts |
| Total | 9.0 parts |

Preparation:

The ingredients are intimately admixed with each other, and the mixture is compressed into 900 mgm-tablets. Each tablet is an oral dosage unit composition containing 200 mgm of the active ingredient.

EXAMPLE 144

Coated pills

The composition of Example 143 is compressed into 900 mgm-pill cores which are subsequently coated with a thin shell consisting essentially of a mixture of sugar, potato starch, talcum and tragacanth. Each coated pill is an oral dosage unit composition containing 200 mgm of the active ingredient.

EXAMPLE 145

Gelatine Capsules 500 mgm-portions of pivaloyloxymethyl 7-{D-α-[3-(4-hydroxy-2-(3'-pyridylmethylamino)-5-pyrimidinyl)-ureido]-p-hydroxy-phenylacetamido}-3-[(1-methyl-tetrazol-5-yl)-thiomethyl]-ceph-3-em-4-carboxylate are filled into hard gelatin capsules of suitable size. Each filled capsule is an oral dosage unit composition.

EXAMPLE 146

Dry Ampules 251 gm of sodium 7-{D-α-[3-(4-hydroxy-2-(3'-pyridylmethylamino)-5-pyrimidinyl)-ureido]-p-hydroxy-phenylacetamido}-3-[(1-methyl-tetrazol-5-yl)-thiomethyl]-ceph-3-em-4-carboxylate are dissolved under aseptic conditions in 2,008 ml of distilled water suitable for injection, and the solution is filtered through a Milliporefilter (pore size 0.22 mm). 2.0 ml-portions of the filtrate are filled into 10 ml-glass ampules, the contents are freeze-dried, and the ampules are then closed with a rubber stopper and an aluminum cap. Each ampule (A) contains 250 mgm of active ingredient.

2.0 ml-portions of a physiological sodium chloride solution suitable for injection are filled into 2 cc-ampules which are then sealed (ampules (B)).

The contents of an ampule B are poured into and thoroughly admixed with an ampule A, whereby an injectable dosage unit composition for intravenous administration is obtained.

20 ml of distilled water suitable for injection are added to the contents of an ampule A, and the resulting solution is dissolved in 250 ml of an aqueous 5% solution of glucose suitable for injection. A solution suitable for continuous intravenous infusion is obtained.

Any one of the other compounds embraced by formula I or I' or a non-toxic, pharmacologically acceptable salt thereof may be substituted for the particular active ingredient in Examples 143 through 145. Likewise, the amount of active ingredient in these illustrative examples may be varied to achieve the dosage unit ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

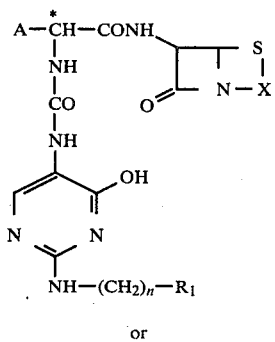

or

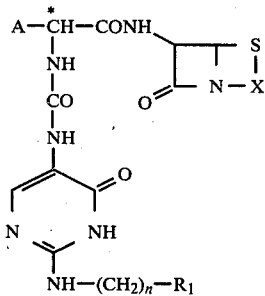

wherein

A is phenyl, 4-hydroxyphenyl, cyclohexyl, cyclohexene-1-yl, cyclohexa-1,4-diene-1-yl, 2-thienyl, 3-thienyl, 2-furyl, 3-furyl or 3,4-disubstituted phenyl, where the substituents are each chlorine, hydroxyl or methoxy;

$R_1$ is 2-, 3- or 4-pyridyl; 6-hydroxy-2- or 3-pyridyl; 2-, 4- or 5-pyrimidinyl; 2,6-dihydroxy-4-pyrimidinyl; 2,4-dihydroxy-5-pyrimidinyl; 4,6-dihydroxy-2-pyrimidinyl; 2-methyl-5-pyrimidinyl; 2-hydroxy-5-pyrimidinyl; 2-amino-2-pyrimidinyl; 5-ethoxycarbonyl-2-thienyl; 2- or 3-thienyl; 5-methyl-2-thienyl; 5-chloro-2-thienyl; 5-aminocarbonyl-2-thienyl; 2- or 3-furyl; 5-methyl-2-furyl; 5-nitro-2-furyl; tetrahydro-2-furyl; 2-pyrrolyl; 2-thiazolyl; 4-methyl-2-thiazolyl; 2-imidazolyl; 4-methyl-2-imidazolyl; 5-methyl-1,3,4-triazol-2-yl; 5-methyl-1,3,4-thiadiazol-2-yl; 5-aminosulfonyl-2-thienyl; 6-methylsulfinyl-3-pyridyl; 6-methylsulfonyl-3-pyridyl; 5-tetrazolyl; 6-methoxy-3-pyridyl; 2-oxazolyl; 1,2,4-triazol-2-yl; or 5-methyl-1,2,4-triazol-2-yl;

n is 0 or 1;

X is

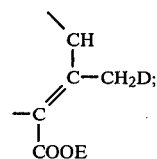

D is -S-Het, where Het is 1-methyl-tetrazol-5-yl; tetrazol-5-yl; 3-methyl-1,2,4-thiadiazol-5-yl; 1,2,4-thiadiazol-5-yl; 1,3,4-thiadiazol-5-yl; 2-methyl-1,3,4-thiadiazol-5-yl; 2-methylamino-1,3,4-thiadiazol-5-yl; 2-dimethylamino-1,3,4-thiadiazol-5-yl; 2-formylamino-1,3,4-thiadiazol-5-yl; 2-acetylamino-1,3,4-thiadiazol-5-yl; 2-methyl-1,3,4-oxadiazol-5-yl; 1,2,3-triazol-4-yl; or 1,2,4-triazol-3-yl; and E is hydrogen or a protective group which is easily removable in vitro or in vivo;

or, when E is hydrogen, a non-toxic, pharmacologically acceptable salt thereof.

2. A compound of claim 1, where

A is phenyl, p-hydroxyphenyl, 2-thienyl, 2-furyl or 3-furyl;

E is hydrogen or pivaloyloxymethyl;

D is S-Het, where Het is tetrazol-5-yl, 1-methyl-tetrazol-5-yl, 1,3,4-thiadiazol-5-yl or 2-methyl-1,3,4-thiadiazol-5-yl; and —$(CH_2)_n$—$R_1$ is 3-pyridyl, 6-methylsulfinyl-3-pyridyl, 6-methylsulfonyl-3-pyridyl, 6-hydroxy-3-pyridyl, 5-pyrimidinylmethyl, 2-methyl-5-pyrimidinylmethyl, 2-hydroxy- or 2-hydroxy-5-pyrimidinyl, 4-hydroxy-2-pyrimidinyl, 4,6-dihydroxy-2-pyrimidinyl, 3-pyridylmethyl, 2-furylmethyl, 2-thienylmethyl, 5-aminosulfonyl-2-thienylmethyl, 5-amino-carbonyl-thienyl or 5-ethoxycarbonylthienyl;

or, when E is hydrogen, a non-toxic, pharmacologically acceptable salt thereof.

3. A compound of claim 1, where

A is p-hydroxyphenyl or 2-thienyl;

E is hydrogen;

D is 1-methyl-tetrazol-5-yl; and

—$(CH_2)_n$—$R_1$ is 3-pyridylmethyl, 6-methylsulfinyl-3-pyridyl, 6-methylsuflonyl-3-pyridyl, 6-hydroxy-3-pyridyl, 2-methyl-5-pyrimidinyl-methyl, 2-hydroxy-5-pyrimidinyl, 4-hydroxy-2-pyrimidinyl, 4,6-dihydroxy-2-pyrimidinyl, 5-aminocarbonyl-thienyl, 2-thienylmethyl, 5-aminosulfonyl-2-thienylmethyl or 2-furylmethyl;

or a non-toxic, pharmacologically acceptable salt thereof.

4. A compound of claim 1, where

A, $R_1$, X and D have the meanings defined in claim 1; and

E is benzyl, diphenylmethyl, trityl, tert. butyl, 2,2,2-trichloroethyl, trimethylsilyl, (alkanoyl of 1 to 5 carbon atoms)oxy-(alkyl of 1 to 3 carbon atoms), phthalidyl or indanyl.

5. An antibiotic pharmaceutical dosage unti composition consisting essentially of an inert pharmaceutical carrier and an effective antibiotic amount of a compound of claim 1.

6. The method of inhibiting the growth of or destorying bacteria in a warm-blooded animal, which comprises enterally or parenterally administering to said animal an effective antibiotic amount of a compound of claim 1.

* * * * *

UNITED STATES PATENT AND TRADEMARK OFFICE
CERTIFICATE OF CORRECTION

PATENT NO. : 4,415,566
DATED : November 15, 1983          Page 1 of 3
INVENTOR(S) : BERND WETZEL ET AL.

It is certified that error appears in the above—identified patent and that said Letters Patent is hereby corrected as shown below:

Title page [57], 4th line after second structural formula
          of Abstract: "1,2,4-triadiazol-5-yl"
          should read -- 1,2,4-thiadiazol-5-yl --.
       7th line after 2nd structural formula
          "2-formylamino-1,2,4-" should read
          -- 2-formylamino-1,3,4-   --.

Title page [30]: The priority application No. "2938344"
          should read -- 2928344 --.
Column 4, line 15: "C" should read -- $\overset{*}{C}$ --.
Column 10, line 60: ".. 2-2'-methyl" should read
          -- 2-(2'-methyl --.
Column 29, line 24: "... 2'-pyrimidylamino-" should read
          -- ... 2'-pyridylamino-  --.
Column 41, line 64: "mole" should read -- mol --.
Column 42, line 62: "Example II(c)" should read
          -- Example II(o) --.
Column 44, line 15: "](1-" should read -- [(1-  --.
Column 51, line 52: Before "(m, 3H)" insert -- 8.3 --.
Column 52, line 46: "(2-'-furyl..." should read
          -- (2'-furyl...  --.
Column 54, line 42: "7-{d-α-[-(4-hydroxy" should read
          -- 7-{D-α-[3-(4-hydroxy  --.

UNITED STATES PATENT AND TRADEMARK OFFICE
CERTIFICATE OF CORRECTION

PATENT NO. : 4,415,566

DATED : November 15, 1983    Page 2 of 3

INVENTOR(S) : BERND WETZEL ET AL.

It is certified that error appears in the above—identified patent and that said Letters Patent is hereby corrected as shown below:

Column 54, line 49:  "7-{D-α-[-(4-hydroxy" should read
                     -- 7-{D-α-[3-(4-hydroxy --

Column 55, line 1:   "Sodium 7-55 D-α" should read
                     -- Sodium 7-{D-α --

Column 57, line 48:  "thienylmethylamino" should read
                     -- furylmethylamino --.

Column 60, line 23:  "methyl-5°" should read -- methyl-5' --.

Column 79, No. 92, column of "-CH$_2$)$_n$R$_1$":
                     "6-Methylsulfinyl-pyridyl" should read
                     -- 6-Methylsulfinyl-3-pyridyl --.

Column 89, line 63:  "5% suspension" should read
                     -- 5% mucin suspension --.

UNITED STATES PATENT AND TRADEMARK OFFICE
CERTIFICATE OF CORRECTION

PATENT NO. : 4,415,566

DATED : November 15, 1983

INVENTOR(S) : BERND WETZEL ET AL.

Page 3 of 3

It is certified that error appears in the above—identified patent and that said Letters Patent is hereby corrected as shown below:

Column 94, lines 1 and 2 of Claim 6: "destorying" should read -- destroying --.

Signed and Sealed this

Second Day of October 1984

[SEAL]

Attest:

Attesting Officer

GERALD J. MOSSINGHOFF

Commissioner of Patents and Trademarks